United States Patent
Cai et al.

(10) Patent No.: US 11,116,767 B2
(45) Date of Patent: Sep. 14, 2021

(54) 3,5-DISUBSTITUTED PYRAZOLES USEFUL AS CHECKPOINT KINASE 1 (CHK1) INHIBITORS, AND THEIR PREPARATIONS AND APPLICATIONS

(71) Applicant: PHARMAENGINE, INC., Taipei (TW)

(72) Inventors: Xiong Cai, Bedford, MA (US); Changgeng Qian, Wayland, MA (US); Yanong Daniel Wang, Warren, NJ (US)

(73) Assignee: PHARMAENGINE, INC., Taipei (TW)

(*) Notice: Subject to any disclaimer, the term of this patent is extended or adjusted under 35 U.S.C. 154(b) by 580 days.

(21) Appl. No.: 16/074,195

(22) PCT Filed: Feb. 4, 2016

(86) PCT No.: PCT/CN2016/073454
§ 371 (c)(1),
(2) Date: Jul. 31, 2018

(87) PCT Pub. No.: WO2017/132928
PCT Pub. Date: Aug. 10, 2017

(65) Prior Publication Data
US 2021/0137918 A1 May 13, 2021

(51) Int. Cl.
*A61K 31/497* (2006.01)
*A61P 35/00* (2006.01)
*A61K 31/4745* (2006.01)
*C07D 403/12* (2006.01)

(52) U.S. Cl.
CPC ........ *A61K 31/497* (2013.01); *A61K 31/4745* (2013.01); *A61P 35/00* (2018.01); *C07D 403/12* (2013.01)

(58) Field of Classification Search
CPC C07D 403/12; A61K 31/4745; A61K 31/497; A61K 35/00
See application file for complete search history.

(56) References Cited

U.S. PATENT DOCUMENTS

2011/0144126 A1   6/2011   Farouz et al.

FOREIGN PATENT DOCUMENTS

| CN | 102245597 A | 11/2011 |
|---|---|---|
| EP | 2379532 B1 | 2/2013 |
| JP | 2012-512249 | 5/2012 |
| KR | 10-2011-0084539 | 7/2011 |
| WO | 2005/009435 A1 | 2/2005 |
| WO | 2010/077758 A1 | 7/2010 |
| WO | 2015/120390 A1 | 8/2015 |
| WO | 2015120390 A1 | 8/2015 |

OTHER PUBLICATIONS

International Search Report. (ISR) and Written Opinion (WO) dated Nov. 4, 2016 for International Application No. PCT/CN2016/07354.
Li Renli, "Certificate No. (Jing) 075—Drug Structure-Activity Relationship", China Medical Science and Technology Press, Oct. 2003, ISBN7-5067-2773-0.
Full Examination Report No. 1 for standard patent application by the Australian Patent Office for AU 2016391377 dated Jan. 25, 2019.
1st Chinese Office Action (Chinese and English Translation) in CN 201680066535.6 before Feb. 2, 2019.
2nd Chinese Office Action (Chinese and English Translation) in CN 201680066535.6 after Feb. 2, 2019.
1st Office Action by the Canadian Patent Office in CA 3,013,514 dated Mar. 10, 2020.
2nd Office Action by the Canadian Patent Office CA 3,013,514 dated Mar. 10, 2020.
Office Action dated Mar. 20, 2020 in EP 1688753.7.
Extended European Search Report in EP 16888753.7 dated May 28, 2019.
1st Japanese Notice of Reasons for Rejection for JP P2018-541333 dated Jul. 9, 2019 (in Japanese and English Translation).
2nd Japanese Notice of Reasons for Rejection for JP P2018-541333 dated Mar. 18, 2020 (in Japanese and English Translation).
1st Korean Office Action in Korean 10-2018-7024712 dated Dec. 26, 2019 (Korean and English Translation).
Korean Notice of Final Rejection in Korean 10-2018-7024712 dated Dec. 26, 2019 (Korean and English Translation).
Taiwanese Office Action in TW 10620774810 prior to Aug. 13, 2020(Taiwanese and English Translation).
Opinions Relevant to Inventive Step in the Taiwanese Office Action (English Translation).
KR 2011-0084539 English Translation.
Constance King et al., "LY2606368 Causes Replication Catastrophe and Antitumor Effects through CHK1-Dependent Mechanisms", Mol. Cancer Ther., vol. 14, No. 9, pp. 2004-2013, Sep. 1, 2015 (Sep. 1, 2015).
Tao Chen, et al.: Targeting the S and G2 checkpoint to treat Cancer: Drug Discovery Today: vol. 17, Nos. 5/6: Mar. 2012: pp. 194-202.
James W Janetka, et al.: Inhibitors of checkpoint kinases: From discovery to the clinic Opinion in Drug Discovery & Development: 2007: vol. 10: No. 4: pp. 473-486: © The Thomson Corporation ISSN 1367-6733.

(Continued)

Primary Examiner — Alicia L Otton
(74) Attorney, Agent, or Firm — Ladas & Parry LLP

(57) ABSTRACT

The present invention provides compounds of formula (I) which are potent inhibitors of Chk1 and have the structural formula below:

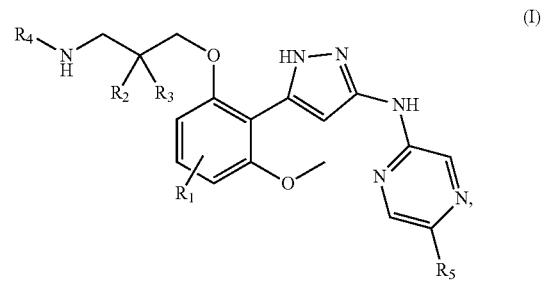

wherein $R_1$, $R_2$, $R_3$, $R_4$, and $R_5$ are as defined herein. Pharmaceutical compositions comprising the compounds, uses thereof and their preparation process are also provided.

34 Claims, 5 Drawing Sheets

(56) References Cited

OTHER PUBLICATIONS

Adil I. Daud, etal: Phase I Dose-Escalation Trial of Checkpoint Kinase 1 Inhibitor MK-8776 as Monotherapy and in Combination with Gemcitabine in Patients with Advanced Solid Tumors: Journal of Clinical Oncology: 2015: 33: pp. 1060-1066.
Toshihiko Doia, et al.: Phase I study of LY2603618, a CHK1 inhibitor, in combination with gemcitabine in Japanese patients with solid tumors: Anti-Cancer Drugs: 2015, vol. 26: No. 10: pp. 1043-1053.
Siang-Boon Koh, et al.: CHK1 Inhibition Synergizes with Gemcitabine Initially by Destabilizing the DNA Replication Apparatus: Cancer Research: vol. 75: No. 17: Sep. 1, 2015: pp. 3583-3595.
Meredith A. Morgan, et al.: Improving the Efficacy of Chemoradation with Targeted Agents: Cancer Discovery: Mar. 2014: 4: pp. 280-291.
Felix Dietlein, et al.: A Syngeristic Interaction between Chk1- and MK2 Inhibitors in KRAS-Mutant Cancer: Jul. 2, 2015: Cell 162: pp. 146-159.
Eric J. Brown, et al.: ATR disruption leads to chromosomal fragmentation and early Embryonic lethality: Genes & Development 14: pp. 397-402: 2000.
Qinghua Liu, et al.: Chk1 is an essential kinase that is regulated by Atr and required for the $G_2$/M DNA damage checkpoint: Genes & Development: 2000: 14: pp. 1448-1459.
Yohei Tominaga, et al.: Murine Wee1 Plays a Critical Role in a Cell Cycle Regulation and Pre-Implantation Stages of Embryonic Development: International Jounral of Biological Sciences: ISSN 1449-2288 www.biolsci.org 2006: vol. 2: No. 4: pp. 161-170.
Francesco Bertoni, et al.: CHK1 Frameshift Mutations in Genetically unstable Colorectal and Endometrial Caners: Genes, Chromosomes & Cancer: 26: pp. 176-180 1999.
Kriste A. Lewis, et al.: Heterozygous ATR Mutations in Mismatch Repair-Deficient Cancer Cells have Functional Significance: Cancer Res 2005: 65: pp. 7091-7095.
Israel Zighelboim et al.: ATR Mutation in Endometrioid Endometrial Cancer is Associated with Poor Clinical Outcomes: Journal Of Clinical Oncology: vol. 27: No. 19: Jul. 1, 2009; pp. 3091-3096.
Henriett Butz et al.: Down-Regulation of Wee1 Kinase by a Specific Subset of micro RNA in Human Sporadic Pituitary Adenomas: J Clin Endocrinol Metab: Oct. 2010: vol. 95: No. 10: pp. E181-E191.
Esmerina Tili, et al.: Mutator activity induced by microRNA-155 (mir-155) links inflammation and cancer: vol. 108: No. 12: Mar. 22, 2011: pp. 4908-4913.
Elizabeth Iorns, et al.: Integrated Functional, Gene Expression and Genomic Analysis for the Identification of Cancer Targets: vol. 4: Issue 4: Apr. 2009: e5120: pp. 1-20.
Shahryar E. Mir, et al.: In Silico Analysis of Kinase Expression Identifies WEE1 as a Gatekeeper against Mitotic Catastrophe in Glioblastoma: Cancer Cell. Sep. 14, 2010: vol. 18, No. 3: pp. 244-257.
Kristina A.Cole et al.: RNAi Screen of Protein Kinome identifies checkpoint kinase I (CHK1) as a Therapeutic target in Neuroblastoma: Feb. 22, 2011: vol. 108: No. 8: pp. 3336-3341.
Gry Irene Magnussen, et al.: High Expression of Wee1 Is Associated with Poor Disease-Free Survival in Malignant Melanoma: Potential for Targeted Therapy: Jun. 2012: vol. 7: Issue 6: e38254: pp. 1-8.
Rahul A. Parikh et al.: Upregulation of the ATR-CHECK1 Pathway in Oral Squamous Cell Carcinomas: Genes Chromosomes Cancer: Jan. 2014: vol. 53: No. 1: pp. 25-37.
Claus Storgaard Sørensen, et al.: Safeguarding genome integrity: the checkpoint kinases ATR, CHK1, and WEE1 restrain CDK activity during normal DNA replication: Nucleic Acids Research: 2012: vol. 40: No. 2: pp. 477-486.
Emilio Lecona, et al.: Replication stress and cancer: it takes two to tango: Exp Cell Res. Nov. 15, 2014; vol. 329: No. 1: pp. 26-34.
Andreas Höglund, et al.: Therapeutic Implications for the Induced levels of Chk1 in Myc-Expressing Cancer Cells: Clin Cancer Res: vol. 17: No. 22: Nov. 15, 2011: pp. 7067-7079.
Cynthia X. Ma, et al.: Targeting Chk1 in p53-deficient triple-negative breast cancer is therapeutically beneficial in human-in-mouse tumor models: J Clin Invest.: vol. 122: No. 4: Apr. 2012: pp. 1541-1552.

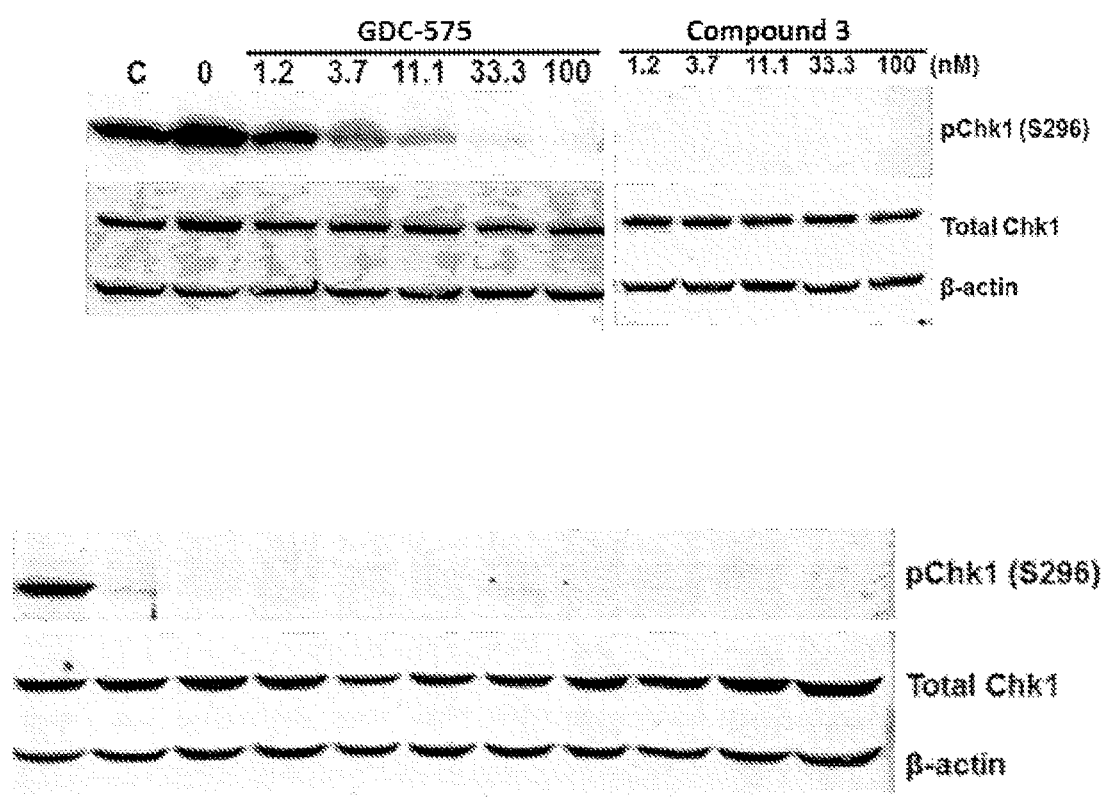
Figure 1. Western Blot Analysis for ChK1 phosphorylation by co-treatment with ChK1 inhibitors and SN-38 (200 nM)

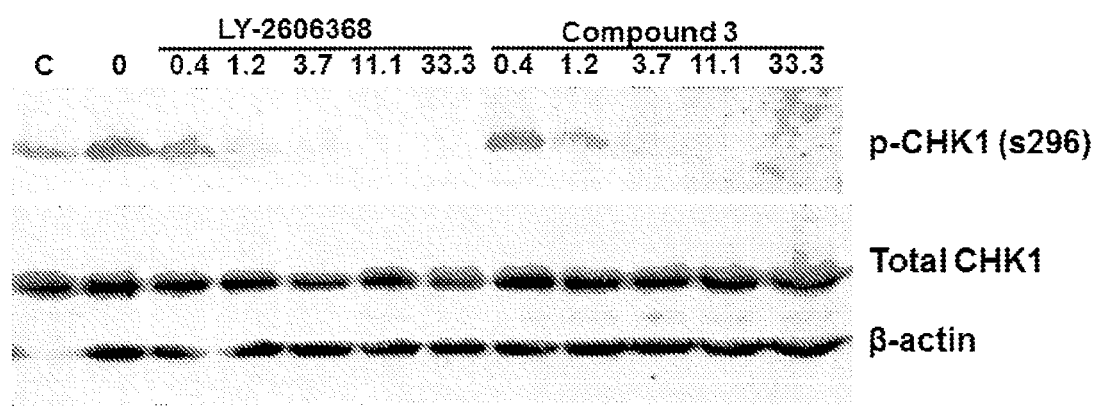
Figure 2. Western Blot Analysis for ChK1 phosphorylation by ChK1 inhibitor in HT-29 cells pretreated with SN-38

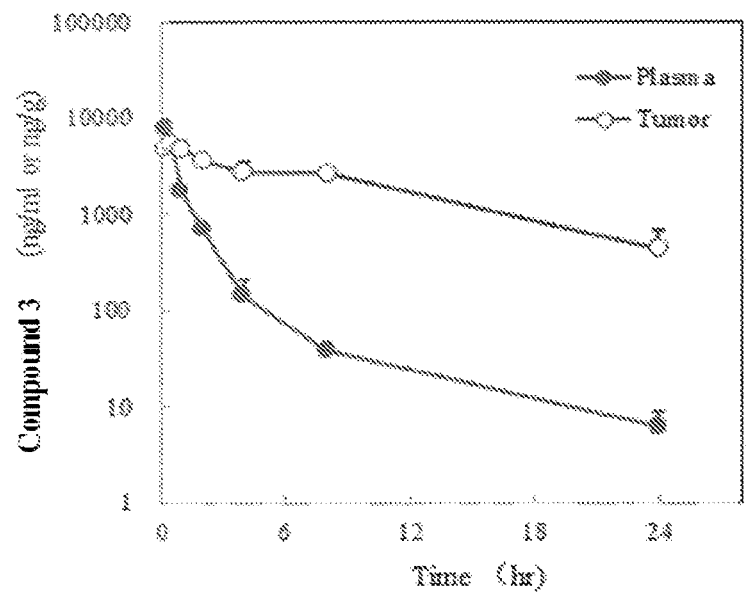
|  | Dose (iv) | T1/2 (elim.) | Cmax | AUC(0-t) | AUC(∞) | MRT | Vd | Vss | CL |
|---|---|---|---|---|---|---|---|---|---|
|  | mg/kg | hr | ng/ml | ng-hr/ml | ng-hr/ml | hr | L/kg | L/kg | L/hr/kg |
| Plasma | 40.0 | 6.1 | 14525 | 8556 | 8610 | 1.5 | 40.7 | 6.8 | 4.6 |
| Tumor | 40.0 | 14.0 | 11363 | 52324 | 56398 | 8.5 |  |  |  |
Figure 3. PK Study of Compound 3 in HT-29 Xenograft Mice

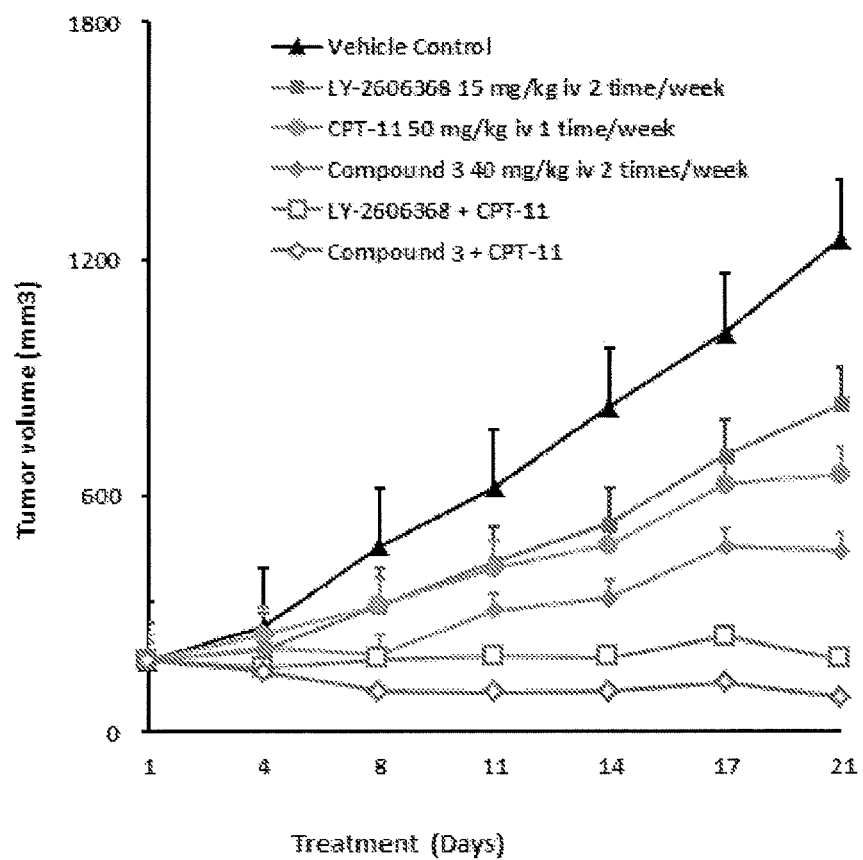
Figure 4. Tumor growth inhibition by combination of Compound 3 and CPT-11 in HT-29 Xenograft Model

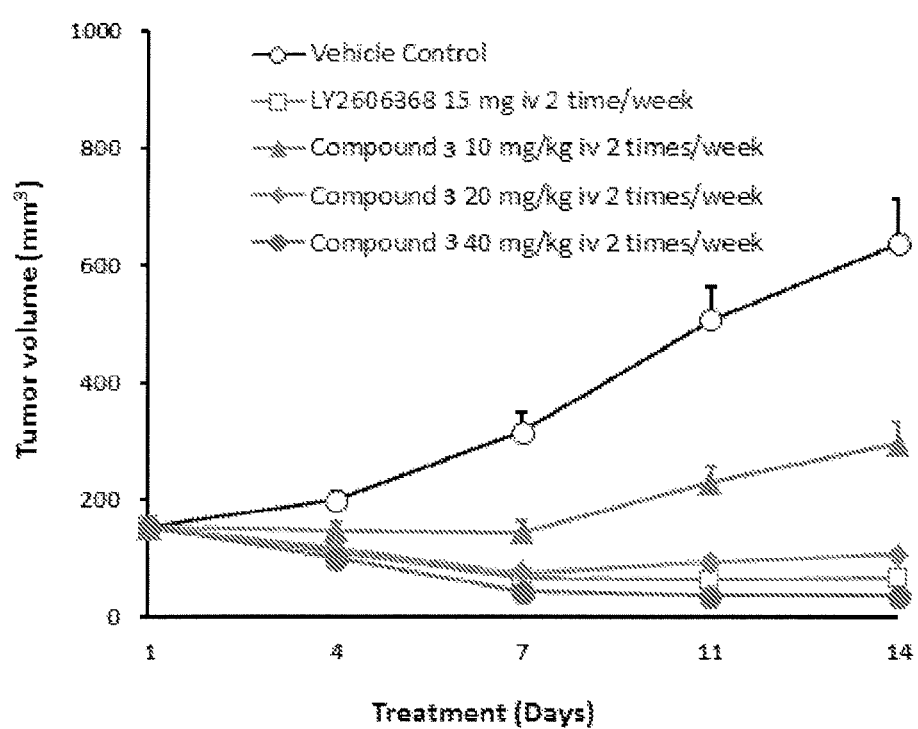
Figure 5. Dose-dependent tumor growth inhibition by Compound 3 in LoVo Xenograft Model

3,5-DISUBSTITUTED PYRAZOLES USEFUL AS CHECKPOINT KINASE 1 (CHK1) INHIBITORS, AND THEIR PREPARATIONS AND APPLICATIONS

FIELD OF THE APPLICATION

The present invention relates to compounds having a 3,5-disubstituted pyrazole core which are potent inhibitors of checkpoint kinase 1 (Chk1). More specifically, the present invention provides a compound of formula (I) or geometric isomers, enantiomers, distereomers, racemates, pharmaceutically acceptable salts, prodrugs, solvates, or hydrates thereof, a pharmaceutical composition comprising the compound, and a method of making the compound. The compound acts as a Chk1 inhibitor, and is useful in the treatment of cancers characterized by constitutive activation of Chk1 or high intrinsic deoxyribonucleic acid (DNA) damage or lesions in DNA replication. The present invention also relates to a method for treating cancers by using the compound.

BACKGROUND

DNA damage, occurring in all cells and organelles that contain DNA, can result from errors made during DNA replication as well as from agents that chemically modify or intercalate within the DNA structure. These DNA alternations activate DNA replication G1/S checkpoint or G2/M checkpoint, which inhibit cell cycle progression from G1 to S or from G2 to mitosis, respectively. The cell cycle arrest allows cells to repair damaged DNA in cancers treated with anticancer agents or ionizing radiation, thus preventing the transmission of genetic errors to daughter cells.

DNA damage repair and cell cycle control proteins have recently attracted attention as molecular drug targets for the treatment of cancers in combination with chemotherapy or ionizing radiations. A number of small molecular inhibitors of proteins involved in DNA repair and cell cycle control are currently being developed, including small molecular inhibitors of poly-adenosine diphosphate-ribose polymerase-1 (PARP-1), DNA-dependent protein kinase (DNA-PK), ataxia-telangiectasia-related (ATR) protein kinase and checkpoint kinase 1 (Chk1).

Chk1 is a conserved serine/threonine protein kinase. Activation of ATR phosphorylates Chk1, which deactivates Cdc25A and Cdc25C, leading to S and G2/M arrest, respectively (Chen T. et al., Drug Discov Today 17, 194-202, 2012). It has been observed that many tumors are deficient in G1 checkpoints, making them dependent on the S and G2 checkpoints to repair DNA damage and survive (Janetka J. W. et al., Opinion in Drug Discov Develop 10:473, 2007). The S and G2 checkpoints are regulated by Chk1. Therefore, Chk1 acts as a major player in the signal transduction pathway activated in response to DNA damage.

Inhibition of Chk 1 has been shown to abolish the S and G2 checkpoints, thereby impairing DNA repair, abrogating cell cycle arrest and resulting in increased tumor cell death even in the absence of DNA damage. Several Chk1 inhibitors have been advanced to clinical development. MK-8776 (Daud A. L. et al., J Clin Oncol 33:1060-1066, 2015). Chk1 inhibitors LY2603618 (Doi T. et al. Anticancer Drugs. 2015 Aug. 18. [Epub ahead of print]) and GDC-0425 (AACR 2015, Philadelphia, Pa.) were tolerated as monotherapy and in combination with gemcitabine. Early evidence of clinical efficacy was observed. A phase II study of LY2606368 in patients with breast, ovarian or prostate cancer is in progress (ClinicalTrials.gov Identifier: NCT02203513).

Chk1 inhibitors have been developed for use in combination with anti-metabolites and DNA-damaging agents (e.g., gemcitabine, irinotecan, topotecan, cisplatin, ionizing radiation and docetaxel) that cause S and G2 arrest, to increase the sensitivity of the treatment (Koh S-B. et al. Cancer Res 75:3583-3595, 2015; Morgan M. A. et al. Cancer Discov 4:280-291, 2014.).

KRAS is one of the most frequently mutated oncogenes in human cancer, and no clinically effective treatment has yet been developed for KRAS-mutant tumors. KRAS-mutant cancer displays increased Chk1 and MK2 activity. Simultaneous targeting of Chk1 and MK2 leads to mitotic catastrophe in KRAS-mutant cells and induces apoptotic cell death in KRAS- or BRAF-mutant tumor cells directly isolated from patients. Combination of a Chk1 inhibitor with an MK2 inhibitor could provide a therapeutic strategy for the treatment of KRAS- or BRAF-driven cancers (Dietlein F. et al., Cell 162: 146-159, 2015).

ATR, Chk1, and WEE1 are all essential proteins required for embryonic development in mice (Brown and Baltimore, 2000; Liu et al., 2000; Tominaga et al., 2006). Consistent with an essential role, homozygous inactivating mutations of the genes encoding these checkpoint kinases have not been observed in cancer. However, a small subset of human tumors shows heterozygous mutations in ATR or Chk1 (Bertoni et al., 1999; Lewis et al., 2005; Zighelboim et al., 2009), resulting in reduced protein expression. To our knowledge mutations in WEE1 have not been reported. However, WEE1 may be downregulated through other mechanisms such as cancer-associated expression of microRNAs (Butz et al., 2010; Tili et al., 2011). It is possible that cancer cells with inherent reduced expression of ATR, Chk1, or WEE1 may respond to low concentrations of checkpoint kinase inhibitors, whereby normal cells could be spared.

On the other hand, ATR, Chk1, and WEE1 are also overexpressed in a subset of human cancers (Iorns et al., 2009; Mir et al., 2010; Cole et al., 2011; Magnussen et al., 2012; Parikh et al., 2014). In some cases, the checkpoint kinases may be upregulated as part of a cellular response to cope with elevated replication stress (Sorensen and Syljuåsen, 2012; Lecona and Fernandez-Capetillo, 2014). For instance, Myc amplification has been linked with elevated Chk1 levels and increased sensitivity to Chk1 inhibitors (Cole et al., 2011; Hoglund et al., 2011). Possibly, such cells will therefore depend on the high levels of ATR, Chk1, or WEE1 to survive. Inhibitors of ATR, Chk1, or WEE1 may thus potentially be more toxic to cancer cells inherently expressing high levels of these kinases. Taken together, this creates a complex picture where either abnormal low expression, or high expression, of ATR, Chk1, or WEE1 in cancer cells may potentially cause increased sensitivity to inhibitors of these checkpoint kinases. It is very convincing that CHK1 and WEE1 inhibition combine synergistically to enhance therapeutic efficacy in certain type of human cancers.

The protein p53 is a tumor suppressor protein. Upon DNA damage p53 is stabilized and activated to induce a p53-dependent G1 arrest, leading to apoptosis or DNA repair. Over half of all cancers are functionally defective for p53. These p53-deficient cells fail to arrest at the G1/S checkpoint, making them more reliant on the G2/M checkpoint for viability and replication. Chk1 inhibitors, blocking the function of G2/M checkpoint, have more pronounced potentiating effects in some p53-deficient tumors, such as in the colon, breast, and prostate and those associated with leukemia (Chen T et al., Drug Discov Today 17, 194-202, 2012; Ma C. X. et al., J Clin Invest. 122:1541-1552, 2012).

Chk1 inhibitors have been disclosed, including, for example, aryl- and heteroaryl-substituted urea compounds described in WO 2006/021002 A3, WO 2006/014359 A3, and WO 02/070494 A1; aminopyrazole compounds described in WO 2012/064548 A1 and WO 2010/077758 A1; substituted urea compounds described in WO 2006/105262 A1; thiophene and thiazole derivatives described in EP 2 305 671 A1; and carbamate compounds described on US 2005/0148643 A1.

However, there is still a need for new compounds that are potent inhibitors of Chk1 and beneficial for the treatment of cancers. The present invention addresses this need.

SUMMARY OF THE INVENTION

The present invention relates to Chk1 inhibitors having a 3,5-disubstituted pyrazole core.

One aspect of the present invention is to provide a compound of formula (I):

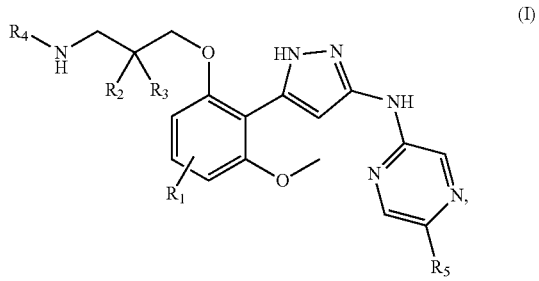

wherein R, $R_1$, $R_2$, $R_3$, $R_4$ and $R_5$ are as defined in the specification, or a pharmaceutically acceptable salt, geometric isomer, enantiomer, distereomer, racemate, prodrug, solvate, or hydrate thereof.

Another aspect of the invention is to provide a pharmaceutical composition comprising a therapeutically effective amount of a compound of formula (I), or a pharmaceutically acceptable salt, geometric isomer, enantiomer, distereomer, racemate, prodrug, solvate, or hydrate thereof, and one or more pharmaceutically acceptable carriers or excipients therefor. The pharmaceutical composition of the present invention is effective in the inhibition of Chk1, and thus is useful in treating cancer.

Another aspect of the invention is to provide the use of a compound of formula (I), or a pharmaceutically acceptable salt, geometric isomer, enantiomer, distereomer, racemate, prodrug, solvate, or hydrate thereof, in the manufacture of a medicament for inhibiting Chk1, which is useful in treating cancer.

Another aspect of the invention is to provide a method for treating cancer comprising administering a therapeutically effective amount of a compound of formula (I) or a pharmaceutically acceptable salt, geometric isomer, enantiomer, distereomer, racemate, prodrug, solvate, or hydrate thereof to a subject in need so that the growth of the cancer in the subject is inhibited. The compound of formula (I) can be used alone or in combination with another therapeutic agent.

Another aspect of the invention is to provide a method for preparing a compound of formula (I), or a pharmaceutically acceptable salt, geometric isomer, enantiomer, distereomer, racemate, prodrug, solvate, or hydrate thereof.

These and other aspects of the present invention will become apparent from the following detailed description.

BRIEF DESCRIPTION OF THE DRAWINGS

FIG. 1 shows the Western Blot Analysis for ChK1 phosphorylation by co-treatment with ChK1 inhibitors and SN-38 (200 nM).

FIG. 2 shows the Western Blot Analysis for ChK1 phosphorylation by ChK1 inhibitor in HT-29 cells pretreated with SN-38.

FIG. 3 shows the PK Study of Compound 3 in HT-29 Xenograft Mice.

FIG. 4 shows the tumor growth inhibition by combination of Compound 3 and CPT-11 in HT-29 Xenograft Model.

FIG. 5 shows the dose-dependent tumor growth inhibition by Compound 3 in LoVo Xenograft Model.

DETAILED DESCRIPTION

The present invention can be understood more readily by reference to the following detailed description of various embodiments of the invention, the examples, and the tables with their relevant descriptions. Unless otherwise defined, all terms (including technical and scientific terms) used herein have the same meaning as commonly understood by one of ordinary skill in the art to which this invention belongs. It will be further understood that terms such as those defined in commonly used dictionaries should be interpreted consistently with their meaning in the context of the relevant art and will not be interpreted in an idealized or overly formal sense unless expressly so defined herein. It is also to be understood that the terminology used herein is for the purpose of describing particular embodiments only and is not intended to be limiting.

Compounds

The compounds of the present invention have a structure of formula (I):

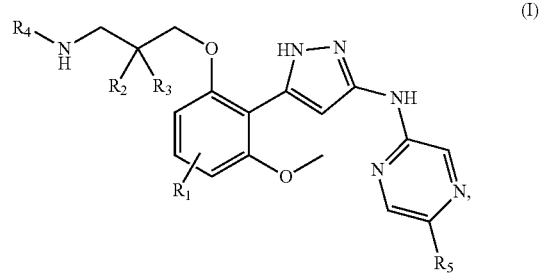

wherein:

$R_1$ is halogen, unsubstituted or substituted alkyl, unsubstituted or substituted alkenyl, unsubstituted or substituted alkynyl, unsubstituted or substituted cycloalkyl, unsubstituted or substituted alkoxy, unsubstituted or substituted aryl, —$NO_2$, —OH, —C(O)R, —C(O)OR, —C(O)N(R')(R''), or —N(R')(R'');

$R_2$ and $R_3$ are each independently —H, halogen, unsubstituted or substituted alkyl, unsubstituted or substituted cycloalkyl, unsubstituted or substituted alkoxy, —$NO_2$, —OH, or —N(R')(R''), or $R_2$ and $R_3$ together with the carbon atom to which they are attached form an unsubstituted or substituted carbon cyclic or heterocyclic ring;

R₄ is —H, unsubstituted or substituted alkyl, unsubstituted or substituted cycloalkyl, unsubstituted or substituted alkoxy, unsubstituted or substituted aryl, —OH, —C(O)R, —C(O)OR, —C(O)N(R')(R"), or —N(R')(R");

R₅ is —CN, halogen, unsubstituted or substituted alkyl, unsubstituted or substituted alkenyl, unsubstituted or substituted alkynyl, unsubstituted or substituted cycloalkyl, unsubstituted or substituted alkoxy, —NO₂, —OH, or —N(R')(R");

R is unsubstituted or substituted alkyl; and

R' and R" are each independently —H or unsubstituted or substituted alkyl, or a pharmaceutically acceptable salt, geometric isomer, enantiomer, distereomer, racemate, prodrug, solvate, or hydrate thereof.

In an embodiment of the compound of formula (I), R₁ is halogen, unsubstituted or substituted alkyl, unsubstituted or substituted alkenyl, unsubstituted or substituted alkynyl, unsubstituted or substituted alkoxy, —NO₂, —OH, —C(O)OR, —C(O)N(R')(R"), or —N(R')(R"), wherein R is unsubstituted or substituted alkyl; and R₂, R₃, R₄, R₅, R, R' and R" are as defined above. Preferably, R₁ is halogen, unsubstituted alkyl, unsubstituted alkoxy, —OH, —CF₃, or hydroxyalkyl. Even more preferably, R₁ is —F, —Cl, —Br, methyl, ethyl, propyl, isopropyl, methoxy, ethoxy, isopropoxy, —OH, —CF₃, or hydroxymethyl.

In another embodiment of the compound of formula (I), R₂ and R₃ are each independently —H, —OH, halogen, unsubstituted or substituted alkyl, or —N(R')(R"), or R₂ and R₃ together with the carbon atom to which they are attached form an unsubstituted or substituted carbon cyclic or heterocyclic ring; and R₁, R₄, R₅, R, R' and R" are as defined above. Preferably, R₂ and R₃ are each independently —H, —OH, halogen, unsubstituted alkyl, or hydroxyalkyl, or R₂ and R₃ together with the carbon atom to which they are attached form an unsubstituted carbon cyclic ring or heterocyclic ring. More preferably, R₂ and R₃ are each independently —H, —OH, —F, —Cl, methyl, ethyl, or hydroxymethyl, or R₂ and R₃ together with the carbon atom to which they are attached form cyclopropyl, cyclobutyl, cyclopentyl, oxirane, aziridine, or azetidine.

In another embodiment of the compound of formula (I), R₄ is —H, unsubstituted or substituted alkyl, —C(O)OR, or —C(O)R; and R₁, R₂, R₃, R₅, R, R' and R" are as defined above. Preferably, R₄ is —H, methyl, ethyl, propyl, acetyl, aminoacetyl, methoxycarbonyl, 1-(1-oxo-2-methylpropoxy)ethoxycarbonyl, or ethoxycarbonyl.

In another embodiment of the compound of formula (I), R₅ is —CN, halogen, unsubstituted or substituted alkyl, unsubstituted or substituted alkenyl, or unsubstituted or substituted alkynyl; and R₁, R₂, R₃, R₄, R, R' and R" are as defined above. Preferably, R₅ is —CN, halogen, or unsubstituted alkyl. More preferably, R₅ is —CN, —F, —Cl, —Br, methyl, ethyl, propyl, or isopropyl.

In a further embodiment, the compound of the present invention is a compound of formula (II):

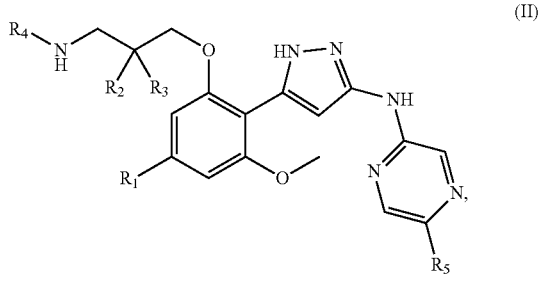

(II)

wherein:

R₁ is —F, —Cl, —Br, methyl, methoxy;

R₂ and R₃ are each independently —H or —OH, or R₂ and R₃ together with the carbon atom to which they are attached form cyclopropyl;

R₄ is —H, methyl, aminoacetyl, 1-(1-oxo-2-methylpropoxy)ethoxycarbonyl, or ethoxycarbonyl; and R₅ is —CN, methyl, or —Cl, or a pharmaceutically acceptable salt, geometric isomer, enantiomer, distereomer, racemate, prodrug, solvate, or hydrate thereof.

In yet another preferred embodiment, the present invention provides a compound selected from the group consisting of:

5-(5-(2-(3-aminopropoxy)-3-fluoro-6-methoxyphenyl)-1H-pyrazol-3-ylamino)pyrazine-2-carbonitrile, 5-((5-(6-(3-aminopropoxy)-3-fluoro-2-methoxyphenyl)-1H-pyrazol-3-yl)amino)pyrazine-2-carbonitrile;

5-(5-(2-(3-aminopropoxy)-4-fluoro-6-methoxyphenyl)-1H-pyrazol-3-ylamino)pyrazine-2-carbonitrile;

5-(5-(2-(3-aminopropoxy)-4-chloro-6-methoxyphenyl)-1H-pyrazol-3-ylamino)pyrazine-2-carbonitrile;

5-(5-(2-(3-aminopropoxy)-4-bromo-6-methoxyphenyl)-1H-pyrazol-3-ylamino)pyrazine-2-carbonitrile;

5-(5-(2-(3-aminopropoxy)-6-methoxy-4-methylphenyl)-1H-pyrazol-3-ylamino)pyrazine-2-carbonitrile;

5-(5-(2-(3-aminopropoxy)-4,6-dimethoxyphenyl)-1H-pyrazol-3-ylamino)pyrazine-2-carbonitrile;

5-(5-(2-(3-methyl aminopropoxy)-4-fluoro-6-methoxyphenyl)-1H-pyrazol-3-ylamino) pyrazine-2-carbonitrile;

5-(5-(2-(3-methylaminopropoxy)-4-chloro-6-methoxyphenyl)-1H-pyrazol-3-ylamino) pyrazine-2-carbonitrile;

5-(5-(2-(3-methylaminopropoxy)-4-bromo-6-methoxyphenyl)-1H-pyrazol-3-ylamino) pyrazine-2-carbonitrile;

5-(5-(2-(3-methylaminopropoxy)-4-methyl-6-methoxyphenyl)-1H-pyrazol-3-ylamino) pyrazine-2-carbonitrile;

5-(5-(2-(3-methylaminopropoxy)-4,6-dimethoxyphenyl)-1H-pyrazol-3-ylamino) pyrazine-2-carbonitrile;

5-(5-(2-((1-(aminomethyl)cyclopropyl)methoxy)-4-fluoro-6-methoxyphenyl)-1H-pyrazol-3-ylamino)pyrazine-2-carbonitrile;

5-(5-(2-((1-(aminomethyl)cyclopropyl)methoxy)-4-chloro-6-methoxyphenyl)-1H-pyrazol-3-ylamino)pyrazine-2-carbonitrile;

5-(5-(2-((1-(aminomethyl)cyclopropyl)methoxy)-4-bromo-6-methoxyphenyl)-1H-pyrazol-3-ylamino)pyrazine-2-carbonitrile;

5-(5-(2-((1-(aminomethyl)cyclopropyl)methoxy)-6-methoxy-4-methylphenyl)-1H-pyrazol-3-ylamino)pyrazine-2-carbonitrile;

5-(5-(2-((1-(aminomethyl)cyclopropyl)methoxy)-4,6-dimethoxyphenyl)-1H-pyrazol-3-ylamino)pyrazine-2-carbonitrile;

5-(5-(3-fluoro-6-methoxy-2-((1-((methylamino)methyl)cyclopropyl)methoxy)phenyl)-1H-pyrazol-3-ylamino)pyrazine-2-carbonitrile;

5-((5-(3-fluoro-2-methoxy-6-((1-((methylamino)methyl)cyclopropyl)methoxy)phenyl)-1H-pyrazol-3-yl)amino) pyrazine-2-carbonitrile;

5-(5-(4-fluoro-2-methoxy-6-((1-((methylamino)methyl)cyclopropyl)methoxy)phenyl)-1H-pyrazol-3-ylamino)pyrazine-2-carbonitrile;

5-((5-(4-chloro-2-methoxy-6-((1-((methylamino)methyl)cyclopropyl)methoxy)phenyl)-1H-pyrazol-3-yl)amino) pyrazine-2-carbonitrile;

5-((5-(4-bromo-2-methoxy-6-((1-((methylamino)methyl) cyclopropyl)methoxy)phenyl)-1H-pyrazol-3-yl)amino) pyrazine-2-carbonitrile;

5-((5-(2-methoxy-4-methyl-6-((1-((methylamino)methyl) cyclopropyl)methoxy)phenyl)-1H-pyrazol-3-yl)amino) pyrazine-2-carbonitrile;

5-((5-(2,4-dimethoxy-6-((1-((methylamino)methyl)cyclopropyl)methoxy)phenyl)-1H-pyrazol-3-yl)amino)pyrazine-2-carbonitrile;

5-(5-(2-(2-hydroxy-3-aminopropoxy)-4-fluoro-6-methoxyphenyl)-1H-pyrazol-3-ylamino) pyrazine-2-carbonitrile;

5-(5-(2-(2-hydroxy-3-aminopropoxy)-4-methyl-6-methoxyphenyl)-1H-pyrazol-3-ylamino) pyrazine-2-carbonitrile;

5-(5-(2-(2-hydroxy-3-aminopropoxy)-4,6-dimethoxyphenyl)-1H-pyrazol-3-ylamino) pyrazine-2-carbonitrile;

2-methyl-5-(5-(2-(3-aminopropoxy)-4-fluoro-6-methoxyphenyl)-1H-pyrazol-3-ylamino) pyrazine;

2-chloro-5-(5-(2-(3-aminopropoxy)-4-fluoro-6-methoxyphenyl)-1H-pyrazol-3-ylamino) pyrazine;

2-methyl-5-(5-(2-(3-methylaminopropoxy)-4-fluoro-6-methoxyphenyl)-1H-pyrazol-3-yl amino)pyrazine;

2-chloro-5-(5-(2-(3-methyl aminopropoxy)-4-fluoro-6-methoxyphenyl)-1H-pyrazol-3-yl amino)pyrazine;

2-methyl-5-(5-(2-((1-(aminomethyl)cyclopropyl)methoxy)-4-fluoro-6-methoxyphenyl)-1H-pyrazol-3-ylamino)pyrazine;

2-chloro-5-(5-(2-((1-(aminomethyl)cyclopropyl)methoxy)-4-fluoro-6-methoxyphenyl)-1H-pyrazol-3-ylamino)pyrazine;

2-methyl-5-(5-(2-((1-(aminomethyl)cyclopropyl)methoxy)-4-fluoro-6-methoxyphenyl)-1H-pyrazol-3-ylamino)pyrazine;

2-chloro-5-(5-(2-((1-(aminomethyl)cyclopropyl)methoxy)-4-fluoro-6-methoxyphenyl)-1H-pyrazol-3-ylamino)pyrazine;

2-methyl-5-(5-(2-(2-hydroxy-3-aminopropoxy)-4-fluoro-6-methoxyphenyl)-1H-pyrazol-3-yl amino)pyrazine;

2-chloro-5-(5-(2-(2-hydroxy-3-aminopropoxy)-4-fluoro-6-methoxyphenyl)-1H-pyrazol-3-yl amino)pyrazine;

ethyl 3-(2-(3-(5-cyanopyrazin-2-ylamino)-1H-pyrazol-5-yl)-5-fluoro-3-methoxyphenoxy) propylcarbamate;

2-amino-N-(3-(2-(3-((5-cyanopyrazin-2-yl)amino)-1H-pyrazol-5-yl)-5-fluoro-3-methoxy phenoxy)propyl)acetamide; or 1-(((3-(2-(3-((5-cyanopyrazin-2-yl)amino)-1H-pyrazol-5-yl)-5-fluoro-3-methoxyphenoxy) propyl)carbamoyl)oxy) ethyl isobutyrate, or a pharmaceutically acceptable salt, geometric isomer, enantiomer, distereomer, racemate, prodrug, solvate, or hydrate thereof.

In still another preferred embodiment, the present invention provides compounds selected from the group consisting of:

5-(5-(2-(3-aminopropoxy)-3-fluoro-6-methoxyphenyl)-1H-pyrazol-3-ylamino)pyrazine-2-carbonitrile;

5-((5-(6-(3-aminopropoxy)-3-fluoro-2-methoxyphenyl)-1H-pyrazol-3-yl)amino)pyrazine-2-carbonitrile;

5-(5-(2-(3-aminopropoxy)-4-fluoro-6-methoxyphenyl)-1H-pyrazol-3-ylamino)pyrazine-2-carbonitrile;

5-(5-(2-(3-aminopropoxy)-4-chloro-6-methoxyphenyl)-1H-pyrazol-3-ylamino)pyrazine-2-carbonitrile;

5-(5-(2-(3-aminopropoxy)-4-bromo-6-methoxyphenyl)-1H-pyrazol-3-ylamino)pyrazine-2-carbonitrile;

5-(5-(2-(3-aminopropoxy)-6-methoxy-4-methylphenyl)-1H-pyrazol-3-ylamino)pyrazine-2-carbonitrile;

5-(5-(2-(3-aminopropoxy)-4,6-dimethoxyphenyl)-1H-pyrazol-3-ylamino)pyrazine-2-carbonitrile;

5-(5-(2-((1-(aminomethyl)cyclopropyl)methoxy)-4-fluoro-6-methoxyphenyl)-1H-pyrazol-3-ylamino)pyrazine-2-carbonitrile;

5-(5-(2-((1-(aminomethyl)cyclopropyl)methoxy)-4-chloro-6-methoxyphenyl)-1H-pyrazol-3-ylamino)pyrazine-2-carbonitrile;

5-(5-(2-((1-(aminomethyl)cyclopropyl)methoxy)-4-bromo-6-methoxyphenyl)-1H-pyrazol-3-ylamino)pyrazine-2-carbonitrile;

5-(5-(2-((1-(aminomethyl)cyclopropyl)methoxy)-6-methoxy-4-methylphenyl)-1H-pyrazol-3-ylamino)pyrazine-2-carbonitrile;

5-(5-(2-((1-(aminomethyl)cyclopropyl)methoxy)-4,6-dimethoxyphenyl)-1H-pyrazol-3-yl amino)pyrazine-2-carbonitrile;

5-(5-(3-fluoro-6-methoxy-2-((1-((methylamino)methyl)cyclopropyl)methoxy)phenyl)-1H-pyrazol-3-ylamino)pyrazine-2-carbonitrile, 5-((5-(3-fluoro-2-methoxy-6-((1-((methylamino)methyl)cyclopropyl)methoxy)phenyl)-1H-pyrazol-3-yl)amino) pyrazine-2-carbonitrile;

5-(5-(4-fluoro-2-methoxy-6-((1-((methylamino)methyl)cyclopropyl)methoxy)phenyl)-1H-pyrazol-3-ylamino)pyrazine-2-carbonitrile; and ethyl 3-(2-(3-(5-cyanopyrazin-2-ylamino)-1H-pyrazol-5-yl)-5-fluoro-3-methoxyphenoxy) propylcarbamate, or a pharmaceutically acceptable salt, geometric isomer, enantiomer, distereomer, racemate, prodrug, solvate, or hydrate thereof.

Definitions

The definitions set forth in this section are intended to clarify terms used throughout this application. In this section, the definition applies to compounds of formulae (I) and (II) unless otherwise stated. The term "herein" means the entire application.

It must be noted that, as used herein, the singular forms "a," "an" and "the" include plural referents unless the context clearly dictates otherwise. Thus, unless otherwise required by context, singular terms shall include the plural and plural terms shall include the singular.

Often, ranges are expressed herein as from "about" one particular value and/or to "about" another particular value. When such a range is expressed, an embodiment includes the range from the one particular value and/or to the other particular value. Similarly, when values are expressed as approximations, by use of the word "about," it will be understood that the particular value forms another embodiment. It will be further understood that the endpoints of each of the ranges are significant both in relation to and independently of the other endpoint. As used herein, the term "about" refers to ±20%, preferably ±10%, and even more preferably ±5%.

As used herein, the phrase "unsubstituted or substituted" means that substitution is optional. In the event a substitution is desired then such substitution means that any number of hydrogens on the designated atom is replaced with a selection from the indicated group, provided that the normal valence of the designated atom is not exceeded, and that the substitution results in a stable compound. For example, when a substituent is keto (i.e., =O), then 2 hydrogens on the atom are replaced. Examples of substituents for a "substituted" group are those found in the exemplary compounds and embodiments disclosed herein and can include, for example, halogen, —OR, —CF$_3$, —CN, —NO$_2$, alkyl, alkenyl, alkynyl, cycloalkyl, alkoxy, haloalkyl, alkylamino, aminoalkyl, dialkylamino, hydroxylalkyl, alkoxyalkyl, hydroxyalkoxy, alkoxyalkoxy, aminoalkoxy, alkylaminoalkoxy, alkylaminoalkyl, and aryl, and the like.

The term "hydrocarbon" used herein refers to any structure comprising only carbon and hydrogen atoms up to 12 carbon atoms.

The term "hydrocarbon radical" or "hydrocarbyl" used herein refers to any structure resulting from removing one or more hydrogens from a hydrocarbon.

As used herein, the term "halogen" includes fluorine, chlorine, bromine and iodine. "Halo," used as a prefix of a group, means one or more hydrogens on the group are replaced with one or more halogens.

The term "hydroxy" is defined as —OH.

The term "alkyl" used herein refers to a monovalent, saturated, straight or branched hydrocarbon radical containing 1 to 12 carbon atoms. Preferably, the alkyl is a $C_1$-$C_8$ alkyl group. More preferably, the alkyl is a $C_1$-$C_6$ alkyl group. The alkyl can be unsubstituted or substituted with one or more substituents. Examples of a $C_1$-$C_6$ alkyl group include, but are not limited to, methyl, ethyl, n-propyl, isopropyl, n-butyl, isobutyl, sec-butyl, t-butyl, pentyl (including all isomeric forms), and hexyl (including all isomeric forms), heptyl (including all isomeric forms), octyl (including all isomeric forms) and the like.

The term "alkenyl" used herein refers to an unsaturated, straight or branched chain hydrocarbon radical having at least one carbon-carbon double bond and comprising 2 to 12 carbon atoms. Preferably, the alkenyl is a $C_2$-$C_8$ alkenyl group. More preferably, the alkenyl is a $C_2$-$C_6$ alkenyl group. Examples of alkenyl radicals include, but are not limited to, ethenyl, propenyl, butenyl, 1,4-butadienyl and the like.

The term "alkynyl" used herein refers to an unsaturated straight or branched chain hydrocarbon radical having at least one carbon-carbon triple bond and comprising 2 to 12 carbon atoms. Preferably, the alkynyl is a $C_2$-$C_8$ alkynyl group. More preferably, the alkynyl is a $C_2$-$C_6$ alkynyl group. Examples of alkynyl radicals include, but are not limited to, ethynyl, propynyl, butynyl and the like.

The term "amino" refers to the —$NH_2$ group. "Amino," used as a prefix or suffix of a group, means one or more hydrogens on the group are replaced with one or more amino groups.

The term "alkoxy," used alone or as a suffix or prefix, refers to radicals of the general formula —O-(alkyl), wherein alkyl is defined above. Exemplary alkoxy includes, but is not limited to, methoxy, ethoxy, n-propoxy, isopropoxy, n-butoxy, iso-butoxy, sec-butoxy, tert-butoxy, and the like.

An "alkoxyalkyl" group is represented by-(alkyl)-O-(alkyl), wherein alkyl is defined above.

The term "cycloalkyl" used herein refers to a saturated, monovalent hydrocarbon radical having cyclic configurations, including monocyclic, bicyclic, tricyclic, and higher multicyclic alkyl radicals (and, when multicyclic, including fused and bridged bicyclic and spirocyclic moieties) wherein each cyclic moiety has from 3 to 12 carbon atoms. Preferably, the cycloalkyl has from 3 to 8 carbon atoms. More preferably, the cycloalkyl has from 3 to 6 carbon atoms. When cycloalkyl contains more than one ring, the rings may be fused or unfused and include bicyclo radicals. Fused rings generally refer to at least two rings sharing two atoms therebetween. Such cycloalkyl groups include, by way of example, single ring structures such as cyclopropyl, cyclobutyl, cyclopentyl, cyclohexyl, cycloheptyl, cyclooctyl, 1-methylcyclopropyl, 2-methylcyclopentyl, 2-methylcyclooctyl, and the like, or multiple or bridged ring structures such as adamantyl and the like.

The term "hydroxyalkyl" refers to an alkyl group as described above substituted with one or more hydroxy groups.

The term "hydroxyalkoxy" refers to an alkoxy group as described above substituted with one or more hydroxy groups.

The term "aryl" used herein refers to a hydrocarbon radical having one or more polyunsaturated carbon rings and a conjugated pi electron system and comprising from 6 to 14 carbon atoms, wherein the radical is located on a carbon of the aromatic ring. In some embodiments, the aryl group contains from 6 to 12 carbon atoms, preferably 6 to 10 carbon atoms, in the ring portions of the groups. Exemplary aryl includes, but is not limited to, phenyl, biphenyl, naphthyl, indenyl and the like.

The term "one or more" used herein refers to one to ten, preferably, one, two, three, or four.

The compounds of the invention can exist as pharmaceutically acceptable salts. As used herein, "pharmaceutically acceptable salts" refer to derivatives of the disclosed compounds wherein the parent compound is modified by making pharmaceutically acceptable acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Nonlimiting examples of salts of compounds of the invention include, but are not limited to, hydrochloride, hydrobromide, hydroiodide, sulfate, bisulfate, 2-hydroxyethanesulfonate, phosphate, hydrogen phosphate, acetate, adipate, alginate, aspartate, benzoate, butyrate, camphorate, camphorsulfonate, citrate, digluconate, glycerolphosphate, hemisulfate, heptanoate, hexanoate, formate, succinate, malonate, fumarate, maleate, methanesulfonate, mesitylenesulfonate, naphthylenesulfonate, nicotinate, oxalate, pamoate, pectinate, persulfate, 3-phenylpropionate, picrate, pivalate, propionate, trichloroacetate, trifluoroacetate, glutamate, bicarbonate, undecanoate, lactate, citrate, tartrate, gluconate, benzene sulphonate, and p-toluenesulphonate salts.

As used herein, "prodrugs" are intended to include any covalently bonded carriers that release the active parent drug according to formula (I) through in vivo physiological action, such as hydrolysis, metabolism and the like, when such prodrug is administered to a subject. The suitability and techniques involved in making and using prodrugs are well known by a person of ordinary skill in the art. Prodrugs of the compounds of formula (I) (parent compounds) can be prepared by modifying functional groups present in the compounds in such a way that the modifications are cleaved, either in routine manipulation or in vivo, to the parent compounds. "Prodrugs" include the compounds of formula (I) wherein a hydroxy, amino, or sulfhydryl group is bonded to any group that, when the prodrugs are administered to a subject, cleaves to form a free hydroxyl, free amino, or free sulfhydryl group, respectively. Examples of prodrugs include, but are not limited to, derivatives and metabolites of the compounds of formula (I) that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. In certain embodiments, prodrugs of the compounds of formula (I) with carboxyl functional groups are the lower alkyl (e.g., $C_1$-$C_6$) esters of the carboxylic acid. The carboxylate esters are conveniently formed by esterifying any of the carboxylic acid moieties present on the molecule.

The compounds of the invention can exist as solvates. As used herein and unless otherwise indicated, the term "solvate" means a compound of formula (I), or a pharmaceutically acceptable salt thereof, that further includes a stoichiometric or non-stoichiometric amount of a solvent bound by non-covalent intermolecular forces. If the solvent is water, the solvate may be conveniently referred to as a "hydrate," for example, a hemi-hydrate, a mono-hydrate, a sesqui-hydrate, a di-hydrate, a tri-hydrate, etc.

The compounds of the present invention may exist in one or more particular geometric, optical, enantiomeric, diasteriomeric, epimeric, atropic, stereoisomeric, tautomeric, conformational, or anomeric forms, including but not limited to cis- and trans-forms; E- and Z-forms; c-, t-, and r-forms; endo- and exo-forms; R-, S-, and meso-forms; D- and L-forms; d- and I-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers."

As used herein, the term "enantiomers" refers to a pair of stereoisomers that are non-superimposable mirror images of each other. A 1:1 mixture of a pair of enantiomers is a racemic mixture. The term "enantiomers" is used to designate a racemic mixture where appropriate. "Diastereoisomers" are stereoisomers that have at least two asymmetric atoms, but which are not mirror-images of each other. The absolute stereochemistry may be specified according to the Cahn-Ingold-Prelog R-S system. When a compound is a pure enantiomer, the stereochemistry at each chiral carbon may be specified by either R or S. Resolved compounds can be designated (+) or (−) depending on the direction (dextro- or levorotatory) which they rotate plane polarized light at the wavelength of the sodium D line. Certain of the compounds described herein contain one or more asymmetric centers or axes and may thus give rise to enantiomers, diastereomers, and other stereoisomeric forms that may be defined, in terms of absolute stereochemistry, as (R)- or (S)-. The present invention is meant to include all such possible isomers, including racemic mixtures, optically pure forms and intermediate mixtures. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or owns-configuration.

Pharmaceutical Compositions, Use and Methods

The compounds of the present invention can be therapeutically administered as the neat chemical, but it may be useful to administer the compounds as a pharmaceutical composition or formulation. Thus, the present invention provides a pharmaceutical composition comprising a therapeutically effective amount of a compound of formula (I) or a pharmaceutically acceptable salt, geometric isomer, enantiomer, distereomer, racemate, prodrug, solvate, or hydrate thereof, and one or more pharmaceutically acceptable carriers or excipients.

The pharmaceutical compositions can be administered in a variety of dosage forms including, but not limited to, a solid dosage form or a liquid dosage form, an oral dosage form, a parenteral dosage form, an intranasal dosage form, a suppository, a lozenge, a troche, buccal, a controlled release dosage form, a pulsed release dosage form, an immediate release dosage form, an intravenous solution, a suspension or combinations thereof. The compounds can be administered, for example, by oral or parenteral routes, including intravenous, intramuscular, intraperitoneal, subcutaneous, transdermal, airway (aerosol), rectal, vaginal and topical (including buccal and sublingual) administration.

Preferably, the compound of formula (I) is administered parenterally, such as intravenous (IV) administration. The formulations for administration will commonly comprise a solution of the compound of formula (I) dissolved in a pharmaceutically acceptable carrier. Among the acceptable vehicles and solvents that can be employed are water and Ringer's solution, an isotonic sodium chloride. In addition, sterile fixed oils can conventionally be employed as a solvent or suspending medium. For this purpose, any bland fixed oil can be employed, including synthetic mono- or diglycerides. In addition, fatty acids such as oleic acid can likewise be used in the preparation of injectables. These solutions are sterile and generally free of undesirable matter. These formulations may be sterilized by conventional, well-known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol.

In one embodiment of the invention, the compound of formula (I) is administered orally. For oral administration, the compounds will generally be provided in unit dosage form of a tablet, pill, dragee, lozenge or capsule; as a powder or granules; or as an aqueous solution, suspension, liquid, gel, syrup, slurry, etc. suitable for ingestion by the subject. The dosage form can be a controlled release dosage form formulated as a tablet or a caplet. Tablets for oral use may include the active ingredients mixed with one or more pharmaceutically acceptable excipients. An "excipient" generally refers to a substance, often an inert substance, added to a pharmacological composition or otherwise used as a vehicle to further facilitate administration of a compound. Examples of excipients include, but are not limited to, inert diluents, disintegrating agents, binding agents, lubricating agents, sweetening agents, flavoring agents, coloring agents, preservatives, effervescent mixtures, and adsorbents. Suitable inert diluents include, but are not limited to, sodium and calcium carbonate, sodium and calcium phosphate, lactose, and the like. Suitable disintegrating agents include, but are not limited to, starches, such as corn starch, cross-linked polyvinyl pyrrolidone, agar, alginic acid, or a salt thereof, such as sodium alginate, and the like. Binding agents may include, but are not limited to, magnesium aluminum silicate, starches such as corn, wheat or rice starch, gelatin, methylcellulose, sodium carboxymethylcellulose, polyvinylpyrrolidone, and the like. A lubricating agent, if present, will generally be magnesium stearate and calcium stearate, stearic acid, talc, or hydrogenated vegetable oils. If desired, the tablet may be coated with a material such as glyceryl monostearate or glyceryl distearate, to delay absorption in the gastrointestinal tract. The compositions can also be formulated as chewable tablets, for example, by using substances such as mannitol in the formulation.

Pharmaceutical compositions for oral use can be obtained through combination of a compound of formula (I) with a solid excipient, optionally grinding the resulting mixture, and processing the mixture of granules, after adding suitable additional compounds, if desired, to obtain tablets or dragee cores. Suitable solid excipients in addition to those previously mentioned are carbohydrate or protein fillers that include, but are not limited to, sugars, including lactose, sucrose, mannitol, or sorbitol; starch from corn, wheat, rice, potato, or other plants; cellulose such as methyl cellulose, hydroxypropylmethyl-cellulose or sodium carboxymethyl-cellulose; and gums including arabic and tragacanth; as well as proteins such as gelatin and collagen.

Capsules for oral use include hard gelatin capsules in which the active ingredient is mixed with a solid diluent, and soft gelatin capsules wherein the active ingredient is mixed with water or an oil such as peanut oil, liquid paraffin or olive oil.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

For transmucosal administration (e.g., buccal, rectal, nasal, ocular, etc.), penetrants appropriate to the barrier to be permeated are used in the formulation. Such penetrants are generally known in the art.

The pharmaceutical compositions also may comprise suitable solid or gel phase carriers. Examples of such carriers include, but are not limited to, calcium carbonate, calcium phosphate, various sugars, starches, cellulose derivatives, gelatin, and polymers such as polyethylene glycols.

Compounds and pharmaceutical compositions suitable for use in the present invention include those wherein the active ingredient is administered in an effective amount to achieve its intended purpose. The term "therapeutically effective amount" refers to that amount of a compound of formula (I), or geometric isomers, enantiomers, distereomers, racemates, pharmaceutically acceptable salts, prodrugs, solvates, or hydrates thereof, alone or in combination with ionizing radiation or an anticancer agent which, upon single or multiple dose administration to the subject, provides the desired effect in the subject under treatment. Toxicity and therapeutic efficacy of such compounds can be determined by standard pharmaceutical procedures in cell cultures or experimental animals, e.g., for determining the $IC_{50}$ or $EC_{50}$ values. As used herein, "$IC_{50}$" refers to the concentration of an agent which produces 50% of the maximal inhibitory response possible for that agent and "$EC_{50}$" refers to the concentration of an agent which produces 50% of the maximal response possible for that agent.

The amount of the compound of formula (I) actually administered will be determined by a physician under the relevant circumstances, including the condition to be treated, the size and the type of neoplasia, the chosen route of administration, the actual compound of the present invention administered, the timing of the administration of the Chk1 inhibitors relative to the other therapies, the type, species, age, weight, sex and medical condition of the subject, the renal and hepatic function of the subject, and the severity of the subject's symptoms. Optimal precision in achieving concentration of drug within the range that yields efficacy requires a regimen based on the kinetics of the drug's availability to target sites. This involves consideration of the distribution, equilibrium, and elimination of a drug. Dosages per day normally fall within the range of about 0.1 to about 10 mg/kg of body weight. In some instances, dosage levels below the lower limit of the aforesaid range may be more than adequate, while in the other cases still larger doses may be employed.

A "subject." to be treated by the method of the present invention means either a human or non-human animal, such as primate, mammal, and vertebrate.

"In vivo" means within a living subject, as within an animal or human. In this context, agents can be used therapeutically in vivo to retard or eliminate the proliferation of aberrantly replicating cells. The agents also can be used in vivo as a prophylactic to prevent aberrant cell proliferation or the manifestation of symptoms associated therewith.

"Ex vivo" means outside a living subject. Examples of ex vivo cell populations include cell cultures and biological samples, such as fluid or tissue samples from humans or animals. Such samples can be obtained by methods well known in the art. Exemplary biological fluid samples include blood, cerebrospinal fluid, urine, and saliva. Exemplary tissue samples include tumors and biopsies thereof. In this context, the present compounds can be employed in numerous applications, both therapeutic and experimental.

The present invention also relates to the use of a compound of formula (I), or a pharmaceutically acceptable salt, geometric isomer, enantiomer, distereomer, racemate, prodrug, solvate, or hydrate thereof, in the manufacture of a medicament for inhibiting Chk1.

Furthermore, the present invention relates to a method for treating cancer comprising administering a compound of formula (I) or a pharmaceutically acceptable salt, geometric isomer, enantiomer, distereomer, racemate, prodrug, solvate, or hydrate thereof to a subject suffering from cancer.

The term "cancer" as used herein refers to disorders such as solid tumor cancer including breast cancer; squamous cell carcinoma, such as squamous cell carcinoma of head and neck, lung squamous cell carcinoma stage IV, anal squamous cell carcinoma; lung cancer, such as non-small-cell lung cancer; esophagus cancer; liver cancer; gastric cancer; colorectal cancer; bladder cancer; ovary carcinoma; prostate cancer, such as metastatic castration resistant prostate cancer (mCRPC); giloblastoma; pancreatic cancer; or leukemia such as adult acute megakaryoblastic leukemia, adult acute monoblastic leukemia, adult acute monocytic leukemia, adult acute myeloid leukemia with Inv(16)(p13.1q22), CBFB-MYH11, adult acute myeloid leukemia with maturation, adult acute myeloid leukemia with minimal differentiation, adult acute myeloid leukemia with t(16;16)(p13.1; q22), adult acute myeloid leukemia with t(8;21)(q22;q22), RUNX1-RUNX1T1, adult acute myeloid leukemia with t(9;11)(p22;q23), MLLT3-MLL, adult acute myeloid leukemia without maturation, adult acute myelomonocytic leukemia, adult erythroleukemia, adult pure erythroid leukemia, alkylating agent-related acute myeloid leukemia, and recurrent adult acute myeloid leukemia.

Additional types of cancers which may be treated by the present invention include but are not limited to: adrenocarcinoma, angiosarcoma, astrocytoma, acoustic neuroma, anaplastic astrocytoma, basal cell carcinoma, blastoglioma, chondrosarcoma, choriocarcinoma, chordoma, craniopharyngioma, cutaneous melanoma, cystadenocarcinoma, endotheliosarcoma, embryonal carcinoma, ependymoma, Ewing's tumor, epithelial carcinoma, fibrosarcoma, gastric cancer, genitourinary tract cancers, glioblastoma multiforme, head and neck cancer, hemangioblastoma, hepatocellular carcinoma, hepatoma, Kaposi's sarcoma, large cell carcinoma, cancer of the larynx, leiomyosarcoma, leukemias, liposarcoma, lymphatic system cancer, lymphomas, lymphangiosarcoma, lymphangioendotheliosarcoma, medullary thyroid carcinoma, medulloblastoma, meningioma mesothelioma, myelomas, myxosarcoma neuroblastoma, neurofibrosarcoma, oligodendroglioma, osteogenic sarcoma, epithelial ovarian cancer, papillary carcinoma, papillary adenocarcinomas, parathyroid tumors, pheochromocytoma, pinealoma, plasmacytomas, retinoblastoma, rhabdomyosarcoma, sebaceous gland carcinoma, seminoma, skin cancers, melanoma, small cell lung carcinoma, squamous cell carcinoma, sweat gland carcinoma, synovioma, thyroid cancer, uveal melanoma, stomach cancers, and Wilm's tumor.

The compounds of formula (I) can be administered as the sole active agent, or in combination with other known cancer treatments.

The term "in combination with" means that the compound of formula (I) may be administered shortly before, shortly after, concurrently, or any combination of before, after, or concurrently, with other anti-neoplasm therapies. Thus, the compound of formula (I) and the anticancer agent may be administered simultaneously either as a single composition or as two separate compositions or sequentially as two separate compositions. Likewise, the compound of formula (I) and ionizing radiation therapy may be administered simultaneously, separately or sequentially. The compound of formula (I) may be administered in combination with more than one anticancer agents. In a preferred embodiment, the compound of formula (I) may be administered from 2 weeks to 1 day before any chemotherapy, or 2 weeks to 1 day before any ionizing radiation therapy. In another preferred embodiment, the compound of formula (I) may be administered during chemotherapies and ionizing radiation therapies. If administered following such chemotherapy or ionizing radiation therapy, the compound of formula (I) may be given within 1 to 14 days following the primary treatments. The compound of formula (I) may also be administered chronically or semi-chronically, over a period of from about 2 weeks to about 5 years. One skilled in the art will recognize that the amount of compound of formula (I) to be administered in combination with anticancer agents is preferably that amount sufficient to enhance the effect of the anticancer agents or ionizing radiation therapies or that amount sufficient to induce apoptosis or cell death along with the anticancer agents or ionizing radiation therapy and/or to maintain an antiangiogenic effect.

The term "second anticancer agents" as used herein, unless otherwise indicated, refers to agents capable of inhibiting or preventing the growth of neoplasms, or checking the maturation and proliferation of malignant (cancer) cells. Second anticancer agents suitable for use in combination with the compounds of formula (I) include, but are not limited to targeted cancer drugs, such as trastuzumab, ramucirumab, vismodegib, sonidegib, bevacizumab, everolimus, tamoxifen, toremifene, fulvestrant, anastrozole, exemestane, lapatinib, letrozole, pertuzumab, ado-trastuzumab emtansine, palbociclib, cetuximab, panitumumab, ziv-aflibercept, regorafenib, lmatinib mesylate, lanreotide acetate, sunitinib, regorafenib, denosumab, alitretinoin, sorafenib, pazopanib, temsirolimus, everolimus, tretinoin, dasatinib, nilotinib, bosutinib, rituximab, alemtuzumab, ofatumumab, obinutuxumab, ibrutinib, idelalisib, blinatumomab, sorafenib, crizotinib, erlotinib, gefitinib, afatinib dimaleate, ceritnib, ramucirumab, nivolumab, pembrolizumab, osimertinib, and necitumumab; an alkylating agent, such as busulfan, chlorambucil, cyclophosphamide, iphosphamide, melphalan, nitrogen mustard, streptozocin, thiotepa, uracil nitrogen mustard, triethylenemelamine, temozolomide, and 2-chloroethyl-3-sarcosinamide-1-nitrosourea (SarCNU); an antibiotic or plant alkaloid, such as actinomycin-D, bleomycin, cryptophycins, daunorubicin, doxorubicin, idarubicin, irinotecan, L-asparaginase, mitomycin-C, mitramycin, navelbine, paclitaxel, docetaxel, topotecan, vinblastine, vincristine, teniposide (VM-26), and etoposide (VP-16); a hormone or steroid, such as 5α-reductase inhibitor, aminoglutethimide, anastrozole, bicalutamide, chlorotrianisene, diethylstilbestrol (DES), dromostanolone, estramustine, ethinyl estradiol, flutamide, fluoxymesterone, goserelin, hydroxyprogesterone, letrozole, leuprolide, medroxyprogesterone acetate, megestrol acetate, methyl prednisolone, methyltestosterone, mitotane, nilutamide, prednisolone, arzoxifene (SERM-3), tamoxifen, testolactone, testosterone, triamicnolone, and zoladex; a synthetic, such as all-trans retinoic acid, carmustine (BCNU), carboplatin (CBDCA), lomustine (CCNU), cis-diaminedichloroplatinum (cisplatin), dacarbazine, gliadel, hexamethylmelamine, hydroxyurea, levamisole, mitoxantrone, o,p'-dichlorodiphenyldichloroethane (o,p'-DDD) (also known as Lysodren or mitotane), oxaliplatin, porfimer sodium, procarbazine, and imatinib mesylate (Gleevec®), an antimetabolite, such as chlorodeoxyadenosine, cytosine arabinoside, 2'-deoxycoformycin, fludarabine phosphate, 5-fluorouracil (5-FU), 5-fluoro-2'-deoxyuridine (5-F UdR), gemcitabine, camptothecin, 6-mercaptopurine, methotrexate, 4-methylthioamphetamine (4-MTA), and thioguanine; and a biologic, such as alpha interferon, BCG (Bacillus Calmette-Guerin), granulocyte colony stimulating factor (G-CSF), granulocyte-macrophage colony-stimulating factor (GM-CSF), interleukin-2, and herceptin.

In one preferred embodiment, the second anticancer agent is irinotecan.

The term "treating," as used herein, unless otherwise indicated, means reversing, alleviating, inhibiting the progress of, or preventing the disorder or condition to which such term applies, or one or more symptoms of such disorder or condition. The term "treatment," as used herein, unless otherwise indicated, refers to the act of treating as "treating" is defined immediately above.

Compound Synthesis

The invention also relates to a method for preparing a compound of formula (I), or geometric isomers, enantiomers, distereomers, racemates, pharmaceutically acceptable salts, prodrugs, solvates, or hydrates thereof. The pyrazole compounds of the present invention can be made by one skilled in the art using conventional organic synthesis and commercially available materials.

In one embodiment, the present invention provides a method for preparing a compound of formula (I), or a pharmaceutically acceptable salt, geometric isomer, enantiomer, distereomer, racemate, prodrug, solvate, or hydrate thereof, which comprises:

a. reacting a compound of formula (1)

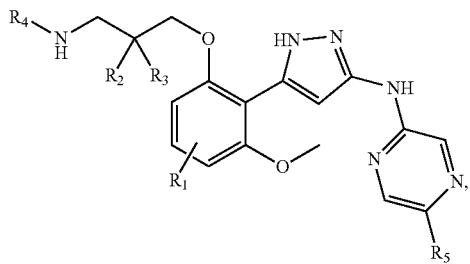

(I)

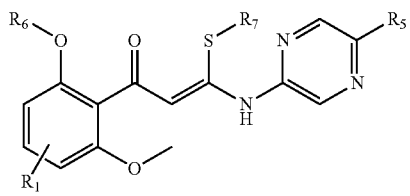

(1)

with a hydrazine of formula H$_2$N—NH$_2$, wherein R$_1$ and R$_5$ are as defined herein; R$_6$ is a hydroxy protecting group; R$_7$ is alkyl; in the presence of a solvent to obtain a compound of formula (2)

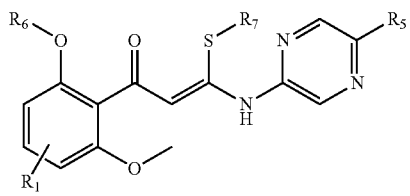

(2)

wherein R$_1$, R$_5$ and R$_6$ are as defined above;

b. de-protecting the compound of formula (2), followed by reacting the de-protected compound with a compound of formula (3)

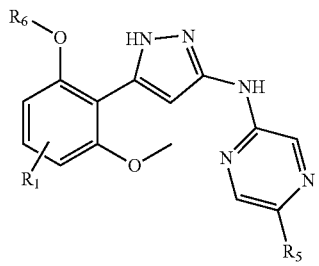

(3)

wherein R$_2$, R$_3$, and R$_4$ are as defined herein, and R$_9$ is an amino protecting group, in the presence of a coupling agent to provide a compound of formula (4)

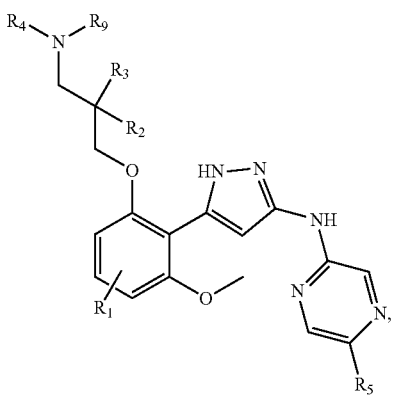

(4)

wherein R$_1$, R$_2$, R$_3$, R$_4$, R$_5$ and R$_9$ are as defined above; and c. de-protecting the compound of formula (4) to obtain a compound of formula (I).

By way of example and not limitation, a compound of formula (I) or a pharmaceutically acceptable salt, geometric isomer, enantiomer, distereomer, racemate, prodrug, solvate, or hydrate thereof can be prepared as outlined in Schemes 1 to 4 shown below. It should be noted that one skilled in the art can modify the procedures set forth in the illustrative schemes and examples to arrive at the desired product.

Scheme 1

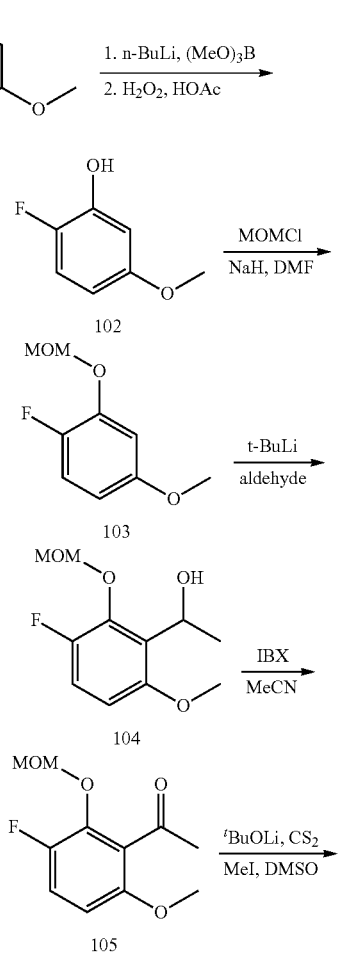

-continued
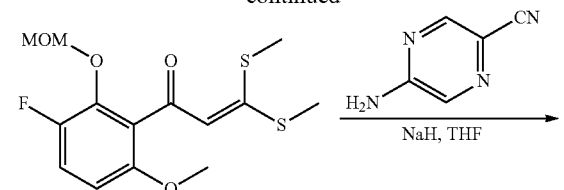
106
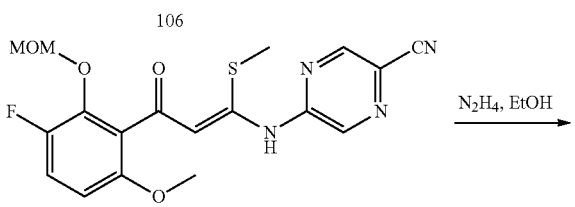
107
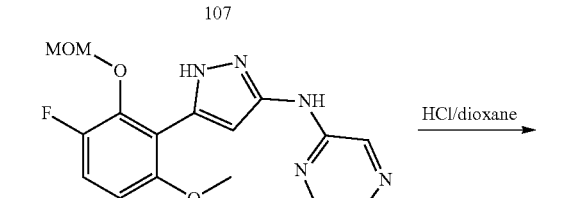
108
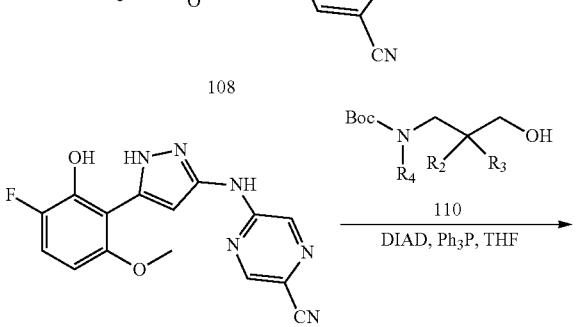
109
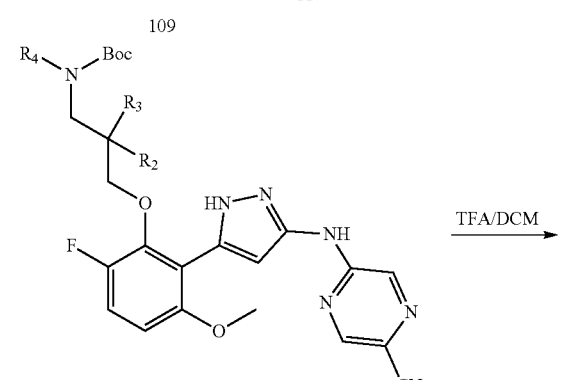
111
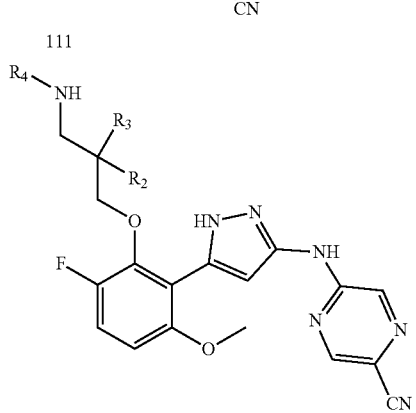
Scheme 2
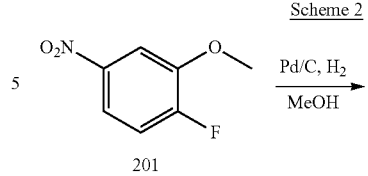
201
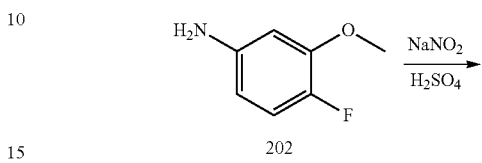
202
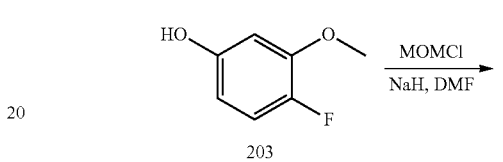
203
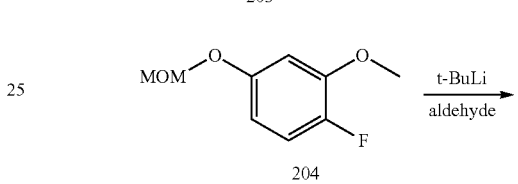
204
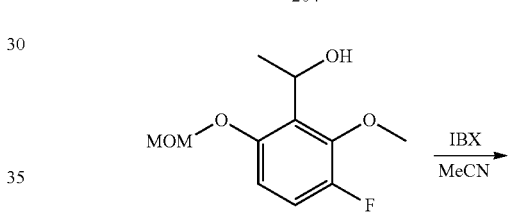
205
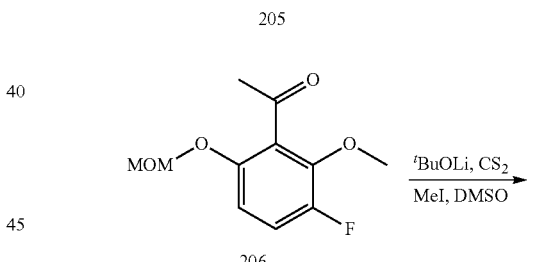
206
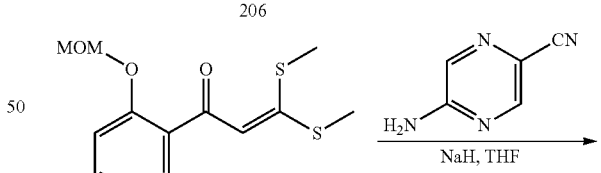
207
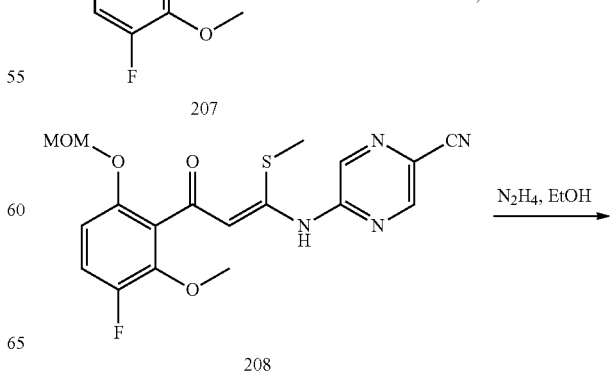
208

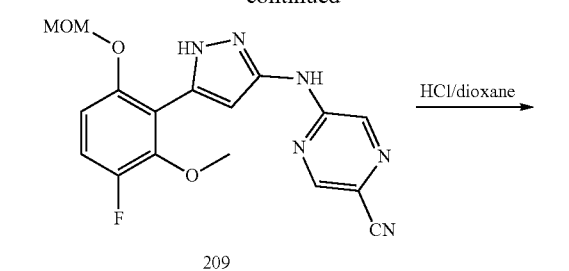
209
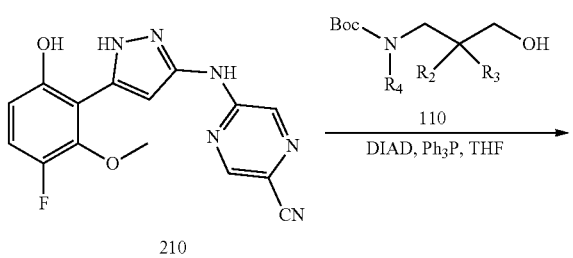
210
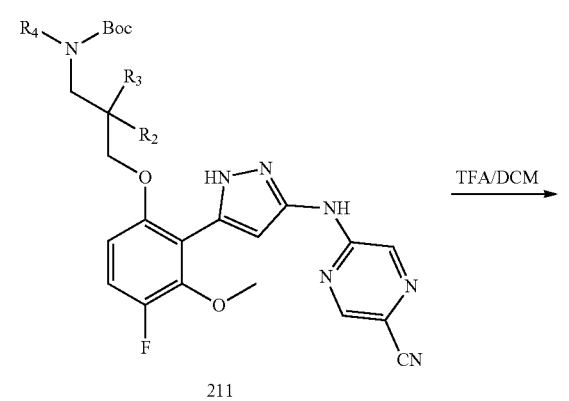
211
Scheme 3
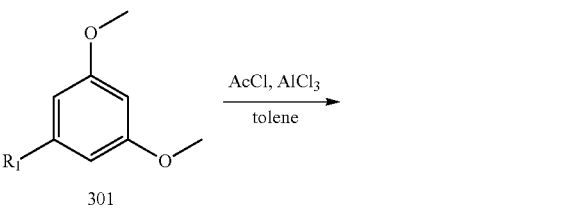
301
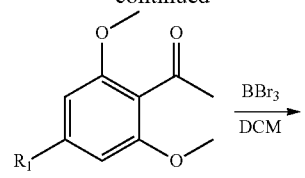
302
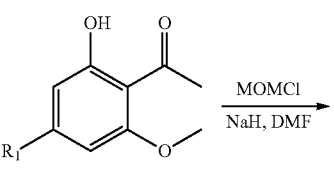
303
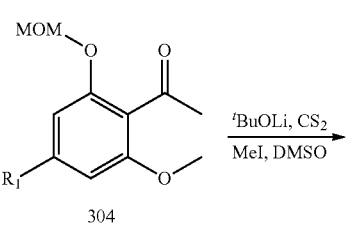
304
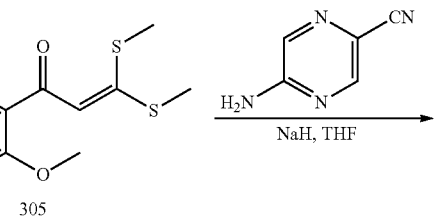
305
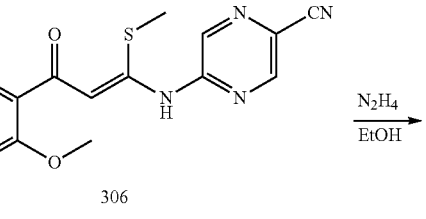
306
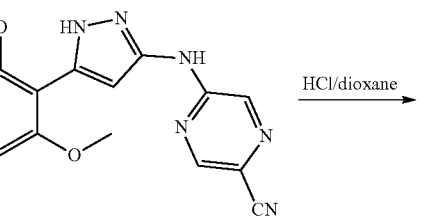
307
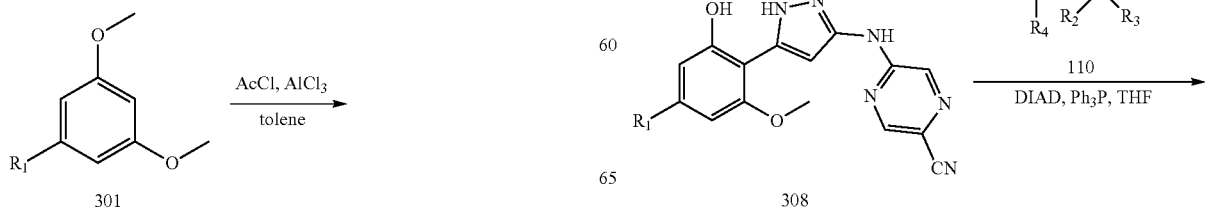
308

-continued

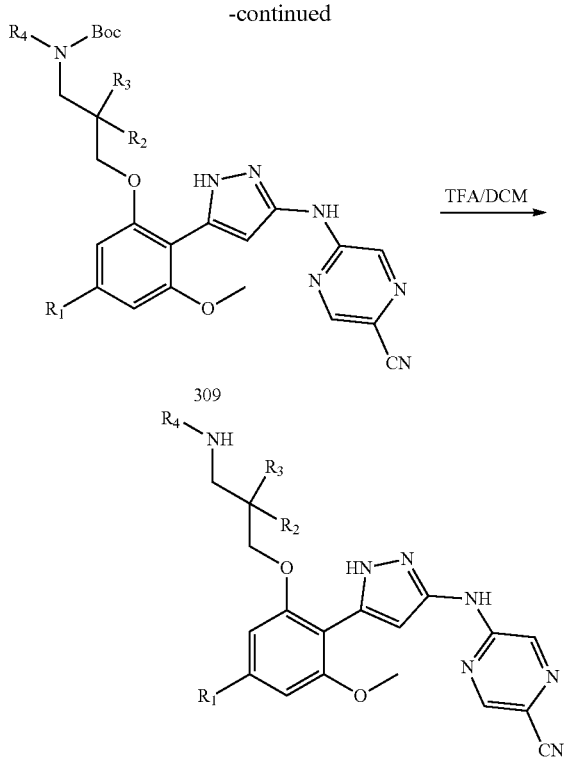

Scheme 4

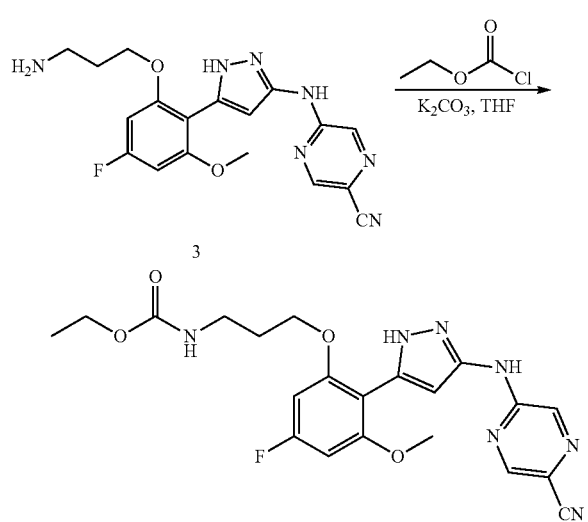

"Protecting groups" are widely used and well known in organic synthesis and refer to functional groups which are capable of masking the reactivity of certain groups in a sensitive reaction under specified conditions (e.g., pH, temperature, radiation, solvent, and the like). As used herein, the term "hydroxy protecting group" refers to a functional group which is capable of masking the reactivity of a hydroxy group in a hydroxy sensitive reaction. Examples of hydroxy protecting groups include, but are not limited to, a methoxymethyl (MOM) ether, a methoxyethoxymethyl (MEM) ether, a methyl thiomethyl (MTM) ether, a trimethylsilyl (TMS) ether, a tert-butyldimethylsilyl (TBDMS) ether, a tri-iso-propylsilyloxymethyl (TOM) ether, a triisopropylsilyl (TIPS) ether, a benzyloxymethyl (BOM) ether, a tetrahydropyranyl (THP) ether, an ethoxyethyl (EE) ether, 2-napthylmethyl ether (NAP), and the like. The term "amino protecting group" refers to a functional group which is capable of masking the reactivity of an amino group in an amino sensitive reaction under specified conditions (e.g., pH, temperature, radiation, solvent, and the like). Examples of amino protecting groups include, but are not limited to, carbobenzyloxy (Cbz), p-methoxybenzyl (PMB), p-methoxybenzyl carbonyl (MeOZ), tert-butyloxycarbonyl (BOC), 9-fluorenylmethyloxycarbonyl (FMOC), benzyl (Bn), benzoyl (Bz), carbamate, toxyl (Ts) group, and the like.

The term "coupling agent" refers to compounds which enable a coupling reaction. Examples of coupling agents include, but are not limited to, primary and secondary amines, thiols, thiolates, and thioethers, alcohols, alkoxide, azides, semicarbazides, and the like.

Without further elaboration, it is believed that the above description has adequately enabled the present invention. The following examples are, therefore, to be construed as merely illustrative, and not limitative of the remainder of the disclosure in any way whatsoever.

EXAMPLES

Example 1

Preparation of 5-(5-(2-(3-Aminopropoxy)-3-fluoro-6-methoxyphenyl)-1H-pyrazol-3-ylamino)pyrazine-2-carbonitrile (Compound 1)

Step 1a. 2-Fluoro-5-methoxyphenol (Compound 102)

To a solution of 1-fluoro-4-methoxybenzene (5.0 g, 40.0 mmol) and pentamethyldiethylenetriamine (6.9 g, 40.0 mmol) in anhydrous THF (25 mL) was added n-BuLi (16.5 mL, 2.5 M in hexane, 41.0 mmol) at −70° C. under $N_2$. Trimethyl borate (9.4 g, 90.0 mmol) was added 3 hours later. After 1 hour, the reaction mixture was warmed to −10° C. and acetic acid (7 mL) was added. The reaction temperature was then changed to 5° C. and 30% $H_2O_2$ (7.5 mL) was added. The resulting mixture was stirred at room temperature overnight. The reaction mixture was quenched with 10% aqueous sodium sulfite and extracted with tert-butyl methyl ether. To the organic layer was added a 2 N aqueous sodium hydroxide (25 mL). After adding 5 N hydrochloric acid to the aqueous layer to adjust the pH to 6, the resulting mixture was extracted with tert-butyl methyl ether. The organic layer was washed with water and brine, dried over anhydrous sodium sulfate, filtered and evaporated in vacuo to obtain the crude product which was purified by column chromatography (hexanes/ethyl acetate: 40/1) to afford the title compound 102 (5.2 g, 91% yield) as a colorless oil. $^1$H NMR (400 MHz, $CDCl_3$): δ 3.76 (s, 3H), 5.42 (s, 1H), 6.39-6.35 (m, 1H), 6.57 (dd, J=7.2, 2.8 Hz, 1H), 6.99-6.94 (m, 1H).

Step 1b. 1-Fluoro-4-methoxy-2-(methoxymethoxy)benzene (Compound 103)

A mixture of compound 101 (3.0 g, 21.1 mmol) and sodium hydride (17 g, 42.2 mmol) in DMF (25 mL) was stirred at room temperature for 2 hours and then cooled with an ice bath. To this cold mixture chloro(methoxy)methane (2.6 g, 31.7 mmol) was added. The reaction mixture was stirred at room temperature for 2 hours and was then quenched with water and extracted with ethyl acetate. The organic layer was washed with water and brine, dried over anhydrous sodium sulfate, filtered and evaporated in vacuo to obtain the crude product, which was purified by column chromatography (hexanes/ethyl acetate: 5/1) to afford the title compound 103 (3.35 g, 85% yield) as a colorless oil. $^1$H NMR (400 MHz, CDCl$_3$): δ 3.52 (s, 3H), 3.76 (s, 3H), 5.20 (s, 214), 6.48-6.45 (m, 1H), 6.77 (dd, J=6.8, 2.8 Hz, 1H), 6.99 (dd, J=10.8, 9.2 Hz, 1H).

Step 1c. 1-(3-Fluoro-6-methoxy-2-(methoxymethoxy)phenyl)ethanol (Compound 104)

To a solution of compound 103 (3.5 g, 18.8 mmol) in anhydrous THF (35 mL) was added 1.3 N t-BuLi (29 mL, 1.3M in hexane) at −70° C. The reaction mixture was stirred for 3 hours and then acetaldehyde (1.7 g, 37.6 mmol) was added and stirred for an additional 1 hour. The reaction mixture was quenched with water and extracted with ethyl acetate. The organic layer was washed with water and brine, dried over anhydrous sodium sulfate, filtered and evaporated in vacuo (hexanes/ethyl acetate: 4/1) to afford the title compound 104 (3.0 g, 70% yield) as a colorless oil. LCMS: 253.0[M+1]$^+$. $^1$H NMR (400 MHz, CDCl$_3$): δ 1.56 (d, J=6.8 Hz, 3H), 3.59 (s, 3H), 3.85 (s, 3H), 5.19-5.13 (m, 2H), 5.33-5.25 (m, 1H), 6.58 (dd, J=9.2, 3.6 Hz, 1H), 6.98-6.91 (m, 1H).

Step 1d. 1-(3-Fluoro-6-methoxy-2-(methoxymethoxy)phenyl)ethanol (Compound 105)

A mixture of compound 104 (3.0 g, 13.0 mmol) and 2-iodoxybenzoic acid (5.5 g, 19.5 mmol) in acetonitrile (45 mL) was refluxed for 1.5 hours. The reaction mixture was quenched with water and extracted with ethyl acetate. The organic layer was washed with water and brine, dried over anhydrous sodium sulfate, filtered and evaporated in vacuo to yield the crude product, which was purified by column chromatography (hexanes/ethyl acetate: 40/1) to afford the title compound 105 (2.29 g, 77% yield) as a colorless oil. $^1$H NMR (400 MHz, CDCl$_3$): δ 2.51 (s, 3H), 3.50 (s, 3H), 3.79 (s, 314), 5.12 (s, 2H), 6.59 (dd, J=9.2, 3.2 Hz, 1H), 7.05 (dd, J=10.8, 9.2 Hz, 1H).

Step 1e. 1-(3-Fluoro-6-methoxy-2-(methoxymethoxy)phenyl)-3,3-bis(methylthio) prop-2-en-1-one (Compound 106)

To a stirred mixture of lithium tert-butoxide (2.4 g, 30.0 mmol) in anhydrous DMSO (40 mL) was added compound 105 (2.29 g, 10.0 mmol) at room temperature. The mixture was stirred at 30° C. for 2 hours and CS$_2$ (1.52 g, 20.0 mmol) was added slowly at room temperature. After 2 hours, iodomethane (2.84 g, 20.0 mmol) was added slowly while keeping the temperature below 30° C. The resulting reaction mixture was stirred at room temperature for 1 hour and then quenched with water and extracted with ethyl acetate. The organic layer was separated and dried over Na$_2$SO$_4$, filtered and concentrated. The residue was purified by column chromatography (hexanes/ethyl acetate: 4/1) to afford the title compound 106 (2.8 g, 85% yield) as a yellow solid. LCMS: 333.1 [M+1]$^+$. $^1$H NMR (400 MHz, CDCl$_3$): δ 2.43 (s, 3H), 2.51 (s, 3H), 3.47 (s, 3H), 3.76 (s, 3H), 5.09 (s, 2H), 6.22 (s, 1H), 6.59 (dd, J=9.2, 3.2 Hz, 1H), 7.06-7.01 (m, 1H).

Step 1f. (Z)-5-(3-(3-Fluoro-6-methoxy-2-(methoxymethoxy)phenyl)-1-(methylthio)-3-oxo-prop-1-enylamino)pyrazine-2-carbonitrile (Compound 107)

To a stirred mixture of 5-aminopyrazine-2-carbonitrile (542 mg, 4.5 mmol) in THF (20 mL) was slowly added sodium hydride (240 mg, 6.02 mmol) below 15° C. The resulting mixture was stirred at room temperature for 1 hour and compound 106 (1.0 g, 3.01 mmol) was added. The reaction mixture was stirred at 60° C. for 4 hours, quenched with ice-water and extracted with ethyl acetate. The organic layer was dried over Na$_2$SO$_4$, filtered and concentrated to afford the title compound 107 (1.0 g, crude) as a yellow solid, which was used for the next step without further purification.

Step 1g. 5-(5-(3-Fluoro-6-methoxy-2-(methoxymethoxy)phenyl)-1H-pyrazol-3-ylamino)pyrazine-2-carbonitrile (Compound 108)

To a stirred mixture of compound 107 (1.0 g, crude) in ethanol (10 mL) was added hydrazine monohydrate (0.5 mL). The reaction mixture was stirred at 55° C. for 1 hour. The resulting slurry was filtered. The cake was washed with cold ethanol, and dried to afford the title compound 108 (500 mg, 45% yield-2 steps) as a yellow solid. LCMS:371.3 [M+1]$^+$. $^1$H NMR (400 MHz, DMSO-d$_6$): δ 3.18 (s, 3H), 3.78 (s, 3H), 4.93 (s, 2H), 6.81 (s, 1H), 6.90 (dd, J=9.2, 4.0 Hz, 1H), 7.33 (dd, J=10.8, 9.2 Hz, 1H), 8.69-8.42 (m, 2H), 10.76 (s, 1H), 12.57 (s, 1H).

Step 1h. 5-(5-(3-Fluoro-2-hydroxy-6-methoxyphenyl)-1H-pyrazol-3-ylamino) pyrazine-2-carbonitrile (Compound 109)

A solution of 108 (160 mg, 0.43 mmol) in HCl-dioxane (20 mL, 2M solution) was heated at room temperature overnight. The reaction mixture was filtered. The cake was adjusted to have a pH of 7-8 with NH$_3$/H$_2$O and extracted with dichloromethane. The organic layer was dried over Na$_2$SO$_4$, filtered and concentrated to afford the title compound 3-101-A8 (100 mg, 71% yield) as a yellow solid. LCMS:327.1 [M+1]$^+$. NKR (400 MHz, DMSO-d$_6$): δ 3.80 (s, 3H), 6.53 (dd, J=9.2, 3.6 Hz, 1H), 6.90 (s, 1H), 7.15 (dd, J=10.4, 9.2 Hz, 1H), 8.72-8.36 (m, 2H), 10.76 (s, 1H), 12.48 (s, 1H).

Step 1i. tert-Butyl 3-(2-(3-(5-cyanopyrazin-2-ylamino)-1H-pyrazol-5-yl)-6-fluoro-3-methoxyphe-noxy)propylcarbamate (Compound 111-1)

To a solution of PPh$_3$ (157 mg, 0.6 mmol) in anhydrous tetrahydrofuran (10 mL) was added DIAD (121 mg, 0.6 mmol) in portions at 0=5° C. The reaction mixture was turned to become a white suspension. After 10 minutes, a solution of tert-butyl 3-hydroxypropylcarbamate (110-1) (104 mg, 0.6 mmol) in anhydrous tetrahydrofuran (5 mL) was added into the suspension slowly while maintaining the temperature between 0=5° C. The mixture prepared above was added in portions to a solution of compound 109 (45 mg, 0.138 mmol) in anhydrous tetrahydrofuran (5 mL) at room temperature. After addition, the solution was stirred at room temperature for 1 hour. The reaction mixture was quenched with water and extracted with ethyl acetate. The organic layer was washed with water and brine, dried over anhydrous sodium sulfate and evaporated in vacuo to give a crude product which was purified by column chromatography (dichloromethane/ethyl acetate: 5/1) to afford the title compound 111-1 (30 mg, crude) as a yellow solid. LCMS: 484.5 [M+1]$^+$.

Step 1j. 5-(5-(2-(3-Aminopropoxy)-3-fluoro-6-methoxyphenyl)-1H-pyrazol-3-ylamino) pyrazine-2-carbonitrile (Compound 1)

To a solution of compound 111-1 (30 mg, crude) in dichloromethane (2 mL) was added trifluoroacetic acid (1 mL). The mixture was stirred at room temperature for 1 hour and then evaporated in vacuo to give a crude product which was purified by HPLC to afford the title compound 1 (10 mg, 18% yield-2 steps) as a yellow solid. M.p.: 221-224° C. LCMS: 384.2 [M+1]$^+$. $^1$H NMR (400 MHz, DMSO-d$_6$): δ 1.80-1.71 (m, 2H), 2.64 (t, J=6.8 Hz, 2H), 3.85 (s, 3H), 4.00 (t, J=6.0 Hz, 2H), 7.03-6.88 (m, 2H), 7.36 (dd, J=10.8, 9.2 Hz, 1H), 8.66-8.46 (m, 1H), 8.72 (s, 1H).

Example 2

5-((5-(6-(3-Aminopropoxy)-3-fluoro-2-methoxyphenyl)-1H-pyrazol-3-yl)amino) pyrazine-2-carbonitrile (Compound 2)

Step 2a. 4-Fluoro-3-methoxyaniline (Compound 202)

To a solution of 1-fluoro-2-methoxy-4-nitrobenzene (101) (5.0 g, 29.0 mmol) in methanol (25 mL) was added 10% Pd/C (500 mg) at room temperature under H$_2$ atmosphere. After reaction completion (monitored by TLC), the mixture was filtered and the filtrate was evaporated under vacuo to afford title compound 202 (4.0 g, 97% yield). $^1$H NMR (400 MHz, DMSO-d$_6$): δ 3.72 (s, 3H), 4.93 (s, 2H), 6.02-6.05 (m, 1H), 6.33 (dd, J=7.6, 2.4 Hz, 1H), 6.81 (dd, J=11.6, 8.8 Hz, 1H).

Step 2b. 4-Fluoro-3-methoxyphenol (Compound 203)

To a suspension of compound 202 (4.0 g, 28.0 mmol) in 30% sulfuric acid (15 mL) was added sodium nitrite (2.15 g, 31.0 mmol) at 0° C. The reaction was stirred at 0° C. for 20 minutes, and then was added to 60% sulfuric acid (15 mL) at 100° C. and stirred for 30 min. The reaction mixture was neutralized with anhydrous NaHCO$_3$ and extracted with ethyl acetate. The organic layer was washed with water and brine, dried over anhydrous sodium sulfate and evaporated in vacuo. The crude product was purified by column chromatography (hexanes/dichloromethane: 3/1) to afford the title compound 203 (1.84 g, 46.7% yield) as a colorless oil. $^1$H NMR (400 MHz, DMSO-d$_6$): δ 3.76 (s, 3H), 6.24-6.27 (m, 1H), 6.51 (dd, J=6.8, 2.8 Hz, 1H), 6.96 (dd, J=11.2, 8.4 Hz, 1H), 9.36 (s, 1H).

Step 2c. 1-Fluoro-2-methoxy-4-(methoxymethoxy)benzene (Compound 204)

To a mixture of compound 203 (4.8 g, 33.8 mmol) in DMF was added sodium hydride (2.7 g, 67.6 mmol) at 0° C. The reaction mixture was stirred at room temperature for 2 hours. Chloro(methoxy)methane (4.1 g, 50.7 mmol) was then added in ice bath. The reaction mixture was stirred at room temperature for 2 hours. The reaction mixture was quenched with water and extracted with ethyl acetate. The organic layer was washed with water and brine, dried over anhydrous sodium sulfate and evaporated in vacuo. The crude product was purified by column chromatography (hexanes/ethyl acetate: 10/1) to afford the title compound 204 (4.5 g, 86% yield) as a colorless oil. $^1$H NMR (400 MHz, DMSO-d$_6$): δ3.38 (s, 3H), 3.81 (s, 3H), 5.16 (m, 2H), 6.54-6.56 (m, 1H), 6.80 (dd, J=7.6, 2.0 Hz, 1H), 6.80 (dd, J=11.6, 9.2 Hz, 1H).

Step 2d. 1-(3-Fluoro-2-methoxy-6-(methoxymethoxy)phenyl)ethanol (Compound 205)

To a solution of compound 204 (4.35 g, 23.4 mmol) in anhydrous THF (35 mL) was added 1.3 N t-BuLi (29 mL, 1.3 M in hexane) at −70° C. The resulting mixture was stirred for 3 hours. Acetaldehyde (1.5 g, 35.1 mmol) was added and stirred for 1 hour. The reaction mixture was quenched with water and extracted with ethyl acetate. The organic layer was washed with water and brine, dried over anhydrous sodium sulfate and evaporated in vacuo. The crude product was purified by column chromatography (hexanes/ethyl acetate: 4/1) to afford the title compound 205 (3.0 g, 56% yield) as a colorless oil. $^1$H NMR (400 MHz, CDCl$_3$): δ 3.49 (s, 3H), 3.68-3.68 (d, J=11.2 Hz, 1H), 3.98 (d, J=2.0 Hz, 3H), 5.16-5.20 (m, 2H), 5.24-5.28 (m, 1H), 6.78 (dd, J=5.2, 3.6 Hz, 114), 6.89-6.94 (m, 1H).

Step 2e. 1-(3-Fluoro-2-methoxy-6-(methoxymethoxy)phenyl)ethanone (Compound 206)

A mixture of compound 205 (860 mg, 3.7 mmol) and 2-iodoxybenzoic acid (2.09 g, 7.47 mmol) in acetonitrile (15 mL) was refluxed for 1.5 hours. The reaction mixture was quenched with water and extracted with ethyl acetate. The organic layer was washed with water and brine, dried over anhydrous sodium sulfate and evaporated in vacuo. The crude product was purified by column chromatography (hexanes/ethyl acetate: 40/1) to afford the title compound 206 (778 mg, 91% yield) as a colorless oil. $^1$H NMR (400 MHz, CDCl$_3$): δ 2.51 (s, 3H), 3.45 (s, 3H), 3.93 (d, J=2.0 Hz, 3H), 5.11 (s, 2H), 6.79 (dd, J=9.2, 3.2 Hz, 1H), 7.00 (dd, J=11.2, 9.2 Hz, 1H).

Step 2f. 1-(3-Fluoro-2-methoxy-6-(methoxymethoxy)phenyl)-3,3-bis(methylthio) prop-2-en-1-one (Compound 207)

To a mixture of lithium tert-butoxide (1.1 g, 30.0 mmol) in anhydrous DMSO (30 mL) was added compound 206 (780 mg, 3.48 mmol) at room temperature. The mixture was stirred at 30° C. for 2 hours and CS$_2$ (651 mg, 8.55 mmol) was added slowly at room temperature. Two hours later, iodomethane (1.21 g, 8.55 mmol) was added slowly while keeping the temperature below 30° C. The resulting reaction mixture was stirred at room temperature for 1 hour, quenched with water and extracted with ethyl acetate. The organic layer was dried over Na$_2$SO$_4$ and concentrated. The residue was purified by column chromatography (hexanes/ethyl acetate: 4/1) to afford the title compound 207 (1.07 g, 94% yield) as a yellow solid. $^1$H NMR (400 MHz, CDCl$_3$): δ 2.42 (s, 3H), 2.52 (s, 3H), 3.44 (s, 3H), 3.90 (d, J=1.6 Hz, 3H), 5.09 (s, 2H), 6.19 (s, 1H), 6.80 (dd, J=8.8, 3.2 Hz, 1H), 7.00 (dd, J=10.8, 9.2 Hz, 1H).

Step 2g. (Z)-5-((3-(3-fluoro-2-methoxy-6-(methoxymethoxy)phenyl)-1-(methylthio)-3-oxo-prop-1-en-1-yl)amino)pyrazine-2-carbonitrile (Compound 208)

To a stirred mixture of 5-aminopyrazine-2-carbonitrile (131 mg, 1.09 mmol) in THE (8 mL) was slowly added sodium hydride (73 mg, 1.82 mmol) below 15° C. The resulting mixture was stirred at room temperature for 1 hour and compound 207 (302 mg, 0.91 mmol) was added. The reaction mixture was then stirred at 60° C. for 4 hours, quenched with ice-water, and extracted with ethyl acetate. The organic layer was dried over $Na_2SO_4$ and concentrated to afford the title compound 208 (280 mg, crude) as a yellow solid.

Step 2h. 5-((5-(3-Fluoro-2-methoxy-6-(methoxymethoxy)phenyl)-1H-pyrazol-3-yl) amino) pyrazine-2-carbonitrile (Compound 209)

To a stirred mixture of compound 208 (250 mg, crude) in ethanol (3 mL) was added hydrazine monohydrate (0.15 mL). The reaction mixture was stirred at 55° C. for 1 hour and the resulting slurry was filtered. The cake was washed with cold ethanol, and dried to afford the title compound 209 (174 mg, 52% yield-2 steps) as a yellow solid. $^1$H NMR (400 MHz, DMSO-$d_6$): δ 3.33 (s, 3H), 3.73 (d, J=1.2 Hz, 3H), 5.18 (s, 2H), 6.84 (s, 1H), 6.96 (dd, J=9.2, 4.4 Hz, 1H), 8.54 (m, 1H), 8.65 (d, J=1.2 Hz, 1H), 10.76 (s, 1H), 12.55 (s, 1H).

Step 2i. 5-((5-(3-Fluoro-6-hydroxy-2-methoxyphenyl)-1H-pyrazol-3-yl)amino)pyrazine-2-carbonitrile (Compound 210)

A solution of compound 209 (175 mg, 0.47 mmol) in HCl-dioxane (20 mL, 2M solution) was heated at room temperature overnight. The reaction mixture was filtered. The cake was adjusted to have a pH of 9-10 with $NH_3/H_2O$ and extracted with dichloromethane. The organic layer was dried over $Na_2SO_4$ and concentrated to afford the title compound 210 (58 mg, 38% yield) as a yellow solid. $^1$H NMR (400 MHz, DMSO-$d_6$): δ 3.75 (s, 3H), 6.67 (dd, J=8.8, 4.0 Hz, 1H), 6.88 (s, 1H), 7.13 (dd, J=10.8, 9.2 Hz, 1H), 8.53 (br, 1H), 8.67 (s, 1H), 10.15 (br, 1H), 10.76 (s, 1H), 12.42 (s, 1H).

Step 2j. tert-Butyl (3-(2-(3-((5-cyanopyrazin-2-yl)amino)-1H-pyrazol-5-yl)-4-fluoro-3-methoxyphenoxy)propyl)carbamate (Compound 211-2)

To a solution of $PPh_3$ (121 mg, 0.46 mmol) in anhydrous tetrahydrofuran (5 mL) was added DIAD (93 mg, 0.46 mmol) in portions at 0-5° C. The reaction mixture was turned to become a white suspension. After 10 minutes, a solution of compound 110-1 (81 mg, 0.46 mmol) in anhydrous tetrahydrofuran (3 mL) was added into the suspension slowly while maintaining the temperature between 0-5° C. The mixture prepared above was added in portions to the solution of compound 210 (50 mg, 0.15 mmol) in anhydrous tetrahydrofuran (3 mL) at room temperature. After addition, the solution was stirred at room temperature for 1 hour. The reaction mixture was quenched with water and extracted with ethyl acetate. The organic layer was washed with water and brine, dried over anhydrous sodium sulfate and evaporated in vacuo. The crude product was purified by column chromatography (dichloromethane/ethyl acetate: 5/1) to afford the title compound 211-2 (80 mg, crude) as a yellow solid, which was used directly in the next step without further purification.

Step 2k. 5-((5-(6-(3-Aminopropoxy)-3-fluoro-2-methoxyphenyl)-1H-pyrazol-3-yl) amino)pyrazine-2-carbonitrile (Compound 2)

To a solution of 211-2 (80 mg, crude) in dichloromethane (3 mL) was added trifluoroacetic acid (3 mL). The reaction mixture was stirred at room temperature for 1 hour and was then evaporated in vacuo to give the crude product, which was purified by HPLC (40%-90% $CH_3CN$ in water, 0.1% $CF_3COOH$) to afford the title compound 2 (20 mg, 34% yield-2 steps) as a yellow solid. M.p.: 80-84° C. LCMS: 384.3 [M+1]$^+$. $^1$H NMR (400 MHz, $CD_3OD$): δ 1.94-1.98 (m, 2H), 2.82 (t, J 6.8 Hz, 2H), 3.83 (s, 3H), 4.12 (t, J=6.0 Hz, 2H), 6.85 (dd, J=9.2, 4.0 Hz, 1H), 6.95 (s, 1H), 7.15-7.20 (m, 1H), 8.49-8.55 (m, 2H).

Example 3

5-(5-(2-(3-Aminopropoxy)-4-fluoro-6-methoxyphenyl)-1H-pyrazol-3-ylamino)pyrazine-2-carbonitrile (Compound 3)

Step 3a. 1-(4-Fluoro-2,6-dimethoxyphenyl)ethanone (Compound 302-3)

To a suspension of aluminum chloride (8.6 g, 64.04 mmol) in toluene (30 mL) was added 1-fluoro-3,5-dimethoxybenzene (301-3) (10.0 g, 64.04 mmol) at 0° C. The reaction mixture was stirred for 2 hours. To the above mixture was added acetyl chloride (5.0 g, 64.04 mmol). The resulting mixture was stirred for an additional 0.5 hours. The reaction mixture was quenched with water and extracted with ethyl acetate. The organic layer was washed with water and brine, dried over anhydrous sodium sulfate and evaporated in vacuo. The crude product was purified by column chromatography (hexanes/ethyl acetate: 25/1) to afford the title compound 302-3 as a white solid (2.78 g, 22% yield). $^1$H NMR (400 MHz, $CDCl_3$): δ 2.46 (s, 3H), 3.79 (s, 6H), 6.29 (d, J=10.8 Hz, 2H).

Step 3b. 1-(4-Fluoro-2-hydroxy-6-methoxyphenyl)ethanone (Compound 303-3)

To a solution of compound 302-3 (2.78 g, 14.0 mmol) in dichloromethane (20 mL) was added 1 N borontribromide (15.5 mL, 1M in dichloromethane) at −20° C. The resulting mixture was stirred for 1 h. The reaction mixture was quenched with water and extracted with dichloromethane. The organic layer was washed with water and brine, dried over anhydrous sodium sulfate and evaporated in vacuo to afford the title compound 303-3 as a white solid (2.3 g, 89% yield). LCMS: 185.1 [M+1]$^+$. $^1$H NMR (400 MHz, $CDCl_3$): δ 2.54 (s, 3H), 3.86 (s, 3H), 6.35 (dd, J=10.8, 2.4 Hz, 1H), 6.51 (dd, J=11.6, 2.4 Hz, 1H), 12.76 (s, 1H).

Step 3c. 1-(4-Fluoro-2-methoxy-6-(methoxymethoxy)phenyl)ethanone (Compound 304-3)

To a solution of compound 303-3 (2.3 g, 12.49 mmol) in THF (20 mL) was added sodium hydride (1.0 g, 24.98 mmol) in portion at 0° C. The reaction was warmed to ambient temperature and stirred for 1 h. Chloro(methoxy) methane (1.51 g, 18.73 mmol) was added at 0° C. The reaction mixture was warmed to ambient temperature and stirred overnight. The reaction mixture was quenched with ice-water and extracted with ethyl acetate. The organic layer was washed with water and brine, dried over anhydrous sodium sulfate and evaporated in vacuo. The crude product was purified by column chromatography (hexanes/ethyl acetate: 15/1) to afford the title compound 304-3 as a colorless oil (1.56 g, 55% yield). $^1$H NMR. (400 MHz, CDCl$_3$): δ 2.48 (s, 3H), 3.46 (s, 3H), 3.79 (s, 3H), 5.14 (s, 2H), 6.33 (dd, J=10.4, 2.0 Hz, 1H), 6.53 (dd, J=10.4, 2.0 Hz, 1H).

Step 3d. 1-(4-Fluoro-2-methoxy-6-(methoxymethoxy)phenyl)-3,3-bis(methylthio) prop-2-en-1-one (Compound 305-3)

To a stirring mixture of lithium tert-butoxide (2.19 g, 27.34 mmol) in anhydrous DMSO (30 mL) was added compound 304-3 (1.56 g, 6.84 mmol) at ambient temperature. The reaction was warmed to 40° C. and stirred at 40° C. for 2 h. The reaction mixture was cooled to ambient temperature and CS$_2$ (1.3 g, 17.09 mmol) was then added slowly. After 2 hours of reaction, iodomethane (2.4 g, 17.09 mmol) was added slowly while keeping the temperature below 30° C. The resulting reaction mixture was stirred at ambient temperature for 1 h and was then quenched with ice-water and extracted with ethyl acetate. The organic layer was dried over Na$_2$SO$_4$ and concentrated. The residue was purified by column chromatography (hexanes/ethyl acetate: 4/1) to afford the title compound 305-3 as a yellow solid (1.42 g, 62% yield). LCMS:333.0 [M+1]$^+$. $^1$H NMR (400 MHz, CDCl$_3$): δ 2.42 (s, 3H), 2.51 (s, 3H), 3.44 (s, 3H), 3.77 (s, 3H), 5.12 (s, 2H), 6.19 (s, 1H), 6.33 (dd, J=10.8, 2.0 Hz, 1H), 6.53 (dd, J=10.8, 2.0 Hz, 1H).

Step 3e. (Z)-5-(3-(4-Fluoro-2-methoxy-6-(methoxymethoxy)phenyl)-1-(methylthio)-3-oxo-prop-1-enylamino)pyrazine-2-carbonitrile (Compound 306-3)

To a stirring mixture of 5-aminopyrazine-2-carbonitrile (433 mg, 3.61 mmol) in THF (10 mL) was slowly added sodium hydride (240 mg, 6.02 mmol) below 15° C. The reaction mixture was stirred at room temperature for 1 h. To the above mixture was added compound 305-3 (1.0 g, 3.01 mmol). The resulting mixture was stirred at 60° C. for 4 h. The reaction mixture was quenched with ice-water and extracted with ethyl acetate. The organic layer was dried over Na$_2$SO$_4$ and concentrated to afford the title compound 306-3 (1.5 g, crude) as a yellow oil. LCMS:405.0[M+1]$^+$.

Step 3f. 5-(5-(4-Fluoro-2-methoxy-6-(methoxymethoxy)phenyl)-1H-pyrazol-3 ylamino) pyrazine-2-carbonitrile (Compound 307-3)

To a stirring mixture of compound 306-3 (1.2 g, crude) in ethanol (10 mL) was added hydrazine monohydrate (265 mg, 4.5 mmol). The reaction mixture was stirred at 50° C. for 1 h. After cooling to ambient temperature, the solid was collected by filtration, washed with cold ethanol and dried to afford the title compound 307-3 as a yellow solid (450 mg, 40% yield via 2 steps). LCMS:371.2 [M+1]$^+$. $^1$H NMR (400 MHz, DMSO-d$_6$): δ 3.34 (s, 3H), 3.80 (s, 3H), 5.23 (s, 2H), 6.71-6.76 (m, 3H), 8.54 (s, 1H), 8.63 (d, J=1.2 Hz, 1H), 10.71 (s, 1H), 12.39 (d, J=1.6 Hz, 1H).

Step 3g. 5-(5-(4-Fluoro-2-hydroxy-6-methoxyphenyl)-1H-pyrazol-3-ylamino) pyrazine-2-carbonitrile (Compound 308-3)

A suspension of compound 307-3 (200 mg, 0.54 mmol) in HCl-dioxane (20 mL, 2M solution) was stirred at ambient temperature overnight. The resulting solid was collected by filtration. The solid was then suspended in water, adjusted to have a pH of 9-10 with ammonia and extracted with dichloromethane. The organic layer was dried over Na$_2$SO$_4$ and concentrated to afford the title compound 308-3 as a yellow solid (140 mg, 79.4% yield). LCMS:327.0[M+1]$^+$. $^1$H NMR (400 MHz, DMSO-d$_6$): δ 3.86 (s, 3H), 6.44 (dd, J=10.4, 2.4 Hz, 1H), 6.56 (dd, J=11.2, 2.4 Hz, 1H), 6.86 (s, 1H), 8.61 (s, 1H), 8.71 (s, 1H), 10.56 (br, 1H), 10.76 (br, 1H), 12.34 (s, 1H).

Step 3h. tert-Butyl 3-(2-(3-(5-cyanopyrazin-2-ylamino)-1H-pyrazol-5-yl)-5-Fluoro-3-methoxyphenoxy)propylcarbamate (Compound 309-3)

To a solution of PPh$_3$ (546 mg, 2.08 mmol) in anhydrous tetrahydrofuran (10 mL) was added DIAD (421 mg, 2.08 mmol) dropwise at 0-5° C., followed by a solution of tert-butyl 3-hydroxypropylcarbamate (110-1) (365 mg, 2.08 mmol) in anhydrous tetrahydrofuran (5 mL). The resulting mixture was added to a solution of compound 308-3 (170 mg, 0.52 mmol) in anhydrous tetrahydrofuran (5 mL) at ambient temperature and stirred at ambient temperature for 1 h. The reaction mixture was quenched with water and extracted with ethyl acetate. The organic layer was washed with water and brine, dried over anhydrous sodium sulfate and evaporated in vacuo. The crude product was purified by column chromatography (dichloromethane/ethyl acetate: 5/1) to afford the title compound 309-3 as a yellow solid (200 mg, crude). LCMS: 484.2 [M+1]$^+$.

Step 3i. 5-(5-(2-(3-Aminopropoxy)-4-fluoro-6-methoxyphenyl)-1H-pyrazol-3-ylamino) pyrazine-2-carbonitrile (Compound 3)

To a solution of compound 309-3 (200 mg, crude) in dichloromethane (4 mL) was added trifluoroacetic acid (2 mL) and the resulting mixture was stirred at ambient temperature for 1 h. The reaction mixture was evaporated in vacuo and the residue was purified by prep-HPLC (35%-90% CH$_3$CN in water, 0.1% CF$_3$COOH) to afford the title compound 3 as a yellow solid (20 mg, 10% yield via 2 steps). M.p.: 229-232° C. LCMS: 384.1 [M+1]$^1$. $^1$H NMR (400 MHz, DMSO-d$_6$): δ 1.76-1.82 (m, 2H), 2.71 (t, J=6.4 Hz, 2H), 3.82 (s, 3H), 4.10 (t, J=6.0 Hz, 2H), 6.66-6.70 (m, 3H), 6.85 (s, 1H), 8.52 (br, 1H), 8.64 (s, 1H).

Example 4

5-(5-(2-(3-Aminopropoxy)-4-chloro-6-methoxyphenyl)-1H-pyrazol-3-ylamino)pyrazine-2-carbonitrile (Compound 4)

Step 4a. 1-(4-Chloro-2,6-dimethoxyphenyl)ethanone (Compound 302-4)

To a mixture of aluminum chloride (9.3 g, 69.5 mmol) and acetyl chloride (4.7 g, 60.8 mmol) in dichloromethane (100 mL) was added 1-chloro-3,5-dimethoxybenzene (301-4) (10.0 g, 57.9 mmol) at 0° C. The resulting mixture was stirred for 1 h. The reaction mixture was quenched with water and extracted with dichloromethane. The organic layer was washed with water and brine, dried over anhydrous sodium sulfate and evaporated in vacuo. The crude product was purified by column chromatography (hexanes/ethyl acetate 25/1) to afford the title compound 302-4 as a white solid (4.5 g, 36% yield). $^1$H NMR (400 MHz, CDCl$_3$): δ 2.45 (s, 3H), 3.79 (s, 6H), 6.56 (s, 2H).

Step 4b. 1-(4-Chloro-2-hydroxy-6-methoxyphenyl) ethanone (Compound 303-4)

To a solution of compound 302-4 (4.5 g, 21.0 mmol) in dichloromethane (20 mL) was added 1 N borontribromide (23.0 mL, 1M in dichloromethane) at −20° C. The resulting mixture was stirred for 1 h. The reaction mixture was quenched with ice water and extracted with dichloromethane. The organic layer was washed with water and brine, dried over anhydrous sodium sulfate and evaporated in vacuo to afford the title compound 303-4 as a white solid (3.5 g, 83% yield). $^1$H NMR. (400 MHz, CDCl$_3$): δ 2.66 (s, 3H), 3.91 (s, 3H), 6.39 (d, J=2.0 Hz, 1H), 6.61 (d, J=2.0 Hz, 1H), 13.48 (s, 1H).

Step 4c. 1-(4-Chloro-2-methoxy-6-(methoxymethoxy)phenyl)ethanone (Compound 304-4)

A mixture of compound 303-4 (2.58 g, 12.86 mmol) and sodium hydride (1.03 g, 25.72 mmol) in THF (20 mL) was stirred at room temperature for 1 hour. Chloro(methoxy) methane (1.55 g, 19.29 mmol) was then added at 0° C. The reaction mixture was stirred at ambient temperature overnight. The reaction mixture was quenched with water and extracted with ethyl acetate. The organic layer was washed with water and brine, dried over anhydrous sodium sulfate and evaporated in vacuo. The crude product was purified by column chromatography (hexanes/ethyl acetate: 15/1) to afford the title compound 304-4 (2.0 g, 64% yield) as a colorless oil. $^1$H NMR (400 MHz, CDCl$_3$): δ 2.46 (s, 3H), 3.45 (s, 3H), 3.79 (s, 3H), 5.13 (s, 2H), 6.59 (d, J=1.2 Hz, 1H), 6.79 (d, J=1.6 Hz, 1H).

Step 4d. 1-(4-Chloro-2-methoxy-6-(methoxymethoxy)phenyl)-3,3-bis(methylthio) prop-2-en-1-one (Compound 305-4)

To a suspension of lithium tert-butoxide (2.62 g, 32.7 mmol) in anhydrous DMSO (30 mL) was added compound 304-4 (2.0 g, 8.17 mmol) at ambient temperature. The resulting mixture was stirred for 2 h. CS$_2$ (1.56 g, 20.44 mmol) was added at ambient temperature and stirred for 2 h. Iodomethane (2.9 g, 20.44 mmol) was added and stirred at ambient temperature for 1 h. The reaction mixture was quenched with water and extracted with ethyl acetate. The organic layer was washed with water and brine, dried over Na$_2$SO$_4$ and concentrated. The crude product was purified by column chromatography (hexanes/ethyl acetate: 5/1) to afford the title compound 305-4 as a yellow solid (1.8 g, 63% yield). $^1$H NMR (400 MHz, CDCl$_3$): δ 2.41 (s, 3H), 2.51 (s, 3H), 3.44 (s, 3H), 3.77 (s, 3H), 5.11 (s, 2H), 6.17 (s, 1H), 6.60 (d, J=1.6 Hz, 1H), 6.80 (d, J=1.6 Hz, 1H).

Step 4e. (Z)-5-(3-(4-Chloro-2-methoxy-6-(methoxymethoxy)phenyl)-1-(methylthio)-3-oxo-prop-1-enylamino)pyrazine-2-carbonitrile (Compound 306-4)

To a suspension of 5-aminopyrazine-2-carbonitrile (414 mg, 3.44 mmol) in THF (10 mL) was added sodium hydride (230 mg, 5.73 mmol) at 0° C. and the resulting mixture was then stirred at ambient temperature for 1 h. Compound 305-4 (1.0 g, 2.87 mmol) was added and stirred at 60° C. for 4 h. The reaction mixture was quenched with ice water and extracted with ethyl acetate. The organic layer was washed with water and brine, dried over Na$_2$SO$_4$ and concentrated to afford the title compound 306-4 as a yellow solid (500 mg, 42% yield). LCMS:420.9 [M+1]$^+$. $^1$H NMR. (400 MHz, DMSO-d$_6$): δ 2.36 (s, 3H), 3.35 (s, 3H), 3.77 (s, 3H), 5.21 (s, 2H), 5.68 (s, 1H), 6.86-6.88 (m, 2H), 8.63 (d, J=1.2 Hz, 1H), 8.86 (d, J=1.2 Hz, 1H), 13.89 (s, 1H).

Step 4f. 5-(5-(4-Chloro-2-methoxy-6-(methoxymethoxy)phenyl)-1H-pyrazol-3-ylamino) pyrazine-2-carbonitrile (Compound 307-4)

A mixture of 306-4 (500 mg, 1.19 mmol) and hydrazine monohydrate (105 mg, 1.78 mmol) in ethanol (10 mL) was stirred at 50° C. for 1 h. After cooling to ambient temperature, the solid was collected by filtration and washed with cold ethanol, and dried to afford the title compound 307-4 as a yellow solid (400 mg, 87% yield). $^1$H NMR (400 MHz, DMSO-d$_6$): δ 3.35 (s, 3H), 3.83 (s, 3H), 5.25 (s, 2H), 6.80 (br, 1H), 6.91 (d, J=2.0 Hz, 1H), 6.93 (d, J=1.6 Hz, 1H), 8.54 (br, 1H), 8.63 (d, 0.1=1.2 Hz, 1H), 10.68 (s, 1H), 12.41 (d, J=1.6 Hz, 1H).

Step 4g. 5-(5-(4-Chloro-2-hydroxy-6-methoxyphenyl)-1H-pyrazol-3-ylamino)pyrazine-2-carbonitrile (Compound 308-4)

A suspension of compound 307-4 (400 mg, 1.03 mmol) in HCl/1,4-dioxane (30 mL, 2M solution) was stirred at ambient temperature overnight. The solid was collected by filtration, adjusted to have a pH of 9-10 with NH$_3$/H$_2$O and extracted with dichloromethane. The organic layer was dried over Na$_2$SO$_4$ and concentrated to afford the title compound 308-4 as a yellow solid (300 mg, 85% yield). LCMS:343.0 [M+1]$^+$. $^1$H NMR (400 MHz, DMSO-d$_6$): δ 3.83 (s, 3H), 6.64 (d, J=1.6 Hz, 1H), 6.67 (d, J=1.6 Hz, 1H), 6.86 (s, 1H), 8.54 (br, 1H), 8.64 (s, 1H), 10.68 (br, 2H), 12.32 (s, 1H).

Step 4h. tert-Butyl 3-(5-chloro-2-(3-(5-cyanopy-razin-2-ylamino)-1H-pyrazol-5-yl)-3-methoxyphe-noxy)propylcarbamate (Compound 309-4)

To a solution of PPh$_3$ (286 mg, 1.09 mmol) in anhydrous tetrahydrofuran (10 mL) was added DIAD (221 mg, 1.09 mmol) by syringe at 0-5° C., followed by a solution of tert-butyl 3-hydroxypropylcarbamate (110-1) (192 mg, 1.09 mmol) in anhydrous tetrahydrofuran (5 mL). The resulting mixture was poured into a solution of compound 308-4 (150 mg, 0.44 mmol) in anhydrous tetrahydrofuran (5 mL) at ambient temperature and stirred for 1 h. The reaction mixture was quenched with water and extracted with ethyl acetate. The organic layer was washed with water and brine, dried over anhydrous sodium sulfate and evaporated in vacuo. The crude product was purified by column chromatography (dichloromethane/ethyl acetate: 5/1) to afford the title compound 309-4 as a yellow solid (300 mg, crude). LCMS: 500.2 [M+1]$^+$.

Step 4i. 5-(5-(2-(3-Aminopropoxy)-4-chloro-6-methoxyphenyl)-1H-pyrazol-3-ylamino) pyrazine-2-carbonitrile (Compound 4)

To a solution of compound 309-4 (300 mg, crude) in dichloromethane (4 mL) was added trifluoroacetic acid (2 mL). The resulting mixture was stirred at ambient temperature for 1 h. The reaction mixture was evaporated in vacuo to give the crude product, which was purified by prep-HPLC (40%-90% CH$_3$CN in water, 0.1% CF$_3$COOH) to afford the title compound 4 as a yellow solid (26 mg, 15% yield via 2 steps). M.p.: 198-203° C. LCMS: 400.4 [M+1]$^+$. $^1$H NMR (400 MHz, DMSO-d$_6$): δ 1.77-1.83 (m, 2H), 2.72 (t, J=6.4 Hz, 2H), 3.85 (s, 3H), 4.12 (t, J=6.4 Hz, 2H), 6.85-6.87 (m, 2H), 6.92 (s, 1H), 8.51 (s, 1H), 8.65 (s, 1H).

Example 5

5-(5-(2-(3-Aminopropoxy)-4-bromo-6-methoxyphenyl)-1H-pyrazol-3-ylamino)pyrazine-2-carbonitrile (Compound 5)

Step 5a. 1-(4-Bromo-2,6-dimethoxyphenyl)ethanone (Compound 302-5)

To a suspension of AlCl$_3$ (3.69 g, 0.028 mol) in dichloromethane (40 mL) was added acetyl chloride (1.99 g, 0.025 mol) below −5° C. Once the resulting mixture became limpid, 1-bromo-3,5-dimethoxybenzene (301-5) (5.0 g, 0.023 mol) in dichloromethane (10 mL) was added at −5° C. The yellow reaction mixture was quenched with saturated ammonium chloride and extracted with dichloromethane. The organic layer was washed with water and brine, dried over anhydrous sodium sulfate and evaporated in vacuo. The crude product was recrystallized from hexanes (20 mL) and ethyl acetate (4 mL) to afford the title product 302-5 as a white solid (3 g, 50% yield). $^1$H NMR (400 MHz, CDCl$_3$): δ 2.44 (s, 3H), 3.79 (s, 6H), 6.72 (s, 2H).

Step 5b. 1-(4-Bromo-2-hydroxy-6-methoxyphenyl) ethanone (Compound 303-5)

To a solution of compound 302-5 (200 mg, 0.77 mmol) in DCM (3 mL) was added BBr$_3$ (213 mg, 0.85 mmol) below −15° C. The resulting mixture was stirred at ambient temperature for 1h. The yellow reaction solution was quenched with ice water and extracted with dichloromethane. The organic layer was washed with water and brine, dried over anhydrous Na$_2$SO$_4$ and concentrated. The crude product was purified by column chromatography (hexanes/ethyl acetate: 20/1) to afford the title compound 303-5 as a pale yellow solid (160 mg, 85% yield). $^1$H NMR (400 MHz, CDCl$_3$): δ 2.65 (s, 3H), 3.90 (s, 3H), 6.54 (d, J=2.0 Hz, 1H), 6.78 (d, J=2.0 Hz, 1H), 13.41 (s, 1H).

Step 5c. 1-(4-Bromo-2-methoxy-6-(methoxymethoxy)phenyl)ethanone (Compound 304-5)

To a solution of compound 303-5 (160 mg, 0.65 mmol) in dry THF (10 mL) was added NaH (40 mg, 0.98 mmol) at 0° C. The resulting mixture was stirred for 1h. Chloro (methoxy)methane (78 mg, 0.98 mmol) was added at 0° C. and stirred at ambient temperature for 15 min. The reaction mixture was quenched with ice water and extracted with ethyl acetate. The organic layer was dried over anhydrous Na$_2$SO$_4$ and concentrated. The crude product was purified by column chromatography (hexanes/ethyl acetate: 10/1) to afford the title compound 304-5 as a colorless oil (160 mg, 85% yield). $^1$H NMR (400 MHz, CDCl$_3$): δ 2.46 (s, 3H), 2.46 (s, 3H), 3.80 (s, 3H), 5.13 (s, 2H), 6.75 (d, J=0.8 Hz, 1H), 6.96 (d, J=1.6 Hz, 1H).

Step 5d. 1-(4-Bromo-2-methoxy-6-(methoxymethoxy)phenyl)-3,3-bis(methylthio) prop-2-en-1-one (Compound 305-5)

To a solution of 304-5 (160 mg, 0.55 mmol) in DMSO (5 mL) was added t-BuOLi (111 mg, 1.38 mmol) at ambient temperature. The resulting mixture was stirred for 1 h, followed by addition of CS$_2$ (63 mg, 0.83 mmol). After the resulting mixture was stirred for 2 hours, iodomethane (196 mg, 1.38 mmol) was added at ambient temperature and stirred for an additional 1 h. The reaction mixture was quenched with water and extracted with ethyl acetate. The organic layer was dried over anhydrous Na$_2$SO$_4$ and concentrated. The residue was purified by column chromatography (ethyl acetate/hexanes: 1/5) to afford the title compound 305-5 (120 mg, 55% yield) as a yellow oil. $^1$H NMR (400 MHz, CDCl$_3$): δ 2.41 (s, 3H) 2.51 (s, 3H), 3.44 (s, 3H), 3.77 (s, 3H), 5.11 (s, 2H), 6.16 (s, 1H), 6.75 (d, J=1.6 Hz, 1H), 6.96 (d, J=1.2 Hz, 1H).

Step 5e. (Z)-5-(3-(4-bromo-2-methoxy-6-(methoxymethoxy)phenyl)-1-(methylthio)-3-oxo-prop-1-enylamino)pyrazine-2-carbonitrile (Compound 306-5)

To a suspension of 5-aminopyrazine-2-carbonitrile (44.3 mg, 0.37 mmol) in THF (10 mL) was added NaH (24.4 mg, 0.61 mmol) at 0° C. The resulting mixture was stirred at ambient temperature for 1 h. A solution of compound 305-5 (120 mg, 0.31 mmol) in THF (2 mL) was added and stirred at 55° C. for 3.5 h. The reaction mixture was quenched with ice water and extracted with ethyl acetate. The organic layer was washed with water and brine, dried over anhydrous Na$_2$SO$_4$ and concentrated. The crude product was purified by column chromatography (hexanes/ethyl acetate: 3/1) to afford the title compound 306-5 as a yellow solid (110 mg, 77% yield).

Step 5f. 5-(5-(4-Bromo-2-methoxy-6-(methoxymethoxy)phenyl)-1H-pyrazol-3-ylamino) pyrazine-2-carbonitrile (Compound 307-5)

A mixture of compound 306-5 (540 mg, 1.16 mmol) and hydrazine monohydrate (116 mg, 2.32 mmol) in ethanol (10 mL) was stirred at 50° C. for 1 h. After cooling to ambient temperature, the solid was collected by filtration, washed with cold ethanol and dried to afford the title compound 307-5 as a yellow solid (176 mg, 35% yield).

Step 5g. 5-(5-(4-Bromo-2-hydroxy-6-methoxyphenyl)-1H-pyrazol-3-ylamino)pyrazine-2-carbonitrile (Compound 308-5)

A suspension of compound 307-5 (200 mg, 0.46 mmol) in HCl/1,4-dioxane (8 mL, 2M solution) was stirred at 40° C. for 1.5 h. After cooling to ambient temperature, the solid was collected by filtration, adjusted to have a pH of 9-10 with NH$_3$/H$_2$O and dried to afford the title compound 308-5 as a yellow solid (166 mg, 93% yield).

Step 5h. tert-Butyl 3-(5-bromo-2-(3-(5-cyanopyrazin-2-ylamino)-1H-pyrazol-5-yl)-3-methoxyphenoxy)propylcarbamate (Compound 309-5)

To a solution of PPh$_3$ (179 mg, 0.68 mmol) in dry THF (4 mL) was added DIAD (138 mg, 0.68 mmol) by syringe at 0-5° C., followed by a solution of tert-butyl 3-hydroxypropylcarbamate (110-1) (82 mg, 0.68 mmol) in anhydrous Tiff (2 mL). The resulting mixture was poured into a solution of compound 308-5 (88 mg, 0.23 mmol) in dry THF (2 mL) at ambient temperature and stirred for 1 h. The reaction mixture was quenched with water and extracted with ethyl acetate. The organic layer was washed with water and brine, dried over anhydrous sodium sulfate and evaporated in vacuo. The crude product was purified by column chromatography (dichloromethane/ethyl acetate: 3/1) to afford the title compound 309-5 as a yellow solid (190 mg, crude). LCMS: 545.9 [M+1]$^+$.

Step 5i. 5-(5-(2-(3-Aminopropoxy)-4-bromo-6-methoxyphenyl)-1H-pyrazol-3-ylamino) pyrazine-2-carbonitrile (Compound 5)

A mixture of compound 309-5 (376 mg, crude) in TFA (1.5 mL) and DCM (2 mL) was stirred at ambient temperature for 1.5 h. The reaction mixture was evaporated in vacuo to give the crude product, which was purified by prep-HPLC (40%-90% CH$_3$CN in water, 0.1% CF$_3$COOH) to afford the title compound 5 as a pale yellow solid (48 mg, 47% yield via 2 steps). M.p.: 165-175° C. LCMS: 446.0 [M+1]$^+$. $^1$H NMR (400 MHz, DMSO-d$_6$): δ1.85-1.88 (m, 2H), 2.78 (t, J=6.4 Hz, 2H), 3.87 (s, 3H), 4.16 (t, J=6.0 Hz, 2H), 6.94 (br, 1H), 7.00 (s, 1H), 7.01 (s, 1H), 8.53 (br, 1H), 8.68 (s, 1H).

Example 6

5-(5-(2-(3-aminopropoxy)-6-methoxy-4-methylphenyl)-1H-pyrazol-3-ylamino)pyrazine-2-carbonitrile (Compound 6)

Step 6a. 1-(2-Hydroxy-6-methoxy-4-methylphenyl)ethanone (Compound 303-6)

To a solution of 5-methylbenzene-1,3-diol (10.0 g, 80.55 mmol) and aluminum chloride (32.0 g, 241.66 mmol) in chlorobenzene (60 mL) was added acetyl chloride (8.9 g, 112.78 mmol) at 0° C. The resulting mixture was stirred for 30 min. The resulting mixture was warmed to 70° C. and stirred for an additional 2 h. The reaction mixture was then quenched with ice water and extracted with ethyl acetate. The organic layer was washed with water and brine, dried over anhydrous sodium sulfate and evaporated in vacuo. The crude product was purified by column chromatography (hexanes/ethyl acetate: 20/1) to afford the title compound 1-(2,6-Dihydroxy-4-methylphenyl)ethanone as a yellow solid (10 g, 75% yield). LCMS: 167.0 [M+1]$^+$. $^1$H NMR (400 MHz, DMSO-d$_6$): 2.17 (s, 3H), 2.62 (s, 3H), 6.20 (s, 2H), 11.87 (s, 2H). A mixture of the above compound (5.0 g, 30.11 mmol), iodomethane (6.4 g, 45.17) and K$_2$CO$_3$ (20.8 g, 150.5 mmol) in acetonitrile (50 mL) was stirred at 35° C. overnight. The reaction mixture was filtered and washed with acetonitrile. The filtrate was evaporated in vacuo. The crude product was purified by column chromatography (hexanes/ethyl acetate: 50/1) to afford the title compound 303-6 as a yellow solid (4.5 g, 83% yield). $^1$H NMR (400 MHz, CDCl$_3$): δ 2.30 (s, 3H), 2.64 (s, 3H), 3.88 (s, 3H), 6.19 (s, 1H), 6.39 (s, 1H), 13.33 (s, 1H).

Step 6b. 1-(2-Methoxy-6-(methoxymethoxy)-4-methylphenyl)ethanone (Compound 304-6)

To a solution of compound 303-6 (4.5 g, 25 mmol) in THF (50 mL) was added sodium hydride (2.0 g, 50 mmol) at 0° C. The resulting mixture was stirred at ambient temperature for 1 h. Chloro(methoxy)methane (3.0 g, 37.5 mmol) was added at 0° C. and stirred at ambient temperature overnight. The reaction mixture was quenched with ice water and extracted with ethyl acetate. The organic layer was washed with water and brine, dried over anhydrous sodium sulfate and evaporated in vacuo. The crude product was purified by column chromatography (hexanes/ethylacetate: 15/1) to afford the title compound 304-6 as a yellow oil (4.5 g, 84% yield).

Step 6c. 1-(2-Methoxy-6-(methoxymethoxy)-4-methylphenyl)-3,3-bis(methylthio) prop-2-en-1-one (Compound 305-6)

To a stirred mixture of lithium tert-butoxide (8.0 g, 100 mmol) in anhydrous DMSO (100 mL) was added compound 304-6 (4.5 g, 20 mmol) at ambient temperature. The resulting mixture was stirred at 50° C. for 1 h. CS$_2$ (3 g, 40 mmol) was added slowly at ambient temperature and stirred for 3 h. Iodomethane (8.5 g, 60 mmol) was then added at 50° C. and stirred at for 2 h. After cooling to ambient temperature, the reaction mixture was quenched with water, extracted with ethyl acetate and water. The organic layer was washed with water and brine, dried over Na$_2$SO$_4$ and concentrated. The crude product was purified by column chromatography (hexanes/ethyl acetate: 4/1) to afford the title compound 305-6 as a yellow solid (1.7 g, 26% yield). LCMS:329.3 [M+1]$^+$. $^1$H NMR (400 MHz, DMSO-d$_6$): δ 2.29 (s, 3H), 2.42 (s, 3H), 2.45 (s, 3H), 3.33 (s, 3H), 3.70 (s, 3H), 5.11 (s, 2H), 6.15 (s, 1H), 6.55 (s, 1H), 6.58 (s, 1H).

Step 6d. (Z)-5-(3-(2-methoxy-6-(methoxymethoxy)-4-methylphenyl)-1-(methylthio)-3-oxoprop-1-enylamino)pyrazine-2-carbonitrile (Compound 306-6)

To a suspension of 5-aminopyrazine-2-carbonitrile (750 mg, 6.22 mmol) in THF (10 mL) was added sodium hydride (420 mg, 10.36 mmol) at 0-5° C. The resulting mixture was then stirred at ambient temperature for 1 h. Compound 305-6 (1.7 g, 5.18 mmol) was added and stirred at 60° C. for 4 h. The reaction mixture was quenched with ice-water and extracted with ethyl acetate. The organic layer was washed with water and brine, dried over Na$_2$SO$_4$ and concentrated. The crude product was purified by column chromatography (hexanes/ethyl acetate: 5/1) to afford the title compound 306-6 as a yellow solid (1.0 g, 50% yield). LCMS:401.1 [M+1]$^+$. $^1$H NMR (400 MHz, CDCl$_3$): δ 2.34 (s, 3H), 2.36 (s, 3H), 3.46 (s, 3H), 3.81 (s, 3H), 5.16 (s, 2H), 5.69 (s, 1H), 6.46 (s, 1H), 6.63 (s, 1H), 8.37 (d, J=1.2 Hz, 1H), 8.52 (d, J=1.6 Hz, 1H), 14.64 (s, 1H).

Step 6e. 5-(5-(2-Methoxy-6-(methoxymethoxy)-4-methylphenyl)-1H-pyrazol-3-ylamino) pyrazine-2-carbonitrile (Compound 307-6)

A mixture of compound 306-6 (800 mg, 2 mmol) and hydrazine monohydrate (150 mg, 3 mmol) in ethanol (10 mL) was stirred at 50° C. for 1 h. After cooling to room temperature, the solid was collected by filtration, washed with cold ethanol, and dried to afford the title compound 307-6 as a yellow solid (600 mg, 82% yield). LCMS:367.4 [M+1]$^+$. $^1$H NMR (400 MHz, DMSO-d$_6$): δ 2.33 (s, 3H), 3.34 (s, 3H), 3.79 (s, 3H), 5.19 (s, 2H), 6.64 (s, 1H), 6.68 (s, 1H), 6.78 (s, 1H), 8.56 (br, 1H), 8.62 (d, J=1.2 Hz, 1H), 10.64 (s, 1H), 12.29 (d, J=1.6 Hz, 1H).

Step 6f. 5-(5-(2-Hydroxy-6-methoxy-4-methylphenyl)-1H-pyrazol-3-ylamino)pyrazine-2-carbonitrile (Compound 308-6)

A suspension of compound 307-6 (600 mg, 1.64 mmol) in HCl/dioxane (20 mL, 2M solution) was stirred at ambient temperature overnight. The solid was collected by filtration, adjusted pH to 9-10 with NH$_3$/H$_2$O and extracted with dichloromethane. The organic layer was washed with water and brine, dried over Na$_2$SO$_4$ and concentrated to afford the title compound 308-6 as a yellow solid (480 mg, 91% yield). LCMS:323.1[M+1]$^+$. $^1$H NMR (400 MHz, DMSO-d$_6$): δ 2.25 (s, 3H), 3.79 (s, 3H), 6.42 (s, 2H), 6.86 (s, 1H), 8.58 (br, 1H), 8.63 (s, 1H), 9.91 (s, 1H), 10.60 (s, 1H), 12.16 (s, 1H).

Step 6g. tert-Butyl 3-(2-(3-(5-cyanopyrazin-2-ylamino)-1H-pyrazol-5-yl)-3-methoxy-5-methylphenoxy)propylcarbamate (Compound 309-6)

To a solution of PPh$_3$ (314 mg, 1.2 mmol) in anhydrous tetrahydrofuran (10 mL) was added DIAD (242 mg, 1.2 mmol) by syringe at 0-5° C., followed by a solution of tert-butyl 3-hydroxypropylcarbamate (110-1) (210 mg, 1.2 mmol) in anhydrous tetrahydrofuran (5 mL). The resulting mixture was poured into a solution of compound 308-6 (130 mg, 0.4 mmol) in anhydrous tetrahydrofuran (5 mL) at ambient temperature and stirred for 10 min. The reaction mixture was quenched with water and extracted with ethyl acetate. The organic layer was washed with water and brine, dried over anhydrous sodium sulfate and evaporated in vacuo. The crude product was purified by column chromatography (dichloromethane/ethyl acetate: 5/1) to afford the title compound as a yellow solid 309-6 (100 mg, crude).

Step 6h. 5-(5-(2-(3-aminopropoxy)-6-methoxy-4-methylphenyl)-1H-pyrazol-3-ylamino) pyrazine-2-carbonitrile (Compound 6)

To a solution of compound 309-6 (100 mg, crude) in dichloromethane (4 mL) was added trifluoroacetic acid (2 mL). The resulting mixture was stirred at ambient for 1 h. The reaction mixture was evaporated in vacuo and purified by prep-HPLC (30%-90% CH$_3$CN in water, 0.1% CF$_3$COOH) to afford the title compound 3-113 as a yellow solid (20 mg, 10% yield via 2 steps). M.p.: 188-191° C. LCMS: 380.4 [M+1]$^+$. $^1$H NMR (400 MHz, DMSO-d$_6$): δ 1.93-1.97 (m, 2H), 2.34 (s, 3H), 2.87 (t, J=6.8 Hz, 2H), 3.81 (s, 3H), 4.10 (t, J=5.6 Hz, 2H), 6.61 (s, 2H), 6.88 (s, 1H), 8.55 (br, 1H), 8.67 (s, 1H).

Example 7

5-(5-(2-(3-Aminopropoxy)-4,6-dimethoxyphenyl)-1H-pyrazol-3-ylamino)pyrazine-2-carbonitrile (Compound 7)

Step 7a. 1-(2-Hydroxy-4,6-dimethoxyphenyl)ethanone (Compound 303-7)

To a mixture of 3,5-dimethoxyphenol (2.0 g, 12.9 mmol) and triethylamine (2.0 g, 19.4 mmol) in 1,2-dichloroethane (10 mL) was added acetyl chloride (1.2 g, 15.6 mmol) at 0° C. The resulting mixture was then stirred for 0.5 h. The reaction mixture was quenched with ice water and extracted with ethyl acetate. The organic layer was washed with water and brine, dried over anhydrous sodium sulfate and evaporated in vacuo. The crude product was purified by column chromatography (hexanes/ethyl acetate: 15/1) to afford the title compound 3,5-Dimethoxyphenyl acetate as a yellow solid (2.2 g, 85% yield). LCMS: 197.1 [M+1]$^+$. $^1$H NMR (400 MHz, CDCl$_3$): δ 2.27 (s, 3H), 3.76 (s, 6H), 6.26 (d, J=2.4 Hz, 2H), 6.31-6.38 (m, 1H). To a suspension of aluminum trichloride (120 mg, 1.53 mmol) in chlorobenzene (4 mL) was added the above obtained compound (200 mg, 1.02 mmol) in chlorobenzene (4 mL). The resulting mixture was stirred at 70° C. for 4 h. The reaction mixture was quenched with ice water and extracted with ethyl acetate. The organic layer was washed with water and brine, dried over anhydrous sodium sulfate and evaporated in vacuo. The crude product was purified by column chromatography (hexanes/ethyl acetate: 20/1) to afford the title compound 303-7 as a yellow solid (65 mg, 33% yield). $^1$H NMR (400 MHz, DMSO-d$_6$): δ 2.55 (s, 3H), 3.81 (s, 3H), 3.86 (s, 3H), 6.08 (d, J=2.4 Hz, 1H), 6.11 (d, J=2.4 Hz, 1H), 13.76 (s, 1H).

Step 7b. 1-(2,4-Dimethoxy-6-(methoxymethoxy)phenyl)ethanone (Compound 304-7)

To a solution of compound 303-7 (500 mg, 2.55 mmol) in THF (10 mL) was added sodium hydride (153 g, 3.82 mmol) at 0° C. The resulting mixture was then stirred at ambient temperature for 1 h. Chloro(methoxy)methane (308 mg, 3.82 mmol) was added at 0° C. and stirred at ambient temperature for 1 h. The reaction mixture was quenched with water and extracted with ethyl acetate. The organic layer was washed with water and brine, dried over anhydrous sodium sulfate and evaporated in vacuo. The crude product was purified by column chromatography (hexanes/ethyl acetate: 15/1) to afford the title compound 304-7 as a yellow oil (403 mg, 66% yield). LCMS: 241.1 [M+1]$^+$. $^1$H NMR (400 MHz, CDCl$_3$): δ 2.47 (s, 3H), 3.46 (s, 3H), 3.79 (s, 3H), 3.80 (s, 3H), 5.14 (s, 2H), 6.15 (t, J=2.0 Hz, 1H), 6.33 (d, J=2.0 Hz, 1H).

Step 7c. 1-(2,4-Dimethoxy-6-(methoxymethoxy)phenyl)-3,3-bis(methylthio)prop-2-en-1-one (Compound 305-7)

To a suspension of lithium tert-butoxide (416 mg, 5.20 mmol) in anhydrous DMSO (20 mL) was added 304-7 (500 mg, 2.08 mmol) at ambient temperature. The resulting mixture was stirred for 1 h. CS$_2$ (237 mg, 3.12 mmol) was added at ambient temperature and stirred for 3 h. Iodomethane (739 mg, 5.20 mmol) was added at ambient temperature and stirred overnight. The reaction mixture was quenched with water and extracted with ethyl acetate. The organic layer was washed with water and brine, dried over Na$_2$SO$_4$ and concentrated. The crude product was purified by column chromatography (hexanes/ethyl acetate: 4/1) to afford the title compound 305-7 as a yellow solid (180 mg, 26% yield). LCMS:345.3 NMR (400 MHz, DMSO-d$_6$): δ 2.40 (s, 3H), 2.49 (s, 3H), 3.45 (s, 3H), 3.77 (s, 3H), 3.80 (s, 3H), 5.12 (s, 2H), 6.17 (d, J=2.0 Hz, 1H), 6.26 (s, 1H), 6.34 (d, J=2.0 Hz, 1H).

Step 7d. (Z)-5-(3-(2,4-dimethoxy-6-(methoxymethoxy)phenyl)-1-(methylthio)-3-oxoprop-1-enylamino)pyrazine-2-carbonitrile (Compound 306-7)

To a suspension of 5-aminopyrazine-2-carbonitrile (211 mg, 1.74 mmol) in THF (10 mL) was added sodium hydride (116 mg, 2.90 mmol) at 0° C. and stirred at ambient temperature for 1 h. Compound 305-7 (500 mg, 1.45 mmol) was added and stirred at 55° C. for 2 h. After cooling to ambient temperature, the reaction mixture was quenched with ice-water and extracted with ethyl acetate. The organic layer was washed with water and brine, dried over $Na_2SO_4$ and concentrated. The crude product was purified by column chromatography (hexanes/ethyl acetate: 5/1) to afford the title compound 306-7 as a yellow solid (253 mg, 42% yield).

Step 7e. 5-(5-(2,4-Dimethoxy-6-(methoxymethoxy) phenyl)-1H-pyrazol-3-ylamino) pyrazine-2-carbonitrile (Compound 307-7)

A mixture of compound 306-7 (253 mg, 0.61 mmol) and hydrazine monohydrate (48 mg, 0.96 mmol) in ethanol (6 mL) was stirred at 85° C. for 20 min. After cooling to ambient temperature, the solid was collected by filtration, washed with cold ethanol and dried to afford the title compound 307-7 as a yellow solid (203 mg, 88% yield).

Step 7f. 5-(5-(2-hydroxy-4,6-dimethoxyphenyl)-1H-pyrazol-3-ylamino)pyrazine-2-carbonitrile (Compound 308-7)

A solution of compound 307-7 (1.2 g, 3.14 mmol) in HCl/1,4-dioxane (20 mL, 2M solution) was stirred at ambient temperature overnight. The solid was collected by filtration, adjusted to have a pH of 9-10 with $NH_3/H_2O$ and extracted with dichloromethane. The combined organic layers were washed with water and brine, dried over $Na_2SO_4$ and concentrated to afford the title compound 308-7 as a yellow solid (1.0 g, 94% yield).

Step 7g. tert-Butyl 3-(2-(3-(5-cyanopyrazin-2-ylamino)-1H-pyrazol-5-yl)-3,5-dimethoxy phenoxy) propylcarbamate (Compound 309-7)

To a solution of $PPh_3$ (236 mg, 0.9 mmol) in anhydrous tetrahydrofuran (6 mL) was added DIAD (182 mg, 0.9 mmol) by syringe at 0-5° C., followed by a solution of tert-butyl 3-hydroxypropylcarbamate (110-1) (155 mg, 0.9 mmol) in anhydrous tetrahydrofuran (5 mL). The resulting mixture was poured into a solution of compound 308-7 (100 mg, 0.3 mmol) in anhydrous tetrahydrofuran (5 mL) at ambient temperature and stirred for 10 min. The reaction mixture was quenched with water and extracted with ethyl acetate. The organic layer was washed with water and brine, dried over anhydrous sodium sulfate and evaporated in vacuo. The crude product was purified by column chromatography (dichloromethane/ethyl acetate: 5/1) to afford the title compound 309-7 as a yellow solid (300 mg, crude). LCMS: 496.6 $[M+1]^+$.

Step 7h. 5-(5-(2-(3-Aminopropoxy)-4,6-dimethoxyphenyl)-1H-pyrazol-3-ylamino) pyrazine-2-carbonitrile (Compound 7)

To a solution of compound 309-7 (100 mg, crude) in dichloromethane (4 mL) was added trifluoroacetic acid (2 mL). The resulting mixture was stirred at ambient temperature for 1 h. The reaction mixture was evaporated in vacuo and purified by prep-HPLC (30%-90% $CH_3CN$ in water, 0.1% $CF_3COOH$) to afford the title compound 7 as a yellow solid (20 mg, 10% yield via 2 steps). M.p.: 145-151° C. LCMS: 396.4 $[M+1]^+$. $^1H$ NMR (400 MHz, DMSO-$d_6$): δ 1.80-1.87 (m, 2H), 2.76 (t, J=6.4 Hz, 2H), 3.82 (d, J=2.4 Hz, 6H), 4.10 (t, J=6.0 Hz, 2H), 6.33 (s, 1H), 6.34 (s, 1H), 6.84 (s, 1H), 8.54 (br, 2H), 8.65 (s, 1H).

Example 8

5-(5-(2-((1-(Aminomethyl)cyclopropyl)methoxy)-4-fluoro-6-methoxyphenyl)-1H-pyrazol-3-ylamino) pyrazine-2-carbonitrile (Compound 13)

Step 8a. tert-Butyl (1-((2-(3-(5-cyanopyrazin-2-ylamino)-1H-pyrazol-5-yl)-5-fluoro-3-methoxyphenoxy)methyl)cyclopropyl)methylcarbamate (Compound 309-13)

To a solution of $PPh_3$ (242 mg, 0.92 mmol) in anhydrous tetrahydrofuran (10 mL) was added DIAD (186 mg, 0.92 mmol) by syringe at 0-5° C., followed by a solution of tert-butyl (1-(hydroxymethyl)cyclopropyl)methylcarbamate (110-13) (185 mg, 0.92 mmol) in anhydrous tetrahydrofuran (5 mL). The resulting mixture was poured into a solution of compound 308-3 (100 mg, 0.306 mmol) in anhydrous tetrahydrofuran (5 mL) at ambient temperature and stirred for 1 h. The reaction mixture was quenched with water and extracted with ethyl acetate. The organic layer was washed with water and brine, dried over anhydrous sodium sulfate and evaporated in vacuo. The crude product was purified by column chromatography (dichloromethane/ethyl acetate: 5/1) to afford the title compound 309-13 as a yellow solid (400 mg, crude). LCMS: 510.5 $[M+1]^+$.

Step 8b. 5-(5-(2-((1-(Aminomethyl)cyclopropyl) methoxy)-4-fluoro-6-methoxyphenyl)-1H-pyrazol-3-ylamino)pyrazine-2-carbonitrile (Compound 13)

To a solution of compound 309-13 (400 mg, crude) in dichloromethane (4 mL) was added trifluoroacetic acid (2 mL). The resulting mixture was stirred at ambient temperature for 1 h. The reaction mixture was evaporated in vacuo and purified by prep-HPLC (35%-90% $CH_3CN$ in water, 0.1% $CF_3COOH$) to afford the title compound 13 as a yellow solid (40 mg, 32% yield via 2 steps). M.p.: 202-206° C. LCMS: 410.5 $[M+1]^+$. $^1H$ NMR (400 MHz, DMSO-$d_6$): δ 0.48-0.51 (m, 4H), 2.66 (s, 2H), 3.84 (s, 3H), 3.96 (s, 2H), 6.63-6.69 (m, 2H), 6.95 (s, 1H), 8.50 (br, 1H), 8.61 (s, 1H).

Example 9

5-(5-(2-((1-(Aminomethyl)cyclopropyl)methoxy)-4-chloro-6-methoxyphenyl)-1H-pyrazol-3-ylamino) pyrazine-2-carbonitrile (Compound 14)

Step 9a. tert-Butyl (1-((5-chloro-2-(3-(5-cyanopyrazin-2-ylamino)-1H-pyrazol-5-yl)-3-methoxyphenoxy)methyl)cyclopropyl)methylcarbamate (Compound 309-14)

To a solution of $PPh_3$ (459 mg, 1.75 mmol) in anhydrous tetrahydrofuran (10 mL) was added DIAD (354 mg, 1.75 mmol) by syringe at 0-5° C., followed by a solution of tert-butyl (1-(hydroxymethyl)cyclopropyl)methylcarbamate (110-13) (352 mg, 1.75 mmol) in anhydrous tetrahydrofuran (5 mL). The resulting mixture was poured into a suspension of compound 308-4 (200 mg, 0.58 mmol) in anhydrous tetrahydrofuran (5 mL) at ambient temperature for 1 h. The reaction mixture was quenched with water and extracted with ethyl acetate. The organic layer was washed with water and brine, dried over anhydrous sodium sulfate and evaporated in vacuo. The crude product was purified by column chromatography (dichloromethane/ethyl acetate: 5/1) to afford the title compound 309-14 as a yellow solid (500 mg, crude). LCMS: 526.2 [M+1]$^+$.

Step 9b. 5-(5-(2-((1-(Aminomethyl)cyclopropyl) methoxy)-4-chloro-6-methoxyphenyl)-1H-pyrazol-3-ylamino)pyrazine-2-carbonitrile (Compound 14)

To a solution of compound 309-14 (500 mg, crude) in dichloromethane (3 mL) was added trifluoroacetic acid (3 mL). The resulting mixture was stirred at ambient temperature for 1 h. The reaction mixture was evaporated in vacuo and purified by prep-HPLC (40%-90% CH$_3$CN in water, 0.1% CF$_3$COOH) to afford the title compound 14 as a yellow solid (50 mg, 20% yield via 2 steps). M.p.: 232-236° C. LCMS: 427.0 [M+1]$^+$. $^1$H NMR (400 MHz, DMSO-d$_6$): δ 0.44-0.54 (m, 4H), 2.64 (s, 2H), 3.86 (s, 3H), 3.99 (s, 2H), 6.84 (s, 1H), 6.85 (s, 1H), 7.01 (s, 1H), 8.50 (br, 1H), 8.62 (d, J=1.2 Hz, 1H).

Example 10

5-(5-(2-((1-(Aminomethyl)cyclopropyl)methoxy)-4-bromo-6-methoxyphenyl)-1H-pyrazol-3-ylamino) pyrazine-2-carbonitrile (Compound 15)

Step 10a. tert-Butyl (1-((5-bromo-2-(3-(5-cyanopyrazin-2-ylamino)-1H-pyrazol-5-yl)-3-methoxyphenoxy)methyl)cyclopropyl)methylcarbamate (Compound 309-15)

To a solution of PPh$_3$ (240 mg, 0.91 mmol) in anhydrous THF (4 mL) was added DIAD (185 mg, 0.91 mmol) by syringe at 0-5° C., followed a solution of tert-butyl (1-(hydroxymethyl)cyclopropyl)methylcarbamate (110-13) (185 mg, 0.91 mmol) in anhydrous THF (2 mL). The resulting mixture was poured into a solution of compound 308-5 (118 mg, 0.30 mmol) in dry THF (2 mL) at ambient temperature and stirred for 1 h. The reaction mixture was quenched with water and extracted with ethyl acetate. The organic layer was washed with water and brine, dried over anhydrous sodium sulfate and evaporated in vacuo. The crude product was purified by column chromatography (dichloromethane/ethyl acetate: 3/1) to afford the title compound 309-15 as a yellow solid (300 mg).

Step 10b. 5-(5-(2-((1-(Aminomethyl)cyclopropyl) methoxy)-4-bromo-6-methoxyphenyl)-1H-pyrazol-3-ylamino)pyrazine-2-carbonitrile (Compound 15)

To a solution of compound 309-15 (300 mg, 50% purity) in DCM (3 mL) was added TFA (2 mL). The resulting mixture was stirred at ambient temperature for 1.5 h. The reaction mixture was evaporated in vacuo and purified by prep-HPLC (40%-90% CH$_3$CN in water, 0.1% CF$_3$COOH) to afford the title compound 15 as a pale yellow solid (48.2 mg, 39% yield via 2 steps). LCMS: 472.0 [M+1]$^+$. $^1$H NMR (400 MHz, DMSO-do): δ 0.48-0.49 (m, 4H), 2.64 (s, 2H), 3.86 (s, 3H), 3.99 (s, 2H), 6.95-6.96 (m, 2H), 7.01 (br, 1H), 8.50 (br, 1H), 8.61 (d, J=1.2 Hz, 1H).

Example 11

5-(5-(2-((1-(Aminomethyl)cyclopropyl)methoxy)-6-methoxy-4-methylphenyl)-1H-pyrazol-3-ylamino) pyrazine-2-carbonitrile (Compound 16)

Step 11a. tert-Butyl (1-((2-(3-(5-cyanopyrazin-2-ylamino)-1H-pyrazol-5-yl)-3-methoxy-5-methylphenoxy)methyl)cyclopropyl)methylcarbamate (Compound 309-16)

To a solution of PPh$_3$ (244 mg, 0.93 mmol) in anhydrous tetrahydrofuran (10 mL) was added DIAD (188 mg, 0.93 mmol) by syringe at 0-5° C., followed by a solution of tert-butyl (1-(hydroxymethyl)cyclopropyl)methylcarbamate (110-13) (187 mg, 0.93 mmol) in anhydrous tetrahydrofuran (5 mL). The resulting mixture was poured into a solution of compound 308-6 (100 mg, 0.31 mmol) in anhydrous tetrahydrofuran (5 mL) at ambient temperature and stirred at ambient temperature for 10 min. The reaction mixture was quenched with water and extracted with ethyl acetate. The organic layer was washed with water and brine, dried over anhydrous sodium sulfate and evaporated in vacuo. The crude product was purified by column chromatography (dichloromethane/ethyl acetate: 5/1) to afford the title compound 309-16 as a yellow solid (180 mg, crude). LCMS: 506.6 [M+1]$^+$.

Step 11b. 5-(5-(2-((1-(Aminomethyl)cyclopropyl) methoxy)-6-methoxy-4-methylphenyl)-1H-pyrazol-3-ylamino)pyrazine-2-carbonitrile (Compound 16)

To a solution of compound 309-16 (180 mg, crude) in dichloromethane (3 mL) was added trifluoroacetic acid (3 mL). The resulting mixture was stirred at ambient temperature for 1 h. The reaction mixture was evaporated in vacuo and purified by prep-HPLC (30%-90% CH$_3$CN in water, 0.1% CF$_3$COOH) to afford the title compound as a yellow solid compound 16 (60 mg, 48% yield via 2 steps). M.p.: 165-170° C. LCMS 406.4 [M+1]$^+$. $^1$H NMR (400 MHz, CD$_3$OD): δ 0.60-0.63 (m, 4H), 2.37 (s, 3H), 2.73 (s, 2H), 3.87 (s, 3H), 3.97 (s, 2H), 6.56 (s, 1H), 6.59 (s, 1H), 6.97 (s, 1H), 8.43 (br, 1H), 8.47 (d, J=1.2 Hz, 1H).

Example 12

5-(5-(2-((1-(Aminomethyl)cyclopropyl)methoxy)-4,6-dimethoxyphenyl)-1H-pyrazol-3-yl amino)pyrazine-2-carbonitrile (Compound 17)

Step 12a. tert-Butyl (1-((2-(3-(5-cyanopyrazin-2-ylamino)-1H-pyrazol-5-yl)-3,5-dimethoxyphenoxy) methyl)cyclopropyl)methylcarbamate (Compound 309-17)

To a solution of PPh$_3$ (244 mg, 0.90 mmol) in anhydrous tetrahydrofuran (10 mL) was added DIAD (188 mg, 0.90 mmol) by syringe at 0~5° C., followed by a solution of tert-butyl (1-(hydroxymethyl)cyclopropyl)methylcarbamate (110-13) (178 mg, 0.90 mmol) in anhydrous tetrahydrofuran (5 mL). The resulting mixture was poured into a solution of compound 308-7 (100 mg, 0.30 mmol) in anhydrous tetrahydrofuran (5 mL) at ambient temperature and stirred for 10 min. The reaction mixture was quenched with water and extracted with ethyl acetate. The organic layer was washed with water and brine, dried over anhydrous sodium sulfate and evaporated in vacuo. The crude product was purified by column chromatography (dichloromethane/ethyl acetate: 5/1) to afford the title compound 309-17 as a yellow solid (100 mg, crude). LCMS: 522.3 [M+1]$^+$.

Step 12b. 5-(5-(2-((1-(Aminomethyl)cyclopropyl)methoxy)-4,6-dimethoxyphenyl)-1H-pyrazol-3-ylamino)pyrazine-2-carbonitrile (Compound 17)

To a solution of compound 309-17 (100 mg, crude) in dichloromethane (3 mL) was added trifluoroacetic acid (3 mL). The resulting mixture was stirred at ambient temperature for 1 h. The reaction mixture was evaporated in vacuo. The residue was purified by prep-HPLC (35%-90% CH$_3$CN in water, 0.1% CF$_3$COOH) to afford the title compound 17 as a yellow solid (30 mg, 20% yield via 2 steps). M.p.: 160-164° C. LCMS 422.5 [M+1]$^+$. $^1$H NMR (400 MHz, DMSO-d$_6$): δ 0.49-0.52 (m, 4H), 2.67 (s, 2H), 3.81 (s, 3H), 3.83 (s, 3H), 3.96 (s, 2H), 6.32 (d, J=2.0 Hz, 2H), 6.92 (s, 1H), 8.52 (br, 1H), 8.61 (s, 1H).

Example 13

5-(5-(3-fluoro-6-methoxy-2-ol-((methylamino)methyl)cyclopropyl)methoxy)phenyl)-1H-pyrazol-3-ylamino)pyrazine-2-carbonitrile (Compound 18)

Step 13a. tert-Butyl (1-((2-(3-(5-cyanopyrazin-2-ylamino)-1H-pyrazol-5-yl)-6-fluoro-3-methoxyphenoxy)methyl)cyclopropyl)methyl(methyl)carbamate (Compound 111-18)

To a solution of PPh$_3$ (321 mg, 1.23 mmol) in anhydrous tetrahydrofuran (10 mL) was added DIAD (248 mg, 1.23 mmol) dropwise at 0-5° C. After 10 min, a solution of tert-butyl ((1-(hydroxymethyl)cyclopropyl)methyl)(methyl)carbamate (110-18) (263 mg, 1.23 mmol) in anhydrous tetrahydrofuran (5 mL) was added into the suspension at 0-5° C. The resulting mixture was added to a solution of 109 (100 mg, 0.31 mmol) in anhydrous tetrahydrofuran (5 mL) at ambient temperature and stirred for 1 h. The reaction mixture was quenched with water and extracted with ethyl acetate. The organic layer was washed with water and brine, dried over anhydrous sodium sulfate and evaporated in vacuo. The crude product was purified by column chromatography (dichloromethane/ethyl acetate: 5/1) to afford the title compound 111-18 as a yellow solid (230 mg, crude). LCMS: 524.4 [M+1]$^+$.

Step 13b. 5-(5-(3-fluoro-6-methoxy-2-((1-((methylamino)methyl)cyclopropyl)methoxy) phenyl)-1H-pyrazol-3-ylamino)pyrazine-2-carbonitrile (Compound 18)

To a solution of compound 111-18 (230 mg, crude) in dichloromethane (3 mL) was added trifluoroacetic acid (3 mL). The resulting mixture was stirred at ambient temperature for 1 h. The reaction mixture was evaporated in vacuo. The residue was purified by prep-HPLC (40%-90% CH$_3$CN in water, 0.1% CF$_3$COOH) to afford the title compound 18 as a yellow solid (40 mg, 30% yield via two steps). M.p.: 213-215° C. LCMS: 424.4 [M+1]$^+$. $^1$H NMR (400 MHz, DMSO-d$_6$): δ 0.41-0.42 (m, 4H), 2.25 (s, 3H), 2.42 (s, 2H), 3.78 (s, 2H), 3.80 (s, 3H), 6.86 (dd, J=9.2, 4.0 Hz, 1H), 6.96 (s, 1H), 7.28 (dd, J=11.2, 9.2 Hz, 1H), 8.53 (br, 1H), 8.65 (d, J=1.2 Hz, 1H).

Example 14

5-((5-(3-fluoro-2-methoxy-6-((1-((methylamino)methyl)cyclopropyl)methoxy)phenyl)-1H-pyrazol-3-yl)amino)pyrazine-2-carbonitrile (Compound 19)

Step 14a. tert-Butyl ((1-((2-(3-((5-cyanopyrazin-2-yl)amino)-1H-pyrazol-5-yl)-4-fluoro-3-methoxyphenoxy)methyl)cyclopropyl)methyl)(methyl)carbamate (Compound 211-19)

To a solution of PPh$_3$ (140 mg, 0.53 mmol) in anhydrous tetrahydrofuran (5 mL) was added DIAD (108 mg, 0.53 mmol) at 0-5° C., followed by a solution of tert-butyl ((1-(hydroxymethyl)cyclopropyl)methyl)(methyl)carbamate (110-18) (115 mg, 0.53 mmol) in anhydrous tetrahydrofuran (3 mL). The resulting mixture was added to a solution of 210 (58 mg, 0.18 mmol) in anhydrous tetrahydrofuran (3 mL) at ambient temperature and stirred at room temperature for 1 h. The reaction mixture was quenched with water and extracted with ethyl acetate. The organic layer was washed with water and brine, dried over anhydrous sodium sulfate and evaporated in vacuo. The crude product was purified by column chromatography (dichloromethane/ethyl acetate: 5/1) to afford the title compound 211-19 as a yellow solid (60 mg, crude). $^1$H NMR (400 MHz, DMSO-d$_6$): δ 0.54-0.57 (m, 4H), 1.15-1.23 (m, 9H), 2.72 (s, 3H), 3.29 (s, 2H), 3.73 (s, 3H), 3.76 (s, 2H), 6.77-6.80 (m, 1H), 7.23-7.29 (m, 1H), 8.49 (br, 1H), 8.62 (s, 1H), 10.80 (br, 1H), 12.38-12.47 (m 1H).

Step 14b. 5-((5-(3-fluoro-2-methoxy-6-ol-((methylamino)methyl)cyclopropyl)methoxy) phenyl)-1H-pyrazol-3-yl)amino)pyrazine-2-carbonitrile (Compound 19)

To a solution of compound 211-19 (60 mg, crude) in dichloromethane (3 mL) was added trifluoroacetic acid (3 mL). The resulting mixture was stirred at ambient temperature for 1 h. The reaction mixture evaporated in vacuo and the crude product was purified by prep-HPLC (35%-90% CH$_3$CN in water, 0.1% CF$_3$COOH) to afford the title compound 19 as a yellow solid (40 mg, 53% yield via two steps). M.p.: 215-219° C. LCMS: 424.4 [M+1]$^+$. $^1$H NMR (400 MHz, CD$_3$OD): δ 0.62-0.64 (m, 4H), 2.37 (s, 3H), 2.65 (s, 2H), 3.84 (d, J=1.2 Hz, 3H), 3.95 (s, 2H), 6.81 (dd, J=9.2, 4.0 Hz, 1H), 7.01 (s, 1H), 7.16 (dd, J=10.8, 9.2 Hz, 1H), 8.51 (br, 114), 8.53 (s, 1H).

Example 15

5-(5-(4-Fluoro-2-methoxy-6-((1-((methylamino)methyl)cyclopropyl)methoxy)phenyl)-1H-pyrazol-3-ylamino)pyrazine-2-carbonitrile (Compound 20)

Step 15a. tert-Butyl (1-((2-(3-(5-cyanopyrazin-2-ylamino)-1H-pyrazol-5-yl)-5-fluoro-3-methoxyphenoxy)methyl)cyclopropyl)methyl(methyl)carbamate (Compound 309-20)

To a solution of PPh$_3$ (451 mg, 1.72 mmol) in anhydrous tetrahydrofuran (10 mL) was added DIAD (348 mg, 1.72 mmol) dropwise at 0-5° C. After 10 min, to the suspension was added a solution of tert-butyl ((1-(hydroxymethyl)cyclopropyl)methyl)(methyl)carbamate (110-18) (370 mg, 1.72 mmol) in anhydrous tetrahydrofuran (5 mL) at 0-5° C. The resulting mixture was poured into a solution of compound 308-3 (140 mg, 0.43 mmol) in anhydrous tetrahydrofuran (5 mL) at ambient temperature and stirred for 1 h. The reaction mixture was quenched with water and extracted with ethyl acetate. The organic layer was washed with water and brine, dried over anhydrous sodium sulfate and evaporated in vacuo. The crude product was purified by column chromatography (dichloromethane/ethyl acetate: 5/1) to afford title compound 309-20 as a yellow solid (300 mg, crude). LCMS: 524.3 [M+1]+.

Step 15b. 5-(5-(4-Fluoro-2-methoxy-6-((1-((methylamino)methyl)cyclopropyl)methoxy) phenyl)-1H-pyrazol-3-ylamino)pyrazine-2-carbonitrile (Compound 20)

To a solution of compound 309-20 (300 mg, crude) in dichloromethane (3 mL) was added trifluoroacetic acid (3 mL). The resulting mixture was stirred at ambient temperature for 1 h. The reaction mixture was evaporated in vacuo and the residue was purified by pre-HPLC (40%-90% $CH_3CN$ in water, 0.1% $CF_3COOH$) to afford the title compound 20 as a yellow solid (20 mg, 11% yield via 2 steps). M.p.: 228-230° C. LCMS 424.1 [M+1]+. NMR (400 MHz, DMSO-$d_6$): δ 0.53 (d, J=8.0 Hz, 411), 2.32 (s, 3H), 2.57 (s, 2H), 3.85 (s, 3H), 3.95 (s, 2H), 6.64-6.70 (m, 2H), 6.98 (s, 1H), 8.54 (br, 1H), 8.62 (s, 2H), 10.71 (br, 1H).

Example 16

Ethyl 3-(2-(3-(5-cyanopyrazin-2-ylamino)-1H-pyrazol-5-yl)-5-fluoro-3-methoxy phenoxy)propylcarbamate (Compound 38)

To a suspension of compound 3 (75 mg, 0.19 mmol) and $K_2CO_3$ (54 mg, 0.39 mmol) in anhydrous tetrahydrofuran (10 mL) was added ethyl carbonochloridate (21 mg, 0.19 mmol) at 0° C. The resulting mixture was stirred at ambient temperature for 1 h. The reaction mixture was quenched with water and extracted with ethyl acetate. The organic layer was washed with water and brine, dried over anhydrous sodium sulfate and evaporated in vacuo. The crude product was purified by prep-HPLC (60%-90% $CH_3CN$ in water, 0.1% $CF_3COOH$) to afford the title compound 38 as a yellow solid (37 mg, 43% yield). LCMS: 456.5 [M+1]+. $^1H$ NMR (400 MHz, DMSO-$d_6$): δ 1.13 (t, J=6.8 Hz, 3H), 1.83-1.86 (m, 2H), 3.13 (q, J 6.4 Hz, 2H), 3.82 (s, 3H), 3.94 (q, J=6.8 Hz, 2H), 4.03 (t, J=6.0 Hz, 2H), 6.66-6.70 (m, 2H), 6.87 (s, 1H), 7.15 (t, J=5.6 Hz, 1H), 8.50 (br, 1H), 10.7 (s, 1H), 8.59 (s, 1H), 12.29 (s, 1H).

EXAMPLE 17: The following compounds can also be prepared using similar procedures to those set forth in Examples 1 to 16 above 5-(5-(2-(3-methylaminopropoxy)-4-fluoro-6-methoxyphenyl)-1H-pyrazol-3-ylamino) pyrazine-2-carbonitrile;
5-(5-(2-(3-methylaminopropoxy)-4-chloro-6-methoxyphenyl)-1H-pyrazol-3-ylamino) pyrazine-2-carbonitrile;
5-(5-(2-(3-methylaminopropoxy)-4-bromo-6-methoxyphenyl)-1H-pyrazol-3-ylamino) pyrazine-2-carbonitrile;
5-(5-(2-(3-methylaminopropoxy)-4-methyl-6-methoxyphenyl)-1H-pyrazol-3-ylamino) pyrazine-2-carbonitrile;
5-(5-(2-(3-methylaminopropoxy)-4,6-dimethoxyphenyl)-1H-pyrazol-3-ylamino) pyrazine-2-carbonitrile;
5-((5-(4-chloro-2-methoxy-6-((1-((methylamino)methyl)cyclopropyl)methoxy)phenyl)-1H-pyrazol-3-yl)amino) pyrazine-2-carbonitrile;
5-((5-(4-bromo-2-methoxy-6-((1-((methylamino)methyl)cyclopropyl)methoxy)phenyl)-1H-pyrazol-3-yl)amino) pyrazine-2-carbonitrile;
5-((5-(2-methoxy-4-methyl-6-((1-((methylamino)methyl)cyclopropyl)methoxy)phenyl)-1H-pyrazol-3-yl)amino) pyrazine-2-carbonitrile;
5-((5-(2,4-dimethoxy-6-((1-((methylamino)methyl)cyclopropyl)methoxy)phenyl)-1H-pyrazo 1-3-yl)amino)pyrazine-2-carbonitrile;
5-(5-(2-(2-hydroxy-3-aminopropoxy)-4-fluoro-6-methoxyphenyl)-1H-pyrazol-3-ylamino) pyrazine-2-carbonitrile;
5-(5-(2-(2-hydroxy-3-aminopropoxy)-4-methyl-6-methoxyphenyl)-1H-pyrazol-3-ylamino) pyrazine-2-carbonitrile;
5-(5-(2-(2-hydroxy-3-aminopropoxy)-4,6-dimethoxyphenyl)-1H-pyrazol-3-ylamino) pyrazine-2-carbonitrile,
2-methyl-5-(5-(2-(3-aminopropoxy)-4-fluoro-6-methoxyphenyl)-1H-pyrazol-3-ylamino) pyrazine;
2-chloro-5-(5-(2-(3-aminopropoxy)-4-fluoro-6-methoxyphenyl)-1H-pyrazol-3-ylamino) pyrazine;
2-methyl-5-(5-(2-(3-methylaminopropoxy)-4-fluoro-6-methoxyphenyl)-1H-pyrazol-3-yl amino)pyrazine;
2-chloro-5-(5-(2-(3-methylaminopropoxy)-4-fluoro-6-methoxyphenyl)-1H-pyrazol-3-yl amino)pyrazine;
2-methyl-5-(5-(2-((1-(aminomethyl)cyclopropyl)methoxy)-4-fluoro-6-methoxyphenyl)-1H-pyrazol-3-ylamino)pyrazine;
2-chloro-5-(5-(2-((1-(aminomethyl)cyclopropyl)methoxy)-4-fluoro-6-methoxyphenyl)-1H-pyrazol-3-ylamino)pyrazine;
2-methyl-5-(5-(2-((1-(aminomethyl)cyclopropyl)methoxy)-4-fluoro-6-methoxyphenyl)-1H-pyrazol-3-ylamino)pyrazine,
2-chloro-5-(5-(2-((1-(aminomethyl)cyclopropyl)methoxy)-4-fluoro-6-methoxyphenyl)-1H-pyrazol-3-ylamino)pyrazine;
2-methyl-5-(5-(2-(2-hydroxy-3-aminopropoxy)-4-fluoro-6-methoxyphenyl)-1H-pyrazol-3-yl amino)pyrazine;
2-chloro-5-(5-(2-(2-hydroxy-3-aminopropoxy)-4-fluoro-6-methoxyphenyl)-1H-pyrazol-3-yl amino)pyrazine;
2-amino-N-(3-(2-(3-((5-cyanopyrazin-2-yl)amino)-1H-pyrazol-5-yl)-5-fluoro-3-methoxyphenoxy)propyl)acetamide, or
1-(((3-(2-(3-((5-cyanopyrazin-2-yl)amino)-1H-pyrazol-5-yl)-5-fluoro-3-methoxyphenoxy)propyl)carbamoyl)oxy) ethyl isobutyrate.

In Vitro and In Vivo Pharmacological Studies
1. ChK1 Enzymatic Assay
1) In Vitro ADP-Glo Assay to Determine the Ability of Test Compounds to Inhibit Chk1 Activity The compounds were dissolved in 100% DMSO. 100 nl of compound was transferred to an Echo qualified 384-well assay plate (LABCYTE, Cat. No. P05525) with echo. The no compound control well contained 100 nl of 100% DMSO. 2.5 ul of 2 times dilution of Chk1 enzyme solution (BPS, Cat. No. 40039, Lot. No. 1001) was dispensed into the well with the compound at various concentrations and 2.5 ul of assay buffer (40 mM Tris at pH 7.5, 20 mM $MgCl_2$, 0.10% BSA, 1 mM DTT) added into low control wells. After incubation at room temperature for 10 minutes, 2.5 μl of 2 times dilution of the substrate peptide FAM-P10 (Invitrogen, Cat. No. 116583, Lot. No. P080804-WY116583) was added. After incubation at the temperature of 37° C. for 60 min, 5 μl of ADP-Glo reagent (Promega, Cat. No. v9102/3, Lot. No. 314795) was added and the plate was incubated at RT for 60 minutes. 10 ul kinase detection regent (Promega, Cat. No. v9102/3, Lot. No. 314795) was transferred into all wells, and the plate was incubated at room temperature for 30 minutes. The conversion data were read with Synergy (Biotek) and the RLU value was converted into inhibition values. The inhibition rate (%)=(max-conversion)/(max-min)*100.

2) In Vitro ADP-Glo Assay to Determine the Ability of Test Compounds to Inhibit Chk2 Activity The compounds were dissolved in 100% DMSO. 100 nl of the compound was transferred to an Echo qualified 384-well assay plate (LABCYTE, Cat. No. P05525) with echo. The no compound control well contained 100 nl of 100% DMSO. 2.5 ul of 2.5 times dilution of Chk2 enzyme solution (Carna, Cat. No. 02-162, Lot. No. 10CBS-0386) was dispensed into the well with the compound at various concentrations and 2.5 ul of assay buffer (40 mM Tris at pH 7.5, 20 mM $MgCl_2$, 0.10% BSA, 1 mM DTT) added into low control wells. After incubation at room temperature for 10 minutes, 2.5 μl of 2.5 times dilution of the substrate peptide FAM-P10 (Invitrogen, Cat. No. 116583, Lot. No. P080804-WY116583) was added. After incubation at the temperature of 37° C. for 60 min, 5 μl of ADP-Glo reagent (Promega, Cat. No. v9102/3, Lot. No. 314795) was added and the plate was incubated at 37° C. for 60 minutes. 10 ul kinase detection regent (Promega, Cat. No. v9102/3, Lot. No. 314795) was transferred into all wells, and the plate was incubated at room temperature for 30 minutes. The conversion data were read with Synergy (Biotek) and the RLU value was converted into inhibition values. The inhibition rate (%)=(max-conversion)/(max-min)*100.

The following Table 1 lists representative compounds of this invention and their activity in Chk1 and Chk2 assays. In these assays, the following grading was used: I>100 nM, 100 nM≥II>50 nM, 50 nM≥III>10 nM, 10 nM≥IV>1 nM, V≤1 nM.

TABLE 1

| In Vitro Enzyme Activity | | | | | |
|---|---|---|---|---|---|
| Compound # | Chk1 | Chk2 | Compound # | Chk1 | Chk2 |
| 1 | IV | — | 2 | V | — |
| 3 | V | II | 4 | V | II |
| 5 | V | II | 6 | V | II |
| 7 | IV | III | 13 | V | III |
| 14 | V | III | 15 | V | III |
| 16 | V | III | 17 | IV | III |
| 18 | IV | — | 19 | IV | — |
| 20 | V | — | 38 | III | — |
| LY-2606368 | V | II | GDC-0575 | IV | II |

2. Cancer Cell Growth Inhibition Assay

Human cancer cell lines were purchased from American Type Culture Collection (Manassas, Va.). The trypsinized cells were diluted to required volume at densities of 44,000 cells/ml. 90 ul cell slurry was dispensed per well in 96-well flat-bottomed plates with the recommended culture medium. The cells were incubated for 24 hours at 37° C. in 5% $CO_2$ under humidified condition. The cells were then incubated with compounds at various concentrations for 72 hours in culture medium supplemented with 0.5% (v/v) FBS. Growth inhibition was assessed by assay of cellular ATP content using CellTiter-Glo reagent to each well. Luminesce was read on Envision. The inhibition rate (%)=(Max signal compound signal)/(Max signal Min signal)×100.

The following Table 2 lists representative compounds of this invention and their anti cell proliferation activity in the cell-based assays. In these assays, the following grading was used: I>500 nM, 500 nM≥II>100 nM, 100 nM≥III>50 nM, 50 nM≥IV>10 nM, V≤10 nM.

TABLE 2

| Cell Proliferation Assay | | |
|---|---|---|
| Compound # | HT-29 | MDA-MB-231 |
| 1 | II | II |
| 2 | II | II |
| 3 | IV | III |
| 4 | IV | IV |
| 5 | IV | III |
| 6 | IV | IV |
| 7 | IV | IV |
| 13 | V | IV |
| 14 | IV | IV |
| 15 | IV | IV |
| 16 | V | IV |
| 17 | V | IV |
| 19 | III | II |
| 20 | V | IV |
| LY-2606368 | IV | IV |
| GDC-575 | II | II |

3. Western Blot Analysis

HT-29 colon cancer cells grown in monolayer culture were treated as indicated. In figure legends cell lysates were homogenized. Samples prepared after centrifugation at 13,000 rpm and boiling for 8 min. were loaded onto SDS-PAGE gel. Immunoblotting was done using standard procedures with blocking solution (TBST with 5% W/V nonfat dry milk) containing a primary Chk1 mouse antibody (CST Cat #2360, pChK1 (S296) antibody (CST Cat 2349) or β-actin antibody (CST Cat #4970) and IRDye 680RD- or IRDay 800CW-conjugated secondary antibodies (Li-COR Cat #926-68071, Cat #926-32210). Membranes were imaged with the LI-COR Odyssey Infrared Imaging System.

HT-29 cells were pre-incubated with Chk1 inhibitor at various concentrations for 0.5 hours followed by treatment with SN-38 (200 nM) for 16 hours. Compounds 3 and 13 showed similar potency to LY-260636 in inhibition of Chk1 phosphorylation in the HT-29 colon cells. GDC-575 was less potent than these compounds (FIG. 1). HT-29 cells were pre-incubated with SN-38 (50 nM) for 24 hours followed by treatment with ChK1 inhibitors at various concentrations for 3 hours. Both LY-260636 and Compound 3 potently inhibited ChK1 phosphorylation in the tumor cells (FIG. 2).

4. Pharmacokinetics Studies

Compounds were formulated in 30% SEB-β-CD (Zhiyuan Bio-technology) with 1 molar equivalents of HCl (pH adjusted to 3-5). Male SD rats (280-350 g) were purchased from Medical Laboratory Animal Center of Guangdong. Three rats were used for each PK study. Each rat was dosed via tail vein intravenous injection at 10 mg/kg. At various time points after compound administration, approximately 0.2~0.3 mL of blood was collected by cutting the end of tail into tubes containing K2-EDTA. The plasma was separated via centrifugation and stored at −80° C. A PE Sciex API-3000 LC-MS/MS system (Applied Biosystems, Inc.) was used to analyze compound concentrations in plasma.

PK studies of ChK1 inhibitors were conducted in rats after intravenous administration at 10 mg/kg. Animals did not tolerated LY-2606368 at 10 mg/kg in rats. The dose of LY-2606368 was adjusted to 5 mg/kg. The compounds 3, 4, 5, 14 and 15 displayed a longer half-life and higher exposure than LY2606368 (Table 3).

TABLE 3

PK Parameters of Compounds 3, 4, 5, 14 and 15

| Parameter | Unit | Compound # 3 | 14 | 4 | 15 | 5 | LY-2606368 |
|---|---|---|---|---|---|---|---|
| Dose | mg/kg | 10.0 | 10.0 | 10.0 | 10.0 | 10.0 | 5.0 |
| $t^{1/2}$ | h | 3.8 | 4.0 | 3.3 | 7.4 | 5.3 | 1.3 |
| $AUC_{0-t}$ | ng/ml*h | 4531 | 3095 | 2390 | 4890 | 2962 | 631 |
| $AUC_{0-inf}$ | ng/ml*h | 4637 | 3124 | 2402 | 4975 | 2989 | 637 |
| MRT | hr | 2.8 | 4.1 | 3.1 | 3.8 | 2.8 | 1.2 |
| Vd | L/kg | 12.3 | 19.2 | 22.1 | 46.9 | 29.5 | 14.7 |
| Vss | L/kg | 6.4 | 13.9 | 14.3 | 19.2 | 10.2 | 9.7 |
| CL | L/hr/kg | 2.3 | 3.4 | 4.7 | 3.8 | 3.6 | 7.9 |

5. Human Cancer Xenograft Model

Female Balb/c nude mice at 7-8 weeks of age (Body weights between 17-18g) were purchased from Hunan SJA Laboratory Animal Co., Ltd. HT-29 cells were cultured in DMEM culture medium containing 10% fetal bovine serum and LoVo cells were cultured in RPMI 1640 culture medium containing 10% fetal bovine serum. The cells were harvested and washed with serum free culture medium. Finally, the cells were suspended at a cell density of $0.5 \times 10^7$ cells/ml in serum free culture medium for implantation. 5 million cells per animal suspended in 0.1 ml serum free culture medium and 1.1 matrigel were injected into the right flank of the animals after a one, week acclimation period. When average tumor volume reached acceptable tumor size (100-200 mm$^3$) and shape, the animals were randomly assigned into treatment groups.

6. PK Study in Tumor-Bearing Mice

Compound 3 was selected for further PK studies in tumor bearing mice. HT-29 colon cancer cells were implanted to establish the xenograft model in Balb/c nude mice. Twenty-four mice were divided into 8 time groups with n=3/group. Compound 3 was dissolved in 30% SEB-β-CD (Zhiyuan Bio-technology) with 1 molar equivalents of HCl. Each animal was dosed via intravenous administration of Compound 3 at 40 mg/kg. Blood and tumors were collected at various time points after mice were euthanized with $CO_2$. Blood samples were centrifuged at 4° C. immediately after collection. The supernatants were transferred to 1.5 mL of Eppendorf vials as soon as possible and stored at −80° C. in a freezer. Tumor samples were collected and placed in dry ice until transferred to a −80° C. freezer for bioanalysis.

The compound was rapidly distributed into tumor tissues. The half-life was 6.1 hours and 14.0 hours in blood and tumor tissues, respectively. The tumor exposure was about 6-fold higher than the plasma exposure after IV administration (FIG. 3).

7. Efficacy Studies in Tumor Models

1) Compound 3 Inhibited Tumor Growth in HT-29 Colon Cancer Xenograft Model

HT-29 colon cancer cells were implanted to establish the xenograft model in Balb/c nude mice. Compound 3 and LY2606368 were dissolved in 30% SEB-β-CD (Zhiyuan Bio-technology) with 1 molar equivalents of HCl. GDC-575 was suspended in 0.5% methyl cellulose/0.1% Tween 80 in water. The treatment of Compound 3 (40 mg/kg, IV, twice a week) was more efficacious than the reference LY-2606368 (15 mg/kg, IV, twice a week) or GDC-575 (25 mg/kg, po, 3 times/week) at their MTD. The % T/C values were 31% for Compound 3 (P<0.001), 61% for LY-2606368 (P<0.05), 50% for GDC-0575 (P<0.001), respectively (Table 4). The animals well tolerated each treatment in the HT-29 colon cancer in nude mice model.

TABLE 4

Tumor growth inhibition by Compound 3 in HT-29 Xenograft Model

| Treatments | Tumor volume (mm$^3$) (X ± SD) | Tumor weight (mg) (X ± SD) | T/C value (%) | P Value |
|---|---|---|---|---|
| Vehicle Control (iv, 30% SEB-b-CD) | 903 ± 73 | 562 ± 39 | / | / |
| LY-2606368 (15 mg/kg, iv, 2 times/week) | 615 ± 10 | 390 ± 24 | 61 | <0.05 |
| Compound 3 (40 mg/kg, iv, 2 times/week) | 407 ± 17 | 272 ± 16 | 31 | <0.001 |
| Vehicle Control (po, 0.5% Methyl cellulose/0.1% Tween 80) | 911 ± 244 | 605 ± 183 | / | / |
| GDC-575 (25 mg/kg, po 3 time/week) | 515 ± 158 | 349 ± 94 | 50 | 0.001 |

2) Compound 3 Enhanced Anti-Tumor Activity of CPT11 in HT-29 Xenograft Model

In HT-29 tumor xenograft model, the animals were treated with a single compound, a ChK1 inhibitor or CPT-11, or a combination with CPT11. Both Compound 3 and LY-2606368 showed enhanced anti-tumor growth activity of CPT11 in the tumor model. The treatment of Compound 3 (40 mg/kg, IV, twice a week) alone or with CPT-11 (50 mg/kg, IV, once per week) was shown to be more efficacious than the reference LY-2606368 (15 mg/kg, IV, twice a week) alone or with CPT-11 (50 mg/kg, IV, once per week). The % T/C values were 26% (p<0.001) for Compound 3 alone and −9% (p<0.001) for Compound 3 plus CPT-11, and 61% (p<0.001) for LY-2606368 and 0% (p<0.001) for LY-2606368 plus CPT11, respectively (FIG. 4). The animals well tolerated each treatment in the HT-29 colon cancer in nude mice model.

3) Compound 3 Inhibited Tumor Growth in LoVo Colon Xenograft Model

Lovo colon cancer cells were implanted to establish the xenograft model in Balb/c nude mice. Compound 3 and LY2606368 were dissolved in 30% SEB-β-CD (Zhiyuan Bio-technology) with 1 molar equivalents of HCl. In LoVo tumor xenograft model, the treatment of LY2606368 at 15 mg/kg and Compound 3 at 10 mg/kg, 20 mg/kg, 40 mg/kg, IV, twice a week showed significant tumor growth inhibition in a dose-dependent manner. However, at MTD dose, the treatment of Compound 3 was more efficacious than LY2606368 in LoVo model. The T/C values were −77% for Compound 3 at 40 mg/kg, and −57% for LY-2606368 at 15 mg/kg, respectively (FIG. 5).

8. Metabolic Stability

Compounds (1 μM) were incubated with human liver S9 (from BD Gentest) at final liver microsomal protein concentration of 0.5 mg/mL for 0, 5, 15, 30, 45 min at 37° C. The remaining compounds in the reaction were measured by LC-MS/MS. The half-life (T½) 0.693/K (K is the rate constant from a plot of ln [concentration] vs. incubation time).

Compounds 3, 4, 13 and 15 were more metabolic stable than LY2606368 in human liver S9 microsomes. The half-life for these compounds was in the range of 165.41 to 6181 min (Table 5).

TABLE 5

Human liver S9 metabolic stability

| Compound # | Species | Percentage Remaining % | | | | | $T_{1/2}$ (min) |
|---|---|---|---|---|---|---|---|
| | | 0 min | 5 min | 15 min | 30 min | 45 min | |
| LY2606368 | Human | | | | | | 87.99 |
| 3 | Human | 100.00 | 96.98 | 94.32 | 65.38 | 77.05 | 165.41 |
| 4 | Human | 100.00 | 97.57 | 94.83 | 88.45 | 82.67 | 6181.11 |
| 13 | Human | 100.00 | 98.69 | 99.08 | 96.23 | 100.18 | 300.19 |
| 15 | Human | 100.00 | 94.64 | 93.89 | 93.30 | 87.68 | 479.55 |

What is claimed is:

1. A compound of formula (I):

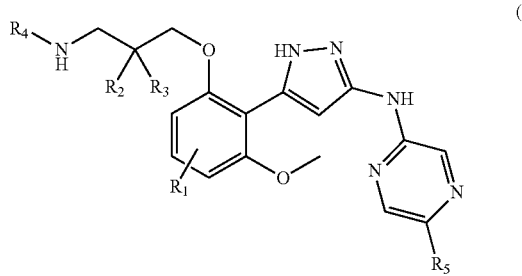

(I)

wherein:
$R_1$ is halogen, unsubstituted or substituted alkyl, unsubstituted or substituted alkenyl, unsubstituted or substituted alkynyl, unsubstituted or substituted cycloalkyl, unsubstituted or substituted alkoxy, unsubstituted or substituted aryl, —$NO_2$, —OH, —C(O)R, —C(O)OR, —C(O)N(R')(R"), or —N(R')(R");

$R_2$ and $R_3$ are each independently —H, halogen, unsubstituted or substituted alkyl, unsubstituted or substituted cycloalkyl, unsubstituted or substituted alkoxy, —$NO_2$, —OH, or —N(R')(R"), or $R_2$ and $R_3$ together with the carbon atom to which they are attached form an unsubstituted or substituted carbon cyclic or heterocyclic ring;

$R_4$ is —H, unsubstituted or substituted alkyl, unsubstituted or substituted cycloalkyl, unsubstituted or substituted alkoxy, unsubstituted or substituted aryl, —OH, —C(O)R, —C(O)OR, —C(O)N(R')(R"), or —N(R')(R");

$R_5$ is —CN, halogen, unsubstituted or substituted alkyl, unsubstituted or substituted alkenyl, unsubstituted or substituted alkynyl, unsubstituted or substituted cycloalkyl, unsubstituted or substituted alkoxy, —$NO_2$, —OH, or —N(R')(R");

R is unsubstituted or substituted alkyl; and

R' and R" are each independently —H or unsubstituted or substituted alkyl, or a pharmaceutically acceptable salt, geometric isomer, enantiomer, distereomer, racemate, prodrug, solvate, or hydrate thereof.

2. The compound according to claim 1, wherein:
$R_1$ is halogen, unsubstituted or substituted alkyl, unsubstituted or substituted alkenyl, unsubstituted or substituted alkynyl, unsubstituted or substituted alkoxy, —$NO_2$, —OH, —C(O)OR, —C(O)N(R')(R"), or —N(R')(R");

R is unsubstituted or substituted alkyl; and

R' and R" are each independently —H or unsubstituted or substituted alkyl.

3. The compound according to claim 2, wherein:
$R_1$ is halogen, unsubstituted alkyl, unsubstituted alkoxy, —OH, —$CF_3$, or hydroxyalkyl.

4. The compound according to claim 3, wherein:
$R_1$ is —F, —Cl, —Br, methyl, ethyl, propyl, isopropyl, methoxy, ethoxy, isopropoxy, —OH, —$CF_3$, or hydroxymethyl.

5. The compound according to claim 1, wherein:
$R_2$ and $R_3$ are each independently —H, —OH, halogen, unsubstituted or substituted alkyl, or —N(R')(R"), or $R_2$ and $R_3$ together with the carbon atom to which they are attached form an unsubstituted or substituted carbon cyclic or heterocyclic ring; and R' and R" are each independently —H or unsubstituted or substituted alkyl.

6. The compound according to claim 5, wherein:
$R_2$ and $R_3$ are each independently —H, —OH, halogen, unsubstituted alkyl, or hydroxyalkyl, or $R_2$ and $R_3$ together with the carbon atom to which they are attached form an unsubstituted carbon cyclic ring or heterocyclic ring.

7. The compound according to claim 6, wherein:

$R_2$ and $R_3$ are each independently —H, —OH, —F, —Cl, methyl, ethyl, or hydroxymethyl, or $R_2$ and $R_3$ together with the carbon atom to which they are attached form cyclopropyl, cyclobutyl, cyclopentyl, oxirane, aziridine, or azetidine.

8. The compound according to claim 1, wherein:

$R_4$ is —H, unsubstituted or substituted alkyl, —C(O)OR, or —C(O)R; and

R is unsubstituted or substituted alkyl.

9. The compound according to claim 8, wherein:

$R_4$ is —H, methyl, ethyl, propyl, acetyl, aminoacetyl, methoxycarbonyl, 1-(1-oxo-2-methylpropoxy)ethoxycarbonyl, or ethoxycarbonyl.

10. The compound according to claim 1, wherein:

$R_5$ is —CN, halogen, unsubstituted or substituted alkyl, unsubstituted or substituted alkenyl, or unsubstituted or substituted alkynyl.

11. The compound according to claim 10, wherein:

$R_5$ is —CN, halogen, or unsubstituted alkyl.

12. The compound according to claim 11, wherein:

$R_5$ is —CN, —F, —Cl, —Br, methyl, ethyl, propyl, or isopropyl.

13. The compound according to claim 1, which is a compound of formula (II):

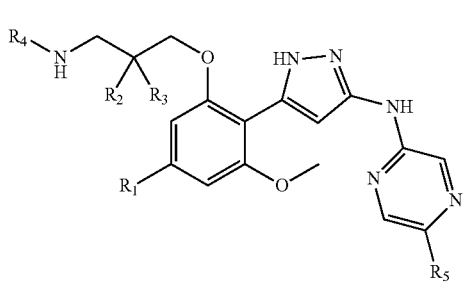

(II)

wherein:

$R_1$ is —F, —Cl, —Br, methyl, or methoxy;

$R_2$ and $R_3$ are each independently —H or —OH, or $R_2$ and $R_3$ together with the carbon atom to which they are attached form cyclopropyl;

$R_4$ is —H, methyl, aminoacetyl, 1-(1-oxo-2-methylpropoxy)ethoxycarbonyl, or ethoxycarbonyl; and $R_5$ is —CN, methyl, or —Cl, or a pharmaceutically acceptable salt, geometric isomer, enantiomer, distereomer, racemate, prodrug, solvate, or hydrate thereof.

14. A compound, which is selected from:

5-(5-(2-(3-aminopropoxy)-3-fluoro-6-methoxyphenyl)-1H-pyrazol-3-ylamino)pyrazine-2-carbonitrile;

5-((5-(6-(3-aminopropoxy)-3-fluoro-2-methoxyphenyl)-1H-pyrazol-3-yl)amino) pyrazine-2-carbonitrile;

5-(5-(2-(3-aminopropoxy)-4-fluoro-6-methoxyphenyl)-1H-pyrazol-3-ylamino)pyrazine-2-carbonitrile;

5-(5-(2-(3-aminopropoxy)-4-chloro-6-methoxyphenyl)-1H-pyrazol-3-yl amino)pyrazine-2-carbonitrile;

5-(5-(2-(3-aminopropoxy)-4-bromo-6-methoxyphenyl)-1H-pyrazol-3-ylamino)pyrazine-2-carbonitrile;

5-(5-(2-(3-aminopropoxy)-6-methoxy-4-methylphenyl)-1H-pyrazol-3-ylamino)pyrazine-2-carbonitrile;

5-(5-(2-(3-aminopropoxy)-4,6-dimethoxyphenyl)-1H-pyrazol-3-ylamino)pyrazine-2-carbonitrile;

5-(5-(2-(3-methylaminopropoxy)-4-fluoro-6-methoxyphenyl)-1H-pyrazol-3-ylamino) pyrazine-2-carbonitrile;

5-(5-(2-(3-methylaminoprop oxy)-4-chloro-6-methoxyphenyl)-1H-pyrazol-3-ylamino) pyrazine-2-carbonitrile;

5-(5-(2-(3-methylaminopropoxy)-4-bromo-6-methoxyphenyl)-1H-pyrazol-3-ylamino) pyrazine-2-carbonitrile;

5-(5-(2-(3-methylaminopropoxy)-4-methyl-6-methoxyphenyl)-1H-pyrazol-3-ylamino) pyrazine-2-carbonitrile;

5-(5-(2-(3-methylaminopropoxy)-4, 6-dimethoxyphenyl)-1H-pyrazol-3-ylamino) pyrazine-2-carbonitrile;

5-(5-(2-((1-(aminomethyl)cyclopropyl)methoxy)-4-fluoro-6-methoxyphenyl)-1H-pyrazol-3-ylamino)pyrazine-2-carbonitrile;

5-(5-(2-((1-(aminomethyl)cyclopropyl)methoxy)-4-chloro-6-methoxyphenyl)-1H-pyrazol-3-ylamino) pyrazine-2-carbonitrile;

5-(5-(2-((1-(aminomethyl)cyclopropyl)methoxy)-4-bromo-6-methoxyphenyl)-1H-pyrazol-3-ylamino) pyrazine-2-carbonitrile;

5-(5-(2-((1-(aminomethyl)cyclopropyl)methoxy)-6-methoxy-4-methylphenyl)-1H-pyrazol-3-ylamino) pyrazine-2-carbonitrile;

5-(5-(2-((1-(aminomethyl)cyclopropyl)methoxy)-4,6-dimethoxyphenyl)-1H-pyrazol-3-ylamino)pyrazine-2-carbonitrile;

5-(5-(3-fluoro-6-methoxy-2-((1-((methylamino)methyl)cyclopropyl)methoxy)phenyl)-1H-pyrazol-3-ylamino) pyrazine-2-carbonitrile;

5-((5-(3-fluoro-2-methoxy-6-((1-((methylamino)methyl)cyclopropyl)methoxy)phenyl)-1H-pyrazol-3-yl)amino) pyrazine-2-carbonitrile;

5-(5-(4-fluoro-2-methoxy-6-((1-((methylamino)methyl)cyclopropyl)methoxy)phenyl)-1H-pyrazol-3-ylamino) pyrazine-2-carbonitrile;

5-((5-(4-chloro-2-methoxy-6-((1-((methylamino)methyl)cyclopropyl)methoxy)phenyl)-1H-pyrazol-3-yl)amino) pyrazine-2-carbonitrile;

5-((5-(4-bromo-2-methoxy-6-((1-((methylamino)methyl)cyclopropyl)methoxy)phenyl)-1H-pyrazol-3-yl)amino) pyrazine-2-carbonitrile;

5-((5-(2-methoxy-4-methyl-6-((1-((methylamino)methyl)cyclopropyl)methoxy)phenyl)-1H-pyrazol-3-yl)amino) pyrazine-2-carbonitrile;

5-((5-(2,4-dim ethoxy-6-((1-((methyl amino)methyl)cyclopropyl)methoxy)phenyl)-1H-pyrazol-3-yl)amino) pyrazine-2-carbonitrile;

5-(5-(2-(2-hydroxy-3-aminopropoxy)-4-fluoro-6-methoxyphenyl)-1H-pyrazol-3-yl amino)pyrazine-2-carbonitrile;

5-(5-(2-(2-hydroxy-3-aminopropoxy)-4-methyl-6-methoxyphenyl)-1H-pyrazol-3-yl amino)pyrazine-2-carbonitrile;

5-(5-(2-(2-hydroxy-3-aminopropoxy)-4,6-dimethoxyphenyl)-1H-pyrazol-3-yl amino)pyrazine-2-carbonitrile;

2-methyl-5-(5-(2-(3-aminopropoxy)-4-fluoro-6-methoxyphenyl)-1H-pyrazol-3-ylamino)pyrazine;

2-chloro-5-(5-(2-(3-aminopropoxy)-4-fluoro-6-methoxyphenyl)-1H-pyrazol-3-ylamino)pyrazine;

2-methyl-5-(5-(2-(3-methylaminopropoxy)-4-fluoro-6-methoxyphenyl)-1H-pyrazol-3-ylamino)pyrazine;

2-chloro-5-(5-(2-(3-methylaminopropoxy)-4-fluoro-6-methoxyphenyl)-1H-pyrazol-3-ylamino)pyrazine;

2-methyl-5-(5-(2-((1-(aminomethyl)cyclopropyl)
methoxy)-4-fluoro-6-methoxyphenyl)-1H-pyrazol-3-
ylamino)pyrazine;
2-chloro-5-(5-(2-((1-(aminomethyl)cyclopropyl)
methoxy)-4-fluoro-6-methoxyphenyl)-1H-pyrazol-3-
ylamino)pyrazine;
2-methyl-5-(5-(2-((1-(aminomethyl)cyclopropyl)
methoxy)-4-fluoro-6-methoxyphenyl)-1H-pyrazol-3-
ylamino)pyrazine;
2-chloro-5-(5-(2-((1-(aminomethyl)cyclopropyl)
methoxy)-4-fluoro-6-methoxyphenyl)-1H-pyrazol-3-
ylamino)pyrazine;
2-methyl-5-(5-(2-(2-hydroxy-3-aminopropoxy)-4-fluoro-
6-methoxyphenyl)-1H-pyrazol-3-ylamino)pyrazine;
2-chloro-5-(5-(2-(2-hydroxy-3-aminopropoxy)-4-fluoro-
6-methoxyphenyl)-1H-pyrazol-3-ylamino)pyrazine;
ethyl 3-(2-(3-(5-cyanopyrazin-2-ylamino)-1H-pyrazol-5-
yl)-5-fluoro-3-methoxy phenoxy)propylcarbamate;
2-amino-N-(3-(2-(3-((5-cyanopyrazin-2-yl)amino)-1H-
pyrazol-5-yl)-5-fluoro-3-methoxyphenoxy)propyl)ac-
etamide; or
1-(((3-(2-(3-((5-cyanopyrazin-2-yl)amino)-1H-pyrazol-
5-yl)-5-fluoro-3-methoxy phenoxy)propyl)carbamoyl)
oxy)ethylisobutyrate;
or a pharmaceutically acceptable salt, geometric isomer,
enantiomer, distereomer, racemate, prodrug, solvate, or
hydrate thereof.

15. The compound according to claim 14, which is selected from:

5-(5-(2-(3-aminopropoxy)-3-fluoro-6-methoxyphenyl)-
1H-pyrazol-3-ylamino)pyrazine-2-carbonitrile;
5-((5-(6-(3-aminopropoxy)-3-fluoro-2-methoxyphenyl)-
1H-pyrazol-3-yl)amino) pyrazine-2-carbonitrile;
5-(5-(2-(3-aminopropoxy)-4-fluoro-6-methoxyphenyl)-
1H-pyrazol-3-ylamino)pyrazine-2-carbonitrile;
5-(5-(2-(3-aminopropoxy)-4-chloro-6-methoxyphenyl)-
1H-pyrazol-3-ylamino)pyrazine-2-carbonitrile;
5-(5-(2-(3-aminopropoxy)-4-bromo-6-methoxyphenyl)-
1H-pyrazol-3-ylamino)pyrazine-2-carbonitrile;
5-(5-(2-(3-aminopropoxy)-6-methoxy-4-methylphenyl)-
1H-pyrazol-3-ylamino)pyrazine-2-carbonitrile;
5-(5-(2-(3-aminopropoxy)-4,6-dimethoxyphenyl)-1H-
pyrazol-3-ylamino)pyrazine-2-carbonitrile;
5-(5-(2-((1-(aminomethyl)cyclopropyl)methoxy)-4-
fluoro-6-methoxyphenyl)-1H-pyrazol-3-ylamino)pyra-
zine-2-carbonitrile;
5-(5-(2-((1-(aminomethyl)cyclopropyl)methoxy)-4-
chloro-6-methoxyphenyl)-1H-pyrazol-3-ylamino)
pyrazine-2-carbonitrile;
5-(5-(2-((1-(aminomethyl)cyclopropyl)methoxy)-4-
bromo-6-methoxyphenyl)-1H-pyrazol-3-ylamino)
pyrazine-2-carbonitrile;
5-(5-(2-((1-(aminomethyl)cyclopropyl)methoxy)-6-
methoxy-4-methylphenyl)-1H-pyrazol-3-ylamino)
pyrazine-2-carbonitrile;
5-(5-(2-((1-(aminomethyl)cyclopropyl)methoxy)-4,6-di-
methoxyphenyl)-1H-pyrazol-3-ylamino)pyrazine-2-
carbonitrile;
5-(5-(3-fluoro-6-methoxy-2-((1-((methylamino)methyl)
cyclopropyl)methoxy)phenyl)-1H-pyrazol-3-ylamino)
pyrazine-2-carbonitrile;
5-((5-(3-fluoro-2-methoxy-6-((1-((methyl amino)methyl)
cyclopropyl)methoxy)phenyl)-1H-pyrazol-3-yl)amino)
pyrazine-2-carbonitrile;
5-(5-(4-fluoro-2-methoxy-6-((1-((methylamino)methyl)
cyclopropyl)methoxy)phenyl)-1H-pyrazol-3-ylamino)
pyrazine-2-carbonitrile; and ethyl 3-(2-(3-(5-cyanopyrazin-2-ylamino)-1H-pyrazol-5-
yl)-5-fluoro-3-methoxyphenoxy)propylcarbamate,
or a pharmaceutically acceptable salt, geometric isomer,
enantiomer, distereomer, racemate, prodrug, solvate, or
hydrate thereof.

16. A pharmaceutical composition comprising a therapeutically effective amount of a compound of claim 1 or a pharmaceutically acceptable salt, geometric isomer, enantiomer, distereomer, racemate, prodrug, solvate, or hydrate thereof, and a pharmaceutically acceptable carrier or excipient.

17. A pharmaceutical composition comprising a therapeutically effective amount of a compound of claim 14 or a pharmaceutically acceptable salt, geometric isomer, enantiomer, distereomer, racemate, prodrug, solvate, or hydrate thereof, and a pharmaceutically acceptable carrier or excipient.

18. A pharmaceutical composition comprising a therapeutically effective amount of a compound of claim 15 or a pharmaceutically acceptable salt, geometric isomer, enantiomer, distereomer, racemate, prodrug, solvate, or hydrate thereof, and a pharmaceutically acceptable carrier or excipient.

19. A method for treating cancer in a subject in need thereof comprising administrating a therapeutically effective amount of a compound of claim 1 or a pharmaceutically acceptable salt, geometric isomer, enantiomer, distereomer, racemate, prodrug, solvate, or hydrate thereof to the subject.

20. The method according to claim 19, comprising further administrating to the subject a second anticancer agent, a surgical therapy, an ionizing radiation, or a combination thereof.

21. The method according to claim 20, wherein the second anticancer agent is selected from: targeted cancer drugs, such as trastuzumab, ramucirumab, vismodegib, sonidegib, bevacizumab, everolimus, tamoxifen, toremifene, fulvestrant, anastrozole, exemestane, lapatinib, letrozole, pertuzumab, ado-trastuzumab emtansine, palbociclib, cetuximab, panitumumab, ziv-aflibercept, regorafenib, lmatinib mesylate, lanreotide acetate, sunitinib, regorafenib, denosumab, alitretinoin, sorafenib, pazopanib, temsirolimus, everolimus, tretinoin, dasatinib, nilotinib, bosutinib, rituximab, alemtuzumab, ofatumumab, obinutuxumab, ibrutinib, idelalisib, blinatumomab, soragenib, crizotinib, erlotinib, gefitinib, afatinib dimaleate, ceritnib, ramucirumab, nivolumab, pembrolizumab, osimertinib, and necitumumab; an alkylating agent, such as busulfan, chlorambucil, cyclophosphamide, iphosphamide, melphalan, nitrogen mustard, streptozocin, thiotepa, uracil nitrogen mustard, triethylenemelamine, temozolomide, and 2-chloroethyl-3-sarcosinamide-l-nitrosourea (SarCNU); an antibiotic or plant alkaloid, such as actinomycin-D, bleomycin, cryptophycins, daunorubicin, doxorubicin, idarubicin, irinotecan, L-asparaginase, mitomycin-C, mitramycin, navelbine, paclitaxel, docetaxel, topotecan, vinblastine, vincristine, teniposide (VM-26), and etoposide (VP-16); a hormone or steroid, such as 5α-reductase inhibitor, aminoglutethimide, anastrozole, bicalutamide, chlorotrianisene, diethyl stilbestrol (DES), dromostanolone, estramustine, ethinyl estradiol, flutamide, fluoxymesterone, goserelin, hydroxyprogesterone, letrozole, leuprolide, medroxyprogesterone acetate, megestrol acetate, methyl prednisolone, methyltestosterone, mitotane, nilutamide, prednisolone, arzoxifene (SERM-3), tamoxifen, testolactone, testosterone, triamicnolone, and zoladex; a synthetic, such as all-trans retinoic acid, carmustine (BCNU), carboplatin (CBDCA), lomustine (CCNU), cis-diaminedichloroplatinum (cisplatin), dacarbazine, gliadel, hexamethylmelamine, hydroxyurea, levamisole, mitoxantrone, o, p'-dichlorodiphenyldichloroethane (o,p'-DDD) (also known as lysodren or mitotane), oxaliplatin, porfimer sodium, procarbazine, and imatinib mesylate; an antimetabolite, such as chlorodeoxyadenosine, cytosine arabinoside, 2'-deoxycoformycin, fludarabine phosphate, 5-fluorouracil (5-FU), 5-fluoro-2'-deoxyuridine (5-FUdR), gemcitabine, camptothecin, 6-mercaptopurine, methotrexate, 4-methylthioamphetamine (4-MTA), and thioguanine; and a biologic, such as alpha interferon, BCG (*Bacillus* Calmette-Guerin), granulocyte colony stimulating factor (G-CSF), granulocyte-macrophage colony-stimulating factor (GM-CSF), interleukin-2, and herceptin.

22. The method according to claim 21, wherein the second anticancer agent is irinotecan.

23. The method according to claim 19, wherein the cancer is breast cancer, squamous cell carcinoma, lung cancer, oesophagus cancer, liver cancer, gastric cancer, colorectal cancer, bladder cancer, ovary carcinoma, prostate cancer, giloblastoma, pancreatic cancer, or leukemia.

24. A method for treating cancer in a subject in need thereof comprising administrating a therapeutically effective amount of a compound of claim 14 or a pharmaceutically acceptable salt, geometric isomer, enantiomer, distereomer, racemate, prodrug, solvate, or hydrate thereof to the subject.

25. The method according to claim 24, comprising further administrating to the subject a second anticancer agent, a surgical therapy, an ionizing radiation, or a combination thereof.

26. The method according to claim 25, wherein the second anticancer agent is selected from: targeted cancer drugs, such as trastuzumab, ramucirumab, vismodegib, sonidegib, bevacizumab, everolimus, tamoxifen, toremifene, fulvestrant, anastrozole, exemestane, lapatinib, letrozole, pertuzumab, ado-trastuzumab emtansine, palbociclib, cetuximab, panitumumab, ziv-aflibercept, regorafenib, lmatinib mesylate, lanreotide acetate, sunitinib, regorafenib, denosumab, alitretinoin, sorafenib, pazopanib, temsirolimus, everolimus, tretinoin, dasatinib, nilotinib, bosutinib, rituximab, alemtuzumab, ofatumumab, obinutuxumab, ibrutinib, idelalisib, blinatumomab, soragenib, crizotinib, erlotinib, gefitinib, afatinib dimaleate, ceritnib, ramucirumab, nivolumab, pembrolizumab, osimertinib, and necitumumab; an alkylating agent, such as busulfan, chlorambucil, cyclophosphamide, iphosphamide, melphalan, nitrogen mustard, streptozocin, thiotepa, uracil nitrogen mustard, triethylenemelamine, temozolomide, and 2-chloroethyl-3-sarcosinamide-l-nitrosourea (SarCNU); an antibiotic or plant alkaloid, such as actinomycin-D, bleomycin, cryptophycins, daunorubicin, doxorubicin, idarubicin, irinotecan, L-asparaginase, mitomycin-C, mitramycin, navelbine, paclitaxel, docetaxel, topotecan, vinblastine, vincristine, teniposide (VM-26), and etoposide (VP-16); a hormone or steroid, such as 5α-reductase inhibitor, aminoglutethimide, anastrozole, bicalutamide, chlorotrianisene, diethyl stilbestrol (DES), dromostanolone, estramustine, ethinyl estradiol, flutamide, fluoxymesterone, goserelin, hydroxyprogesterone, letrozole, leuprolide, medroxyprogesterone acetate, megestrol acetate, methyl prednisolone, methyltestosterone, mitotane, nilutamide, prednisolone, arzoxifene (SERM-3), tamoxifen, testolactone, testosterone, triamicnolone, and zoladex; a synthetic, such as all-trans retinoic acid, carmustine (BCNU), carboplatin (CBDCA), lomustine (CCNU), cis-diaminedichloroplatinum (cisplatin), dacarbazine, gliadel, hexamethylmelamine, hydroxyurea, levamisole, mitoxantrone, o, p'-dichlorodi phenyl di chloroethane (o,p'-DDD) (also known as lysodren or mitotane), oxaliplatin, porfimer sodium, procarbazine, and imatinib mesylate; an antimetabolite, such as chlorodeoxyadenosine, cytosine arabinoside, 2'-deoxycoformycin, fludarabine phosphate, 5-fluorouracil (5-FU), 5-fluoro-2'-deoxyuridine (5-FUdR), gemcitabine, camptothecin, 6-mercaptopurine, methotrexate, 4-methylthioamphetamine (4-MTA), and thioguanine; and a biologic, such as alpha interferon, BCG (*Bacillus* Calmette-Guerin), granulocyte colony stimulating factor (G-CSF), granulocyte-macrophage colony-stimulating factor (GM-CSF), interleukin-2, and herceptin.

27. The method according to claim 26, wherein the second anticancer agent is irinotecan.

28. The method according to claim 24, wherein the cancer is breast cancer, squamous cell carcinoma, lung cancer, oesophagus cancer, liver cancer, gastric cancer, colorectal cancer, bladder cancer, ovary carcinoma, prostate cancer, giloblastoma, pancreatic cancer, or leukemia.

29. A method for treating cancer in a subject in need thereof comprising administrating a therapeutically effective amount of a compound of claim 15 or a pharmaceutically acceptable salt, geometric isomer, enantiomer, distereomer, racemate, prodrug, solvate, or hydrate thereof to the subject.

30. The method according to claim 29, comprising further administrating to the subject a second anticancer agent, a surgical therapy, an ionizing radiation, or a combination thereof.

31. The method according to claim 30, wherein the second anticancer agent is selected from: targeted cancer drugs, such as trastuzumab, ramucirumab, vismodegib, sonidegib, bevacizumab, everolimus, tamoxifen, toremifene, fulvestrant, anastrozole, exemestane, lapatinib, letrozole, pertuzumab, ado-trastuzumab emtansine, palbociclib, cetuximab, panitumumab, ziv-aflibercept, regorafenib, lmatinib mesylate, lanreotide acetate, sunitinib, regorafenib, denosumab, alitretinoin, sorafenib, pazopanib, temsirolimus, everolimus, tretinoin, dasatinib, nilotinib, bosutinib, rituximab, alemtuzumab, ofatumumab, obinutuxumab, ibrutinib, idelalisib, blinatumomab, soragenib, crizotinib, erlotinib, gefitinib, afatinib dimaleate, ceritnib, ramucirumab, nivolumab, pembrolizumab, osimertinib, and necitumumab; an alkylating agent, such as busulfan, chlorambucil, cyclophosphamide, iphosphamide, melphalan, nitrogen mustard, streptozocin, thiotepa, uracil nitrogen mustard, triethylenemelamine, temozolomide, and 2-chloroethyl-3-sarcosinamide-l-nitrosourea (SarCNU); an antibiotic or plant alkaloid, such as actinomycin-D, bleomycin, cryptophycins, daunorubicin, doxorubicin, idarubicin, irinotecan, L-asparaginase, mitomycin-C, mitramycin, navelbine, paclitaxel, docetaxel, topotecan, vinblastine, vincristine, teniposide (VM-26), and etoposide (VP-16); a hormone or steroid, such as 5a-reductase inhibitor, aminoglutethimide, anastrozole, bicalutamide, chlorotrianisene, diethyl stilbestrol (DES), dromostanolone, estramustine, ethinyl estradiol, flutamide, fluoxymesterone, goserelin, hydroxyprogesterone, letrozole, leuprolide, medroxyprogesterone acetate, megestrol acetate, methyl prednisolone, methyltestosterone, mitotane, nilutamide, prednisolone, arzoxifene (SERM-3), tamoxifen, testolactone, testosterone, triamicnolone, and zoladex; a synthetic, such as all-trans retinoic acid, carmustine (BCNU), carboplatin (CBDCA), lomustine (CCNU), cis-diaminedichloroplatinum (cisplatin), dacarbazine, gliadel, hexamethylmelamine, hydroxyurea, levamisole, mitoxantrone, o, p'-dichlorodiphenyldichloroethane (o,p'-DDD) (also known as lysodren or mitotane), oxaliplatin, porfimer sodium, procarbazine, and imatinib mesylate; an antimetabolite, such as chlorodeoxyadenosine, cytosine arabinoside, 2'-deoxycoformycin, fludarabine phosphate, 5-fluorouracil (5-FU), 5-fluoro-2'-deoxyuridine (5-FUdR), gemcitabine, camptothecin, 6-mercaptopurine, methotrexate, 4-methylthioamphetamine (4-MTA), and thioguanine; and a biologic, such as alpha interferon, BCG (*Bacillus* Calmette-Guerin), granulocyte colony stimulating factor (G-CSF), granulocyte-macrophage colony-stimulating factor (GM-CSF), interleukin-2, and herceptin.

32. The method according to claim 31, wherein the second anticancer agent is irinotecan.

33. The method according to claim 29, wherein the cancer is breast cancer, squamous cell carcinoma, lung cancer, oesophagus cancer, liver cancer, gastric cancer, colorectal cancer, bladder cancer, ovary carcinoma, prostate cancer, gilobla stoma, pancreatic cancer, or leukemia.

34. A method for preparing a compound of claim 1, which comprises:

a. reacting a compound of formula (1)

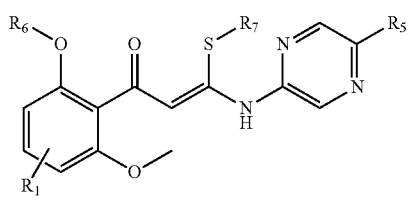

(1)

with a hydrazine of formula $H_2N\text{-}NH_2$, wherein $R_1$ and $R_5$ are as defined in claim 1; $R_6$ is a hydroxy protecting group; $R_7$ is alkyl; in the presence of a solvent to obtain a compound of formula (2);

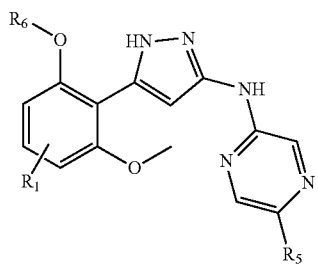

(2)

b. de-protecting the compound of formula (2), followed by reacting the de-protected compound with a compound of formula (3)

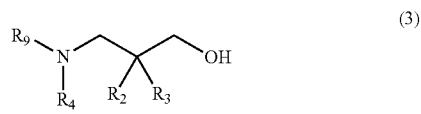

(3)

wherein $R_2$, $R_3$, and $R_4$ are as defined in claim 1; and $R_9$ is an amino protecting group, in the presence of a coupling agent and a solvent to obtain a compound of formula (4)

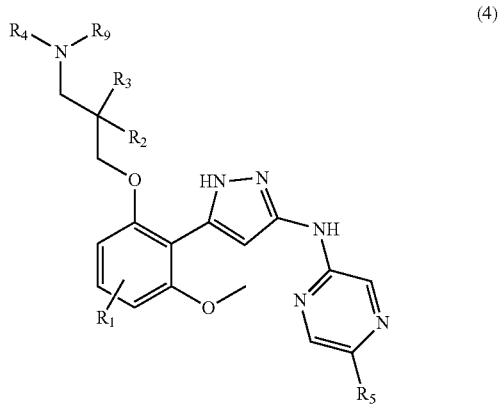

(4)

wherein $R_1$, $R_2$, $R_3$, $R_4$, $R_5$ and $R_9$ are as defined above; and c. de-protecting the compound of formula (4) to obtain a compound of formula (I).

* * * * *